US005602019A

United States Patent [19]
Beavo et al.

[11] Patent Number: 5,602,019
[45] Date of Patent: Feb. 11, 1997

[54] DNA ENCODING MAMMALIAN PHOSPHODIESTERASES

[75] Inventors: Joseph A. Beavo; Kelley J. Bentley, both of Seattle, Wash.; Harry Charbonneau, W. Lafayette, Ind.; William K. Sonnenburg, Seattle, Wash.

[73] Assignee: The Board of Regents of The University of Washington, Seattle, Wash.

[21] Appl. No.: 297,510

[22] Filed: Aug. 29, 1994

Related U.S. Application Data

[60] Division of Ser. No. 872,644, Apr. 20, 1992, Pat. No. 5,389,527, which is a continuation-in-part of Ser. No. 688,356, Apr. 19, 1991, abandoned.

[51] Int. Cl.$^6$ ............................. C12N 1/16; C12N 9/16; C12N 15/55; C12N 15/63
[52] U.S. Cl. .................. 435/196; 435/199; 435/252.3; 435/254.2; 435/320.1; 435/325; 536/23.2
[58] Field of Search ...................... 435/195, 199, 435/172.3, 320.1, 254.11, 196, 240.1, 252.3, 254.2; 536/23.2

[56] References Cited

PUBLICATIONS

Ausubel et al., eds., *Current Protocols in Molecular Biology*, 1:1.7.1–1.7.2 and 9.2.1–9.2.3, John Wiley & Sons, New York (1989).
Beavo, "Multiple Isozymes of Cyclic Nucleotide Phosphodiesterase", *Advances in Second Messenger and Phosphoprotein Research*, 22: 1–38 (1988).
Beavo, "Multiple Phosphodiesterase Isoenzymes Background, Nomenclature and Implications", pp. 3–15; *Cyclic Nucleotide Phosphodiesterases: Structure, Regulation and Drug Action*, J. Beavo and Houslay, M.D., Eds.; John Wiley & Sons, Ltd., New York (1990).
Birnstiel et al., "Transcription Termination and 3' Processing: The End Is in Sight!", *Cell*, 41:349–359 (1985).
Bourne et al., "Somatic Genetic Analysis of Cyclic AMP Action: Characterization of Unresponsive Mutants", *J. Cell. Physiol.*, 85:611–620 (1985).
Bradford, "A Rapid and Sensitive Method for the Quantitation of Microgram Quantities of Protein Utilizing the Principle of Protein–Dye Binding", *Analytical Biochem.*, 72:248–254 (1976).
Chen et al., "Molecular Analysis of cDNA Clones and the Corresponding Genomic Coding Sequences of the Drosophila dunce$^+$ Gene, the Structural Gene for cAMP Phosphodiesterase", *Proc. Nat'l. Acad. Sci. (USA)*, 83:9313–9317 (1986).
Chomczynski et al., "Single–Step Method of RNA Isolation by Acid Guanidinium Thiocyanate–Phenol–Chloroform Extraction", *Analytical Biochem.*, 162:156–159 (1987).
Colicelli et., "Isolation and Characterization of a Mammalian Gene Encoding a High–Affinity cAMP Phosphodiesterase", *Proc. Nat'l. Acad. Sci. (USA)*, 86:3599–3603 (1989).

Davis, "Molecular Genetics of the Cyclic Nucleotide Phosphodiesterases", pp. 227–241 in *Cyclic Nucleotide Phosphodiesterases: Structure, Regulation and Drug Action*, J. Beavo and Houslay, M.D., Eds.: John Wiley & Sons, Ltd., New York (1990).
Davis et al., "Cloning and Characterization of Mammalian Homologs of the Drosophila dunce$^+$ Gene", *Proc. Nat'l Acad. Sci. (USA)*, 86:3604–3608 (1989).
Devereux et al., "A Comprehensive Set of Sequence Analysis Programs for the VAX", *Nucleic Acids Res.*, 12:387–395 (1984).
Erneux et al., "A Mechanism in the Control of Intracellular cAMP Levels: The Activation of a Calmodulin–Sensitive Phosphodiesterase by a Rise of Intracellular Free Calcium", *Mol. Cell. Endocrinol.*, 43:123–134 (1985).
Faure et al., "Disruption of *Dictyostelium discoideum* Morphogenesis by Overproduction of cAMP Phosphodiesterase", *Proc. Nat'l. Acad. Sci. (USA)*, 85:8076–8080 (1988).
Feinberg et al., "A Technique for Radiolabeling DNA Restriction Endonuclease Fragments to High Specific Activity", *Analytical Biochem.*, 137:266–267 (1984).
Greenberg et al., "Enzymatic Regulation of the Concentration of Cyclic GMP in Mouse Brain", *Neuropharmacology*, 17:737–745 (1978).
Hansen et al., "Differential Recognition of Calmodulin–Enzyme Complexes by a Conformation–Specific Anti–Calmodulin Monoclonal Antibody", *J. Biol. Chem.*, 261:14636–14645 (1986).
Hansen et al, "Purification of Calmodulin–Stimulated Cyclic Nucleotide Phosphodiesterase by Using Conformation–Specific Monoclonal Antibody Chromatography", *Proc. Nat'l. Acad. Sci. (USA)*, 79:2788–2792 (1982).
Hansen et al., "Purification of Two Calcium/Calmodulin–Stimulated Cyclic Nucleotide Phosphodiesterase by Monoclonal Antibody Affinity Chromatography", *Meth. Enzymol.*, 159:543–557 (1988).
Hashimoto et al., "Regulation of $Ca^{2+}$/Calmodulin–Dependent Cyclic Nucleotide Phosphodiesterase by the Autophosphorylated Form of $Ca^{2+}$/Calmodulin–Dependent Protein Kinase II", *J. Biol. Chem.*, 264:10884–10887 (1989).
Henikoff, "Unidirectional Digestion with Exonuclease III Creates Targeted Breakpoints for DNA Sequencing", *Gene*, 28:351–359 (1984).

(List continued on next page.)

*Primary Examiner*—Dian C. Jacobson
*Attorney, Agent, or Firm*—Marshall, O'Toole, Gerstein, Murray & Borun

[57] ABSTRACT

The present invention relates to novel purified and isolated nucleotide sequences encoding mammalian $Ca^{2+}$/calmodulin stimulated phosphodiesterases (CaM-PDEs) and cyclic-GMP-stimulated phosphodiesterases (cGS-PDEs). Also provided are the corresponding recombinant expression products of said nucleotide sequences, immunological reagents specifically reactive therewith, and procedures for identifying compounds which modulate the enzymatic activity of such expression products.

25 Claims, 3 Drawing Sheets

PUBLICATIONS

Kincaid et al., "Differential Localization of Calmodulin–Dependent Enzymes in Rat Brain: Evidence for Selective Expression of Cyclic Nucleotide Phosphodiesterase in Specific Neurons", *Proc. Nat'l. Acad. Sci. (USA)*, 84:1118–1122 (1987).

Kozak, "The Scanning Model for Translation: An Update", *J. Cell. Biol.*, 108:229–241 (1989).

Krinks et al., "Reversible and Irreversible Activation of Cyclic Nucleotide Phosphodiesterase: Separation of the Regulatory and Catalytic Domains by Limited Proteolysis", *Advances in Cyclic Nuleotide and Protein Phosphorylation Research*, 16:31–47 (1984).

LaPorte et al., "Cross–Linking of Iodine–125–Labeled, Calcium–Dependent Regulatory Protein to the $Ca^{2+}$–Sensitive Phosphodiesterase Purified from Bovine Heart", *Biochemistry*, 18:2820–2825 (1979).

LeTrong et al., "Amino Acid Sequence of the Cyclic GMP Stimulated Cyclic Nucleotide Phosphodiesterase from Bovine Heart", *Biochemistry*, 29:10280–10288 (1990).

Livi et al., "Cloning and Expression of cDNA for a Human Low-$K_M$ Rolipram–Sensitive Cyclic AMP Phosphodiesterase", *Mol. Cell. Biol.*, 10;2678–2686 (1990).

Manganiello et al., "Cyclic GMP–Stimulated Cyclic Nucleotide Phosphodiesterases", pp. 62–85 in *Cyclic Nucleotide Phosphodiesterases: Structure, Regulation and Drug Action*, Beavo, J. and Houslay, M. D., Eds.: John Wiley & Sons, Ltd., New York (1990).

Maniatis et al., *Molecular Cloning: A Laboratory Manual*, pp. 326–328, Cold Spring Harbor Laboratory, Cold Spring Harbor, New York (1982).

Martins et al., "Purification and Characterization of a Cyclic GMP–Stimulated Cyclic Nucleotide Phosphodiesterase from Bovine Tissues", *J. Biol. Chem.*, 257:1973–1979 (1982).

Nikawa et al., "Cloning and Characterization of the Low–Affinity Cyclic AMP Phosphodiesterase Gene of *Saccaromyces cerevisiae*", *Mol. Cell. Biol.*, 7:3629–3636 (1987).

Nomenclature Committee of the International Union of Biochemistry (NCIUB), "Nomenclature for Incompletely Specified Bases in Nucleic Acid Sequences", *J. Biol. Chem.*, 261:13–17 (1986).

Novack et al., "Sequence Comparison of the 63–, 61–and 59–kDa Calmodulin–Dependent Cyclic Nucleotide Phosphodiesterases", *Biochemistry*, 30:7940–7947 (1991).

Ovchinnikov et al., "Cyclic GMP Phosphodiesterase from Bovine Retina", *FEBS*, 223:169–173 (1987).

Sanger et al., "DNA Sequencing with Chain–Terminating Inhibitors", *Proc. Nat'l. Acad. Sci. (USA)*, 74:5463–5467 (1977).

Sass et al., "Cloning and Characterization of the High–Affinity cAMP Phosphodiesterase of *Saccromyces cerevisiae*", *Proc. Nat'l. Acad. Sci. (USA)*, 83:9303–9307 (1986).

Seed, "An LFA–3 cDNA encodes a Phospholipid–Linked Membrane Protein Homologous to Its Receptor CD2", *Nature*, 329:840–843 (1987).

Sharma et al., "Demonstration of Bovine Brain Calmodulin–Dependent Cyclic Nucleotide Phosphodiesterase Isozymes by Monoclonal Antibodies", *J. Biol. Chem.*, 259:9248–9254 (1984).

Sharma et al., "Differential Regulation of Bovine Brain Calmodulin–Dependent Cyclic Nucleotide Phosphodiesterase Isozymes by Cyclic AMP–Dependent Protein Kinase and Calmodulin–Dependent Phosphatase", *Proc. Nat'l. Acad. Sci. (USA)*, 82:2603–2607 (1985).

Sharma et al., "Purification and Characterization of Bovine Lung Calmodulin–Dependent Cyclic Nucleotide Phosphodiesterase", *J. Biol. Chem.*, 261:14160–14166 (1986).

Sherman et al., *Methods in Yeast Genetics*, Cold Spring Harbor Laboratory, Cold Spring Harbor, New York (1986).

Short et al., "ZAP: A Bacteriophage γ Expression Vector with in vivo Excision Properties", *Nucleic Acids Res.*, 16:7583–7600 (1988).

Sonnenburg et al., "Molecular Cloning of a Cyclic GMP–Stimulated Cyclic Nucleotide Phosphodiesterase cDNA", *J. Biol. Chem.*, 266(26):17655–17661 (1991).

Stroop et al., "Direct Photolabeling of the cGMP–Stimulated Cyclic Nucleotide Phosphodiesterase", *J. Biol. Chem.*, 264:13718–13725 (1989).

Swinnen et al., "Molecular Cloning of Rat Homologues of the *Drosophila melanogaster* dunce cAMP Phosphodiesterase: Evidence for a Family of Genes", *Proc. Nat'l. Acad. Sci. (USA)*, 86:5325–5329 (1989).

Tanner et al., "Identification of the Phosphodiesterase Regulated by Muscarinic Chlinergic Receptors of the 1321N1 Human Astrocytoma Cells", *Mol. Pharmacol.*, 29:455–460 (1986).

Thompson et al., "Identification of Type II (Cyclic GMP–Stimulatable) Cyclic Nucleotide Phosphodiesterase (CNPDE) mRNA in Rat Pheochromocytoma Cells (PC12)", *FASEB J.*, 5(6):A1592 (Abstract No. 7092) (Mar. 1991).

Wang et al., "Calmodulin–Stimulated Cyclic Nucleotide Phosphodiesterases", pp. 19–59; in *Cyclic Nucleotide Phosphodiesterases: Structure, Regulation and Drug Action*, Beavo, J. and Houslay, M. D., Eds.: John Wiley & Sons, Ltd., New York (1990).

Watson et al., "An Alternative Procedure for the Synthesis of Double–Stranded cDNA for Cloning in Phage and Plasmid Vectors", pp. 79–88: in *DNA Cloning: A Practical Approach*, 1 (1985).

Wilson et al., "SRA5 Encodes the Low-$K_M$ Cyclic AMP Phosphodiesterase of *Saccharomyces cerevisiae*", *Mol. Cell. Biol.*, 8:505–510 (1988).

Broome, S. et al. *PNAS* 75(6):2746–2749 (1978).

Maniatis, T. et al. *Molecular Cloning: A Laboratory Manual*, 2nd ed., chapter 12 (1989).

Lee, C. C. *Science* 239:1288–1291 (1988).

Charbonneau, H. et al. *PNAS* 83:9308–9312 (1986).

```
              190       200       210       220       230       240
               |         |         |         |         |         |
59kDa: ELFTRYDLINRFKIPVsCLIAFAEALEVGysKYKNPYHNLIHAADVTQTVHYIMLHTGIM
61kDa: ELFTRYDLINRFKIPVSCLIAFAEALEVGYSKYKNPYHNLIHAADVTQTVHYIMLHTGIM
63kDa:                        KIPTVFLMTFLDALETGYGK 250       260       270       280       290       300
               |         |         |         |         |         |
59kDa: HWLTELEILAMVFAAAIHDYEHTGTTNNFHIQtrSDVAILYNQRSVLENHHVSAAYR---
61kDa: HWLTELEILAMVFAAAIHDYEHTGTTNNFHIQTRSDVAILYNQRSVLENHHVSAAYRLMQ
63kDa:                               kDETAILYNdRTVLEN 310       320       330       340       350       360
               |         |         |         |         |         |
59kDa: ---MNVLINLSKDDWRDLRNLVIEM-LST-------KNIRNSLQQPEGLDK-KTMSLI
61kDa: EEEMNVLINLSKDDWRDLRNLVIEMVLSTDMSGHFQQIKNIRNSLQQPEGLDKAKTMSLI
63kDa:                                       KTALQQLERIDK KALSLL
```

FIGURE 1B

```
                                    370         380         390         400         410         420
                                     -           -           -           -           -           -
59kDa:                              LHAADISHPAKSWKLHHRWTMALMEEFFLQGDKEAELGLPFSPLCDRKSTMVAQSQIGFI
61kDa:                              LHAADISHPAKSWKLHHRWTMALMEEFFLQGDKEAELGLPFSPLCDRKSTMVAQSQIGFI
63kDa:                              LHAADISHPTKQWSVHSRWTKALMEEFFRQGDK 430         440         450         460         470         480
                                     -           -           -           -           -           -
59kDa:                              DFIVEPTFSLLTDSTEKIIIPLIEEDSKTKTPSYGASRRSNMKGTTNDGTYSPDYSLASV
61kDa:                              DFIVEPTFSLLTDSTEKIIIPLIEEDSKTKTPSYGASRRSNMKGTTNDGTYSPDYSLASV
63kDa:

490         500         510         520         529
                                     -           -           -           -           -
59kDa:                              DLKSFKNSLVDIIQQNKERWKELAAQGEPDPHKNSDLVNAEEKHAETHS
61kDa:                              DLKSFKNSLVDIIQQNKERWKELAAQGEPDPHKNSDLVNAEEKHAETHS
63kDa:
```

FIGURE 1C

SEQUENCE LISTING ( 1 ) GENERAL INFORMATION:

( i i i ) NUMBER OF SEQUENCES: 58

( 2 ) INFORMATION FOR SEQ ID NO:1:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:1:

AARATGGGNA TGAARAARAA 20

( 2 ) INFORMATION FOR SEQ ID NO:2:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:2:

Lys Met Gly Met Met Lys Lys Lys
 1               5

( 2 ) INFORMATION FOR SEQ ID NO:3:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:3:

ACRTTCATYT CYTCYTCYTG CAT 23

( 2 ) INFORMATION FOR SEQ ID NO:4:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:4:

Met Gln Glu Glu Glu Met Asn Val
 1               5

( 2 ) INFORMATION FOR SEQ ID NO:5:

( i ) SEQUENCE CHARACTERISTICS:
    ( A ) LENGTH: 2291 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS (B) LOCATION: 100..1689

(xi) SEQUENCE DESCRIPTION: SEQ ID NO:5:

```
GGCTCAGAAA CTGTAGGAAT TCTGATGTGC TTCGGTGCAT GGAACAGTAA CAGATGAGCT                60

GCTTTGGGGA GAGCTGGAAC GCTCAGTCGG AGTATCATC ATG GGG TCT ACT GCT                 114
                                            Met Gly Ser Thr Ala
                                             1               5

ACA GAA ACT GAA GAA CTG GAA AAC ACT ACT TTT AAG TAT CTC ATT GGA                 162
Thr Glu Thr Glu Glu Leu Glu Asn Thr Thr Phe Lys Tyr Leu Ile Gly
                 10                  15                  20

GAA CAG ACT GAA AAA ATG TGG CAA CGC CTG AAA GGA ATA CTA AGA TGC                 210
Glu Gln Thr Glu Lys Met Trp Gln Arg Leu Lys Gly Ile Leu Arg Cys
             25                  30                  35

TTA GTG AAG CAG CTG GAA AAA GGT GAT GTT AAC GTC ATC GAC TTA AAG                 258
Leu Val Lys Gln Leu Glu Lys Gly Asp Val Asn Val Ile Asp Leu Lys
         40                  45                  50

AAG AAT ATT GAA TAT GCA GCA TCT GTG TTG GAA GCA GTT TAT ATT GAT                 306
Lys Asn Ile Glu Tyr Ala Ala Ser Val Leu Glu Ala Val Tyr Ile Asp
     55                  60                  65

GAA ACA AGG AGA CTG CTG GAC ACC GAT GAT GAG CTC AGT GAC ATT CAG                 354
Glu Thr Arg Arg Leu Leu Asp Thr Asp Asp Glu Leu Ser Asp Ile Gln
 70                  75                  80                  85

TCG GAT TCC GTC CCA TCA GAA GTC CGG GAC TGG TTG GCT TCT ACC TTT                 402
Ser Asp Ser Val Pro Ser Glu Val Arg Asp Trp Leu Ala Ser Thr Phe
                 90                  95                 100

ACA CGG AAA ATG GGG ATG ATG AAA AAG AAA TCT GAG GAA AAA CCA AGA                 450
Thr Arg Lys Met Gly Met Met Lys Lys Lys Ser Glu Glu Lys Pro Arg
             105                 110                 115

TTT CGG AGC ATT GTG CAT GTT GTT CAA GCT GGA ATT TTT GTG GAA AGA                 498
Phe Arg Ser Ile Val His Val Val Gln Ala Gly Ile Phe Val Glu Arg
         120                 125                 130

ATG TAC AGA AAG TCC TAT CAC ATG GTT GGC TTG GCA TAT CCA GAG GCT                 546
Met Tyr Arg Lys Ser Tyr His Met Val Gly Leu Ala Tyr Pro Glu Ala
     135                 140                 145

GTC ATA GTA ACA TTA AAG GAT GTT GAT AAA TGG TCT TTT GAT GTA TTT                 594
Val Ile Val Thr Leu Lys Asp Val Asp Lys Trp Ser Phe Asp Val Phe
150                 155                 160                 165

GCC TTG AAT GAA GCA AGT GGA GAA CAC AGT CTG AAG TTT ATG ATT TAT                 642
Ala Leu Asn Glu Ala Ser Gly Glu His Ser Leu Lys Phe Met Ile Tyr
                 170                 175                 180

GAA CTA TTC ACC AGA TAT GAT CTT ATC AAC CGT TTC AAG ATT CCT GTT                 690
Glu Leu Phe Thr Arg Tyr Asp Leu Ile Asn Arg Phe Lys Ile Pro Val
             185                 190                 195

TCT TGC CTA ATT GCC TTT GCA GAA GCT CTA GAA GTT GGT TAC AGC AAG                 738
Ser Cys Leu Ile Ala Phe Ala Glu Ala Leu Glu Val Gly Tyr Ser Lys
         200                 205                 210

TAC AAA AAT CCA TAC CAC AAT TTG ATT CAT GCA GCT GAT GTC ACT CAA                 786
Tyr Lys Asn Pro Tyr His Asn Leu Ile His Ala Ala Asp Val Thr Gln
     215                 220                 225

ACT GTG CAT TAC ATA ATG CTT CAT ACA GGT ATC ATG CAC TGG CTC ACT                 834
Thr Val His Tyr Ile Met Leu His Thr Gly Ile Met His Trp Leu Thr
230                 235                 240                 245

GAA CTG GAA ATT TTA GCA ATG GTC TTT GCC GCT GCC ATT CAT GAC TAT                 882
Glu Leu Glu Ile Leu Ala Met Val Phe Ala Ala Ala Ile His Asp Tyr
                 250                 255                 260

GAG CAT ACA GGG ACT ACA AAC AAT TTT CAC ATT CAG ACA AGG TCA GAT                 930
Glu His Thr Gly Thr Thr Asn Asn Phe His Ile Gln Thr Arg Ser Asp
             265                 270                 275

GTT GCC ATT TTG TAT AAT GAT CGC TCT GTC CTT GAA AAT CAT CAT GTG                 978
Val Ala Ile Leu Tyr Asn Asp Arg Ser Val Leu Glu Asn His His Val
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 280 |     |     |     |     |     | 285 |     |     |     |     |     | 290 |     |      |
| AGT | GCA | GCT | TAT | CGC | CTT | ATG | CAA | GAA | GAA | GAA | ATG | AAT | GTC | CTG | ATA | 1026 |
| Ser | Ala | Ala | Tyr | Arg | Leu | Met | Gln | Glu | Glu | Glu | Met | Asn | Val | Leu | Ile |      |
|     | 295 |     |     |     |     | 300 |     |     |     |     | 305 |     |     |     |     |      |
| AAT | TTA | TCC | AAA | GAT | GAC | TGG | AGG | GAT | CTT | CGG | AAC | CTA | GTG | ATT | GAA | 1074 |
| Asn | Leu | Ser | Lys | Asp | Asp | Trp | Arg | Asp | Leu | Arg | Asn | Leu | Val | Ile | Glu |      |
| 310 |     |     |     |     | 315 |     |     |     |     | 320 |     |     |     |     | 325 |      |
| ATG | GTG | TTG | TCT | ACA | GAC | ATG | TCG | GGT | CAC | TTC | CAG | CAA | ATT | AAA | AAT | 1122 |
| Met | Val | Leu | Ser | Thr | Asp | Met | Ser | Gly | His | Phe | Gln | Gln | Ile | Lys | Asn |      |
|     |     |     |     | 330 |     |     |     |     | 335 |     |     |     |     | 340 |     |      |
| ATA | AGA | AAT | AGT | TTG | CAG | CAA | CCT | GAA | GGG | CTT | GAC | AAA | GCC | AAA | ACC | 1170 |
| Ile | Arg | Asn | Ser | Leu | Gln | Gln | Pro | Glu | Gly | Leu | Asp | Lys | Ala | Lys | Thr |      |
|     |     |     | 345 |     |     |     |     | 350 |     |     |     |     | 355 |     |     |      |
| ATG | TCC | CTG | ATT | CTC | CAT | GCA | GCA | GAC | ATC | AGT | CAC | CCA | GCC | AAA | TCC | 1218 |
| Met | Ser | Leu | Ile | Leu | His | Ala | Ala | Asp | Ile | Ser | His | Pro | Ala | Lys | Ser |      |
|     |     | 360 |     |     |     |     | 365 |     |     |     |     | 370 |     |     |     |      |
| TGG | AAG | CTG | CAC | CAC | CGA | TGG | ACC | ATG | GCC | CTA | ATG | GAG | GAG | TTT | TTC | 1266 |
| Trp | Lys | Leu | His | His | Arg | Trp | Thr | Met | Ala | Leu | Met | Glu | Glu | Phe | Phe |      |
|     | 375 |     |     |     |     | 380 |     |     |     |     | 385 |     |     |     |     |      |
| CTA | CAG | GGA | GAT | AAA | GAA | GCT | GAA | TTA | GGG | CTT | CCA | TTT | TCC | CCG | CTT | 1314 |
| Leu | Gln | Gly | Asp | Lys | Glu | Ala | Glu | Leu | Gly | Leu | Pro | Phe | Ser | Pro | Leu |      |
| 390 |     |     |     |     | 395 |     |     |     |     | 400 |     |     |     |     | 405 |      |
| TGC | GAT | CGG | AAG | TCA | ACG | ATG | GTG | GCC | CAG | TCC | CAA | ATA | GGT | TTC | ATT | 1362 |
| Cys | Asp | Arg | Lys | Ser | Thr | Met | Val | Ala | Gln | Ser | Gln | Ile | Gly | Phe | Ile |      |
|     |     |     |     | 410 |     |     |     |     | 415 |     |     |     |     | 420 |     |      |
| GAT | TTC | ATA | GTA | GAA | CCA | ACA | TTT | TCT | CTT | CTG | ACA | GAC | TCA | ACA | GAG | 1410 |
| Asp | Phe | Ile | Val | Glu | Pro | Thr | Phe | Ser | Leu | Leu | Thr | Asp | Ser | Thr | Glu |      |
|     |     |     | 425 |     |     |     |     | 430 |     |     |     |     | 435 |     |     |      |
| AAA | ATT | ATT | ATT | CCT | CTT | ATA | GAG | GAA | GAC | TCG | AAA | ACC | AAA | ACT | CCT | 1458 |
| Lys | Ile | Ile | Ile | Pro | Leu | Ile | Glu | Glu | Asp | Ser | Lys | Thr | Lys | Thr | Pro |      |
|     |     | 440 |     |     |     |     | 445 |     |     |     |     | 450 |     |     |     |      |
| TCC | TAT | GGA | GCA | AGC | AGA | CGA | TCA | AAT | ATG | AAA | GGC | ACC | ACC | AAT | GAT | 1506 |
| Ser | Tyr | Gly | Ala | Ser | Arg | Arg | Ser | Asn | Met | Lys | Gly | Thr | Thr | Asn | Asp |      |
|     | 455 |     |     |     |     | 460 |     |     |     |     | 465 |     |     |     |     |      |
| GGA | ACC | TAC | TCC | CCC | GAC | TAC | TCC | CTT | GCC | AGC | GTG | GAC | CTG | AAG | AGC | 1554 |
| Gly | Thr | Tyr | Ser | Pro | Asp | Tyr | Ser | Leu | Ala | Ser | Val | Asp | Leu | Lys | Ser |      |
| 470 |     |     |     |     | 475 |     |     |     |     | 480 |     |     |     |     | 485 |      |
| TTC | AAA | AAC | AGC | CTG | GTG | GAC | ATC | ATC | CAG | CAG | AAC | AAA | GAG | AGG | TGG | 1602 |
| Phe | Lys | Asn | Ser | Leu | Val | Asp | Ile | Ile | Gln | Gln | Asn | Lys | Glu | Arg | Trp |      |
|     |     |     |     | 490 |     |     |     |     | 495 |     |     |     |     | 500 |     |      |
| AAA | GAG | TTA | GCT | GCT | CAA | GGT | GAA | CCT | GAT | CCC | CAT | AAG | AAC | TCA | GAT | 1650 |
| Lys | Glu | Leu | Ala | Ala | Gln | Gly | Glu | Pro | Asp | Pro | His | Lys | Asn | Ser | Asp |      |
|     |     |     | 505 |     |     |     |     | 510 |     |     |     |     | 515 |     |     |      |
| CTA | GTA | AAT | GCT | GAA | GAA | AAA | CAT | GCT | GAA | ACA | CAT | TCA | TAGGTCTGAA |  |  | 1699 |
| Leu | Val | Asn | Ala | Glu | Glu | Lys | His | Ala | Glu | Thr | His | Ser |     |     |     |      |
|     |     | 520 |     |     |     |     | 525 |     |     |     | 530 |     |     |     |     |      |

| | |
|---|---|
| ACACCTGAAA GACGTCTTTC ATTCTAAGGA TGGGAGGAAA CAAATTCACA AGAAATCATG | 1759 |
| AAGACATATA AAAGCTACAT ATGCATAAAA AACTCTGAAT TCAGGTCCCC ATGGCTGTCA | 1819 |
| CAAATGAATG AACAGAACTC CCAACCCCGC CTTTTTTTAA TATAATGAAA GTGCCTTAGC | 1879 |
| ATGGTTGCAG CTGTCACCAC TACAGTGTTT TACAGACGGT TTCTACTGAG CATCACAATA | 1939 |
| AAGAGAATCT TGCATTACAA AAAAAAGAAA AAAATGTGGC TCGCTTTTAA GATGAAGCAT | 1999 |
| TTCCCAGTAT TTCTGAGTCA GTTGTAAGAT TCTTTAATCG ATACTAATAG TTTCACTAAT | 2059 |
| AGCCACTGTC AGTGTCACGC ACTGTGATGA ATCTTATAC TTAGTCCTTC AACAGTTCCA | 2119 |
| GAGTTGTGAC TGTGCTTAAT AGTTTGCATA TGAATTCTGG ATAGAAATCA AATCACAAAC | 2179 |
| TGCATAGAAA TTTTAAAAAC CAGCTCCATA TTAAATTTTT TTAAGATATT GTCTTGTATT | 2239 |

GAAACTCCAA TACTTTGGCC ACCTGATGCA AAGAGCTGAC TCATTTGAAA CC 2291

( 2 ) INFORMATION FOR SEQ ID NO:6:

( i ) SEQUENCE CHARACTERISTICS:
        ( A ) LENGTH: 530 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Gly | Ser | Thr | Ala | Thr | Glu | Thr | Glu | Leu | Glu | Asn | Thr | Thr | Phe |
|---|---|---|---|---|---|---|---|---|---|---|---|---|---|---|
| 1 | | | | 5 | | | | 10 | | | | | 15 | |
| Lys | Tyr | Leu | Ile | Gly | Glu | Gln | Thr | Glu | Lys | Met | Trp | Gln | Arg | Leu | Lys |
| | | | 20 | | | | | 25 | | | | | 30 | |
| Gly | Ile | Leu | Arg | Cys | Leu | Val | Lys | Gln | Leu | Glu | Lys | Gly | Asp | Val | Asn |
| | | 35 | | | | 40 | | | | | 45 | | | |
| Val | Ile | Asp | Leu | Lys | Lys | Asn | Ile | Glu | Tyr | Ala | Ala | Ser | Val | Leu | Glu |
| | 50 | | | | 55 | | | | | 60 | | | | |
| Ala | Val | Tyr | Ile | Asp | Glu | Thr | Arg | Arg | Leu | Leu | Asp | Thr | Asp | Asp | Glu |
| 65 | | | | 70 | | | | 75 | | | | | 80 | |
| Leu | Ser | Asp | Ile | Gln | Ser | Asp | Ser | Val | Pro | Ser | Glu | Val | Arg | Asp | Trp |
| | | | 85 | | | | 90 | | | | | 95 | | |
| Leu | Ala | Ser | Thr | Phe | Thr | Arg | Lys | Met | Gly | Met | Met | Lys | Lys | Lys | Ser |
| | | | 100 | | | | 105 | | | | | 110 | | |
| Glu | Glu | Lys | Pro | Arg | Phe | Arg | Ser | Ile | Val | His | Val | Gln | Ala | Gly |
| | | 115 | | | | 120 | | | | | 125 | | | |
| Ile | Phe | Val | Glu | Arg | Met | Tyr | Arg | Lys | Ser | Tyr | His | Met | Val | Gly | Leu |
| | 130 | | | | 135 | | | | | 140 | | | | |
| Ala | Tyr | Pro | Glu | Ala | Val | Ile | Val | Thr | Leu | Lys | Asp | Val | Asp | Lys | Trp |
| 145 | | | | 150 | | | | 155 | | | | | 160 | |
| Ser | Phe | Asp | Val | Phe | Ala | Leu | Asn | Glu | Ala | Ser | Gly | Glu | His | Ser | Leu |
| | | | 165 | | | | 170 | | | | | 175 | | |
| Lys | Phe | Met | Ile | Tyr | Glu | Leu | Phe | Thr | Arg | Tyr | Asp | Leu | Ile | Asn | Arg |
| | | 180 | | | | 185 | | | | | 190 | | | |
| Phe | Lys | Ile | Pro | Val | Ser | Cys | Leu | Ile | Ala | Phe | Ala | Glu | Ala | Leu | Glu |
| | | 195 | | | | 200 | | | | | 205 | | | |
| Val | Gly | Tyr | Ser | Lys | Tyr | Lys | Asn | Pro | Tyr | His | Asn | Leu | Ile | His | Ala |
| | 210 | | | | 215 | | | | | 220 | | | | |
| Ala | Asp | Val | Thr | Gln | Thr | Val | His | Tyr | Ile | Met | Leu | His | Thr | Gly | Ile |
| 225 | | | | 230 | | | | 235 | | | | | 240 | |
| Met | His | Trp | Leu | Thr | Glu | Leu | Glu | Ile | Leu | Ala | Met | Val | Phe | Ala | Ala |
| | | | 245 | | | | 250 | | | | | 255 | | |
| Ala | Ile | His | Asp | Tyr | Glu | His | Thr | Gly | Thr | Thr | Asn | Asn | Phe | His | Ile |
| | | 260 | | | | 265 | | | | | 270 | | | |
| Gln | Thr | Arg | Ser | Asp | Val | Ala | Ile | Leu | Tyr | Asn | Asp | Arg | Ser | Val | Leu |
| | | 275 | | | | 280 | | | | | 285 | | | |
| Glu | Asn | His | His | Val | Ser | Ala | Ala | Tyr | Arg | Leu | Met | Gln | Glu | Glu | Glu |
| | | 290 | | | | 295 | | | | | 300 | | | |
| Met | Asn | Val | Leu | Ile | Asn | Leu | Ser | Lys | Asp | Asp | Trp | Arg | Asp | Leu | Arg |
| 305 | | | | 310 | | | | 315 | | | | | 320 | |
| Asn | Leu | Val | Ile | Glu | Met | Val | Leu | Ser | Thr | Asp | Met | Ser | Gly | His | Phe |
| | | | 325 | | | | 330 | | | | | 335 | | |
| Gln | Gln | Ile | Lys | Asn | Ile | Arg | Asn | Ser | Leu | Gln | Gln | Pro | Glu | Gly | Leu |
| | | | 340 | | | | 345 | | | | | 350 | | |

```
Asp  Lys  Ala  Lys  Thr  Met  Ser  Leu  Ile  Leu  His  Ala  Ala  Asp  Ile  Ser
          355                 360                           365
His  Pro  Ala  Lys  Ser  Trp  Lys  Leu  His  His  Arg  Trp  Thr  Met  Ala  Leu
          370                 375                           380
Met  Glu  Glu  Phe  Phe  Leu  Gln  Gly  Asp  Lys  Glu  Ala  Glu  Leu  Gly  Leu
385                      390                 395                           400
Pro  Phe  Ser  Pro  Leu  Cys  Asp  Arg  Lys  Ser  Thr  Met  Val  Ala  Gln  Ser
               405                      410                      415
Gln  Ile  Gly  Phe  Ile  Asp  Phe  Ile  Val  Glu  Pro  Thr  Phe  Ser  Leu  Leu
               420                 425                           430
Thr  Asp  Ser  Thr  Glu  Lys  Ile  Ile  Ile  Pro  Leu  Ile  Glu  Glu  Asp  Ser
          435                 440                           445
Lys  Thr  Lys  Thr  Pro  Ser  Tyr  Gly  Ala  Ser  Arg  Arg  Ser  Asn  Met  Lys
450                      455                      460
Gly  Thr  Thr  Asn  Asp  Gly  Thr  Tyr  Ser  Pro  Asp  Tyr  Ser  Leu  Ala  Ser
465                      470                 475                           480
Val  Asp  Leu  Lys  Ser  Phe  Lys  Asn  Ser  Leu  Val  Asp  Ile  Ile  Gln  Gln
               485                 490                           495
Asn  Lys  Glu  Arg  Trp  Lys  Glu  Leu  Ala  Ala  Gln  Gly  Glu  Pro  Asp  Pro
               500                 505                           510
His  Lys  Asn  Ser  Asp  Leu  Val  Asn  Ala  Glu  Glu  Lys  His  Ala  Glu  Thr
          515                 520                           525
His  Ser
530
```

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Met  Asp  Asp  His  Val  Thr  Ile
1                   5
```

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

ATGAGRAGRC AYGTHACNAT                      20

( 2 ) INFORMATION FOR SEQ ID NO:9:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
Leu  Arg  Cys  Leu  Val  Lys  Gln
1                   5
```

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i v ) ANTI-SENSE: YES ( x i ) SEQUENCE DESCRIPTION: SEQ ID NO:10:

CTGCTTCACT AAGCATCTTA G        21

( 2 ) INFORMATION FOR SEQ ID NO:11:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

ATGAGAAGGC ACGTAACGAT CAGGAGGAAA CATCTCCAAA GACCCATCTT TAGACTAAGA    60

TGCTTAGTGA AGCAG        75

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

ATGGAYGAYC ACGTAACGAT C        21

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i v ) ANTI-SENSE: YES ( x i ) SEQUENCE DESCRIPTION: SEQ ID NO:13:

AAGTATCTCA TTGGAGAACA G        21

( 2 ) INFORMATION FOR SEQ ID NO:14:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

ATGGATGATC ACGTAACGAT CAGGAGGAAA CATCTCCAAA GACCCATCTT TAGA    54

( 2 ) INFORMATION FOR SEQ ID NO:15:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

Met Asp Asp His Val Thr Ile Arg Arg Lys His Leu Gln Arg Pro Ile
 1               5                  10                  15
Phe Arg ( 2 ) INFORMATION FOR SEQ ID NO:16:

( i ) SEQUENCE CHARACTERISTICS:
        ( A ) LENGTH: 2656 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 136..1677

( x i ) SEQUENCE DESCRIPTION: SEQ ID NO:16:

TTGCTGTCGA GAGAAAGAGG AAACTACTTT TGCCTTCTGG GCTCCTTGCA GGACAATAGA    60

TCAGGATAAG CTTCCACATT CTCTCCCTGG ATTTCTGGAG TGGTTTCCAG GAACAAGCTA    120

AACTTTCACC TTTAA ATG GAT GAC CAT GTC ACA ATC AGG AGG AAA CAT CTC    171
              Met Asp Asp His Val Thr Ile Arg Arg Lys His Leu
               1               5                  10

CAA AGA CCC ATC TTT AGA CTA AGA TGC TTA GTG AAG CAG CTG GAA AAA    219
Gln Arg Pro Ile Phe Arg Leu Arg Cys Leu Val Lys Gln Leu Glu Lys
         15                  20                  25

GGT GAT GTT AAC GTC ATC GAC TTA AAG AAG AAT ATT GAA TAT GCA GCA    267
Gly Asp Val Asn Val Ile Asp Leu Lys Lys Asn Ile Glu Tyr Ala Ala
     30                  35                  40

TCT GTG TTG GAA GCA GTT TAT ATT GAT GAA ACA AGG AGA CTG CTG GAC    315
Ser Val Leu Glu Ala Val Tyr Ile Asp Glu Thr Arg Arg Leu Leu Asp
 45                  50                  55                  60

ACC GAT GAT GAG CTC AGT GAC ATT CAG TCG GAT TCC GTC CCA TCA GAA    363
Thr Asp Asp Glu Leu Ser Asp Ile Gln Ser Asp Ser Val Pro Ser Glu
                 65                  70                  75

GTC CGG GAC TGG TTG GCT TCT ACC TTT ACA CGG AAA ATG GGG ATG ATG    411
Val Arg Asp Trp Leu Ala Ser Thr Phe Thr Arg Lys Met Gly Met Met
             80                  85                  90

AAA AAG AAA TCT GAG GAA AAA CCA AGA TTT CGG AGC ATT GTG CAT GTT    459
Lys Lys Lys Ser Glu Glu Lys Pro Arg Phe Arg Ser Ile Val His Val
         95                  100                 105

GTT CAA GCT GGA ATT TTT GTG GAA AGA ATG TAC AGA AAG TCC TAT CAC    507
Val Gln Ala Gly Ile Phe Val Glu Arg Met Tyr Arg Lys Ser Tyr His
     110                 115                 120

ATG GTT GGC TTG GCA TAT CCA GAG GCT GTC ATA GTA ACA TTA AAG GAT    555
Met Val Gly Leu Ala Tyr Pro Glu Ala Val Ile Val Thr Leu Lys Asp
125                 130                 135                 140

GTT GAT AAA TGG TCT TTT GAT GTA TTT GCC TTG AAT GAA GCA AGT GGA    603
Val Asp Lys Trp Ser Phe Asp Val Phe Ala Leu Asn Glu Ala Ser Gly
                 145                 150                 155

| | | | | | | | | | | | | | | | | |
|---|---|---|---|---|---|---|---|---|---|---|---|---|---|---|---|---|
| GAA | CAC | AGT | CTG | AAG | TTT | ATG | ATT | TAT | GAA | CTA | TTC | ACC | AGA | TAT | GAT | 651 |
| Glu | His | Ser | Leu | Lys | Phe | Met | Ile | Tyr | Glu | Leu | Phe | Thr | Arg | Tyr | Asp | |
| | | | 160 | | | | 165 | | | | | 170 | | | | |
| CTT | ATC | AAC | CGT | TTC | AAG | ATT | CCT | GTT | TCT | TGC | CTA | ATT | GCC | TTT | GCA | 699 |
| Leu | Ile | Asn | Arg | Phe | Lys | Ile | Pro | Val | Ser | Cys | Leu | Ile | Ala | Phe | Ala | |
| | 175 | | | | | 180 | | | | | 185 | | | | | |
| GAA | GCT | CTA | GAA | GTT | GGT | TAC | AGC | AAG | TAC | AAA | AAT | CCA | TAC | CAC | AAT | 747 |
| Glu | Ala | Leu | Glu | Val | Gly | Tyr | Ser | Lys | Tyr | Lys | Asn | Pro | Tyr | His | Asn | |
| | 190 | | | | | 195 | | | | | 200 | | | | | |
| TTG | ATT | CAT | GCA | GCT | GAT | GTC | ACT | CAA | ACT | GTG | CAT | TAC | ATA | ATG | CTT | 795 |
| Leu | Ile | His | Ala | Ala | Asp | Val | Thr | Gln | Thr | Val | His | Tyr | Ile | Met | Leu | |
| 205 | | | | | 210 | | | | | 215 | | | | | 220 | |
| CAT | ACA | GGT | ATC | ATG | CAC | TGG | CTC | ACT | GAA | CTG | GAA | ATT | TTA | GCA | ATG | 843 |
| His | Thr | Gly | Ile | Met | His | Trp | Leu | Thr | Glu | Leu | Glu | Ile | Leu | Ala | Met | |
| | | | | 225 | | | | | 230 | | | | | 235 | | |
| GTC | TTT | GCC | GCT | GCC | ATT | CAT | GAC | TAT | GAG | CAT | ACA | GGG | ACT | ACA | AAC | 891 |
| Val | Phe | Ala | Ala | Ala | Ile | His | Asp | Tyr | Glu | His | Thr | Gly | Thr | Thr | Asn | |
| | | | 240 | | | | | 245 | | | | 250 | | | | |
| AAT | TTT | CAC | ATT | CAG | ACA | AGG | TCA | GAT | GTT | GCC | ATT | TTG | TAT | AAT | GAT | 939 |
| Asn | Phe | His | Ile | Gln | Thr | Arg | Ser | Asp | Val | Ala | Ile | Leu | Tyr | Asn | Asp | |
| | | 255 | | | | | 260 | | | | | 265 | | | | |
| CGC | TCT | GTC | CTT | GAA | AAT | CAT | CAT | GTG | AGT | GCA | GCT | TAT | CGC | CTT | ATG | 987 |
| Arg | Ser | Val | Leu | Glu | Asn | His | His | Val | Ser | Ala | Ala | Tyr | Arg | Leu | Met | |
| | 270 | | | | | 275 | | | | | 280 | | | | | |
| CAA | GAA | GAA | GAA | ATG | AAT | GTC | CTG | ATA | AAT | TTA | TCC | AAA | GAT | GAC | TGG | 1035 |
| Gln | Glu | Glu | Glu | Met | Asn | Val | Leu | Ile | Asn | Leu | Ser | Lys | Asp | Asp | Trp | |
| 285 | | | | | 290 | | | | | 295 | | | | | 300 | |
| AGG | GAT | CTT | CGG | AAC | CTA | GTG | ATT | GAA | ATG | GTG | TTG | TCT | ACA | GAC | ATG | 1083 |
| Arg | Asp | Leu | Arg | Asn | Leu | Val | Ile | Glu | Met | Val | Leu | Ser | Thr | Asp | Met | |
| | | | | 305 | | | | | 310 | | | | | 315 | | |
| TCG | GGT | CAC | TTC | CAG | CAA | ATT | AAA | AAT | ATA | AGA | AAT | AGT | TTG | CAG | CAA | 1131 |
| Ser | Gly | His | Phe | Gln | Gln | Ile | Lys | Asn | Ile | Arg | Asn | Ser | Leu | Gln | Gln | |
| | | | 320 | | | | | 325 | | | | | 330 | | | |
| CCT | GAA | GGG | CTT | GAC | AAA | GCC | AAA | ACC | ATG | TCC | CTG | ATT | CTC | CAT | GCA | 1179 |
| Pro | Glu | Gly | Leu | Asp | Lys | Ala | Lys | Thr | Met | Ser | Leu | Ile | Leu | His | Ala | |
| | | 335 | | | | | 340 | | | | | 345 | | | | |
| GCA | GAC | ATC | AGT | CAC | CCA | GCC | AAA | TCC | TGG | AAG | CTG | CAC | CAC | CGA | TGG | 1227 |
| Ala | Asp | Ile | Ser | His | Pro | Ala | Lys | Ser | Trp | Lys | Leu | His | His | Arg | Trp | |
| | 350 | | | | | 355 | | | | | 360 | | | | | |
| ACC | ATG | GCC | CTA | ATG | GAG | GAG | TTT | TTC | CTA | CAG | GGA | GAT | AAA | GAA | GCT | 1275 |
| Thr | Met | Ala | Leu | Met | Glu | Glu | Phe | Phe | Leu | Gln | Gly | Asp | Lys | Glu | Ala | |
| 365 | | | | | 370 | | | | | 375 | | | | | 380 | |
| GAA | TTA | GGG | CTT | CCA | TTT | TCC | CCG | CTT | TGC | GAT | CGG | AAG | TCA | ACG | ATG | 1323 |
| Glu | Leu | Gly | Leu | Pro | Phe | Ser | Pro | Leu | Cys | Asp | Arg | Lys | Ser | Thr | Met | |
| | | | | 385 | | | | | 390 | | | | | 395 | | |
| GTG | GCC | CAG | TCC | CAA | ATA | GGT | TTC | ATT | GAT | TTC | ATA | GTA | GAA | CCA | ACA | 1371 |
| Val | Ala | Gln | Ser | Gln | Ile | Gly | Phe | Ile | Asp | Phe | Ile | Val | Glu | Pro | Thr | |
| | | | 400 | | | | | 405 | | | | | 410 | | | |
| TTT | TCT | CTT | CTG | ACA | GAC | TCA | ACA | GAG | AAA | ATT | ATT | ATT | CCT | CTT | ATA | 1419 |
| Phe | Ser | Leu | Leu | Thr | Asp | Ser | Thr | Glu | Lys | Ile | Ile | Ile | Pro | Leu | Ile | |
| | | 415 | | | | | 420 | | | | | 425 | | | | |
| GAG | GAA | GAC | TCG | AAA | ACC | AAA | ACT | CCT | TCC | TAT | GGA | GCA | AGC | AGA | CGA | 1467 |
| Glu | Glu | Asp | Ser | Lys | Thr | Lys | Thr | Pro | Ser | Tyr | Gly | Ala | Ser | Arg | Arg | |
| | 430 | | | | | 435 | | | | | 440 | | | | | |
| TCA | AAT | ATG | AAA | GGC | ACC | ACC | AAT | GAT | GGA | ACC | TAC | TCC | CCC | GAC | TAC | 1515 |
| Ser | Asn | Met | Lys | Gly | Thr | Thr | Asn | Asp | Gly | Thr | Tyr | Ser | Pro | Asp | Tyr | |
| 445 | | | | | 450 | | | | | 455 | | | | | 460 | |
| TCC | CTT | GCC | AGC | GTG | GAC | CTG | AAG | AGC | TTC | AAA | AAC | AGC | CTG | GTG | GAC | 1563 |
| Ser | Leu | Ala | Ser | Val | Asp | Leu | Lys | Ser | Phe | Lys | Asn | Ser | Leu | Val | Asp | |
| | | | | 465 | | | | | 470 | | | | | 475 | | |

| | | | | | | | | | | | | | | | | |
|---|---|---|---|---|---|---|---|---|---|---|---|---|---|---|---|---|
| ATC | ATC | CAG | CAG | AAC | AAA | GAG | AGG | TGG | AAA | GAG | TTA | GCT | GCT | CAA | GGT | 1611 |
| Ile | Ile | Gln | Gln | Asn | Lys | Glu | Arg | Trp | Lys | Glu | Leu | Ala | Ala | Gln | Gly | |
| | | | 480 | | | | | 485 | | | | | | 490 | | |
| GAA | CCT | GAT | CCC | CAT | AAG | AAC | TCA | GAT | CTA | GTA | AAT | GCT | GAA | GAA | AAA | 1659 |
| Glu | Pro | Asp | Pro | His | Lys | Asn | Ser | Asp | Leu | Val | Asn | Ala | Glu | Glu | Lys | |
| | | 495 | | | | | 500 | | | | | 505 | | | | |
| CAT | GCT | GAA | ACA | CAT | TCA | TAGGTCTGAA | | ACACCTGAAA | | GACGTCTTTC | | | | | | 1707 |
| His | Ala | Glu | Thr | His | Ser | | | | | | | | | | | |
| | | 510 | | | | | | | | | | | | | | |

| | | | | | |
|---|---|---|---|---|---|
| ATTCTAAGGA | TGGGAGAGTG | CTGTAACTAC | AAAACTTTCA | AGCTTCTAAG | TAAAAGGAAA | 1767 |
| GCAAAAACAA | AATTACAGAA | AAATATTTTT | GCAGCTCTGA | GGCTATTTAG | ATTGTCCTTG | 1827 |
| TTGTTTTAAA | TACATGGGAA | CCAAGTGAGA | AGAGGGGCTG | CTCAGAAGTT | GTAGTCGAAG | 1887 |
| TCCTAAGACA | ACAATGAAGC | ATCAGAGCCC | TGACTCTGTG | ACCTGATGAA | CTCTTCGTTG | 1947 |
| TAACTCTCAA | GCTGGGAAAC | CACAGCGAAT | CCTGTTCCTG | AAAGCAGTGA | ACCAGCCTGC | 2007 |
| ATCCACCACT | GTTATTGCAA | AGCACGAAAG | CATCACCCAC | GTGGGGGTCA | TCACAATGCA | 2067 |
| AGTCACGCAA | GACCTATGAC | CAAGATGACA | AGAACCTCCA | GCCCTTGTTG | GAGACAGACA | 2127 |
| CTAGAACTGA | GAGTGGGATT | TGCCTTCTGG | GGTGTTAATC | CCATCAGGAT | GTAACAAAAT | 2187 |
| ATATTACAGG | TCAAGGGATA | AGGGACAAGA | AGTGTGTGTC | TGTGTGTGTG | TGTGTGTATG | 2247 |
| TGCGCGCACT | CAAAAATGTC | TGTGAAAATG | GAAGCCCACA | CTCTTCTGCA | CAGAGAGCAT | 2307 |
| TATTTGATGT | GATTTATAAT | TTTACTACAA | ACAAACGAAC | TGCAGCCATT | GGAGACTGCT | 2367 |
| TCCTTGTCAT | GTTTTGCCTG | AGCATGTGCA | GAGCCTTGCC | TTTGTTCCAA | ATTGAAGAAC | 2427 |
| TACCTTTATT | TGTTATTAGC | TGCCAAGAAA | GGTCAAGCCC | AAGTAGGTGT | TGTCATTTTC | 2487 |
| ACCGTACAAA | CTCTTCAATG | ATTGTTAGAC | TAAAGGAATT | TGTTTTGTG | AAAGGTAGAA | 2547 |
| ATTAGATGGA | AAAGATCAAG | AGTAGTCATC | AATTAAAGAA | GAAAGTGAAG | GTGGATATGT | 2607 |
| CCATCCTAAT | GAGTTTTCTG | TTGCACCTGC | TTCTTCCCTG | CGACAGCAA | | 2656 |

( 2 ) INFORMATION FOR SEQ ID NO:17:

( i ) SEQUENCE CHARACTERISTICS:
  ( A ) LENGTH: 514 amino acids
  ( B ) TYPE: amino acid
  ( D ) TOPOLOGY: linear ( i i ) MOLECULE TYPE: protein ( x i ) SEQUENCE DESCRIPTION: SEQ ID NO:17:

| | | | | | | | | | | | | | | |
|---|---|---|---|---|---|---|---|---|---|---|---|---|---|---|
| Met | Asp | Asp | His | Val | Thr | Ile | Arg | Arg | Lys | His | Leu | Gln | Arg | Pro | Ile |
| 1 | | | | 5 | | | | | 10 | | | | | 15 |
| Phe | Arg | Leu | Arg | Cys | Leu | Val | Lys | Gln | Leu | Glu | Lys | Gly | Asp | Val | Asn |
| | | | 20 | | | | | 25 | | | | | 30 | | |
| Val | Ile | Asp | Leu | Lys | Lys | Asn | Ile | Glu | Tyr | Ala | Ala | Ser | Val | Leu | Glu |
| | | 35 | | | | | 40 | | | | | 45 | | | |
| Ala | Val | Tyr | Ile | Asp | Glu | Thr | Arg | Arg | Leu | Leu | Asp | Thr | Asp | Asp | Glu |
| | 50 | | | | | 55 | | | | | 60 | | | | |
| Leu | Ser | Asp | Ile | Gln | Ser | Asp | Ser | Val | Pro | Ser | Glu | Val | Arg | Asp | Trp |
| 65 | | | | | 70 | | | | | 75 | | | | | 80 |
| Leu | Ala | Ser | Thr | Phe | Thr | Arg | Lys | Met | Gly | Met | Met | Lys | Lys | Lys | Ser |
| | | | | 85 | | | | | 90 | | | | | 95 | |
| Glu | Glu | Lys | Pro | Arg | Phe | Arg | Ser | Ile | Val | His | Val | Val | Gln | Ala | Gly |
| | | | 100 | | | | | 105 | | | | | 110 | | |
| Ile | Phe | Val | Glu | Arg | Met | Tyr | Arg | Lys | Ser | Tyr | His | Met | Val | Gly | Leu |
| | | 115 | | | | | 120 | | | | | 125 | | | |

| | | | | | | | | | | | | | |
|---|---|---|---|---|---|---|---|---|---|---|---|---|---|
| Ala | Tyr 130 | Pro | Glu | Ala | Val | Ile 135 | Val | Thr | Leu | Lys | Asp 140 | Val | Asp | Lys | Trp |
| Ser 145 | Phe | Asp | Val | Phe | Ala 150 | Leu | Asn | Glu | Ala | Ser 155 | Gly | Glu | His | Ser | Leu 160 |
| Lys | Phe | Met | Ile | Tyr 165 | Glu | Leu | Phe | Thr | Arg 170 | Tyr | Asp | Leu | Ile | Asn 175 | Arg |
| Phe | Lys | Ile | Pro 180 | Val | Ser | Cys | Leu | Ile 185 | Ala | Phe | Ala | Glu | Ala 190 | Leu | Glu |
| Val | Gly | Tyr 195 | Ser | Lys | Tyr | Lys | Asn 200 | Pro | Tyr | His | Asn | Leu 205 | Ile | His | Ala |
| Ala | Asp 210 | Val | Thr | Gln | Thr | Val 215 | His | Tyr | Ile | Met | Leu 220 | His | Thr | Gly | Ile |
| Met 225 | His | Trp | Leu | Thr | Glu 230 | Leu | Glu | Ile | Leu | Ala 235 | Met | Val | Phe | Ala | Ala 240 |
| Ala | Ile | His | Asp | Tyr 245 | Glu | His | Thr | Gly | Thr 250 | Thr | Asn | Asn | Phe | His 255 | Ile |
| Gln | Thr | Arg | Ser 260 | Asp | Val | Ala | Ile | Leu 265 | Tyr | Asn | Asp | Arg | Ser 270 | Val | Leu |
| Glu | Asn | His 275 | His | Val | Ser | Ala | Ala 280 | Tyr | Arg | Leu | Met | Gln 285 | Glu | Glu | Glu |
| Met | Asn 290 | Val | Leu | Ile | Asn | Leu 295 | Ser | Lys | Asp | Asp | Trp 300 | Arg | Asp | Leu | Arg |
| Asn 305 | Leu | Val | Ile | Glu | Met 310 | Val | Leu | Ser | Thr | Asp 315 | Met | Ser | Gly | His | Phe 320 |
| Gln | Gln | Ile | Lys | Asn 325 | Ile | Arg | Asn | Ser | Leu 330 | Gln | Gln | Pro | Glu | Gly 335 | Leu |
| Asp | Lys | Ala | Lys 340 | Thr | Met | Ser | Leu | Ile 345 | Leu | His | Ala | Ala | Asp 350 | Ile | Ser |
| His | Pro | Ala 355 | Lys | Ser | Trp | Lys | Leu 360 | His | His | Arg | Trp | Thr 365 | Met | Ala | Leu |
| Met | Glu 370 | Glu | Phe | Phe | Leu | Gln 375 | Gly | Asp | Lys | Glu | Ala 380 | Glu | Leu | Gly | Leu |
| Pro 385 | Phe | Ser | Pro | Leu | Cys 390 | Asp | Arg | Lys | Ser | Thr 395 | Met | Val | Ala | Gln | Ser 400 |
| Gln | Ile | Gly | Phe | Ile 405 | Asp | Phe | Ile | Val | Glu 410 | Pro | Thr | Phe | Ser | Leu 415 | Leu |
| Thr | Asp | Ser | Thr 420 | Glu | Lys | Ile | Ile | Ile 425 | Pro | Leu | Ile | Glu | Glu 430 | Asp | Ser |
| Lys | Thr | Lys 435 | Thr | Pro | Ser | Tyr | Gly 440 | Ala | Ser | Arg | Arg | Ser 445 | Asn | Met | Lys |
| Gly | Thr 450 | Thr | Asn | Asp | Gly | Thr 455 | Tyr | Ser | Pro | Asp | Tyr 460 | Ser | Leu | Ala | Ser |
| Val 465 | Asp | Leu | Lys | Ser | Phe 470 | Lys | Asn | Ser | Leu | Val 475 | Asp | Ile | Ile | Gln | Gln 480 |
| Asn | Lys | Glu | Arg | Trp 485 | Lys | Glu | Leu | Ala | Ala 490 | Gln | Gly | Glu | Pro | Asp 495 | Pro |
| His | Lys | Asn | Ser 500 | Asp | Leu | Val | Asn | Ala 505 | Glu | Glu | Lys | His | Ala 510 | Glu | Thr |
| His | Ser | | | | | | | | | | | | | | |

( 2 ) INFORMATION FOR SEQ ID NO:18:

( i ) SEQUENCE CHARACTERISTICS:
        ( A ) LENGTH: 23 base pairs
        ( B ) TYPE: nucleic acid

51

-continued ( C ) STRANDEDNESS: single
( D ) TOPOLOGY: linear ( i i ) MOLECULE TYPE: DNA ( x i ) SEQUENCE DESCRIPTION: SEQ ID NO:18:

ATHCAYGAYT AYGARCAYAC NGG                                                23

( 2 ) INFORMATION FOR SEQ ID NO:19:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( x i ) SEQUENCE DESCRIPTION: SEQ ID NO:19:

Ile His Asp Tyr Glu His Thr Gly
1               5

( 2 ) INFORMATION FOR SEQ ID NO:20:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:20:

TCYTTRTCNC CYTGNCGRAA RAAYTCYTCC AT                                       32

( 2 ) INFORMATION FOR SEQ ID NO:21:

( i ) SEQUENCE CHARACTERISTICS:
( A ) LENGTH: 11 amino acids
( B ) TYPE: amino acid
( D ) TOPOLOGY: linear ( i i ) MOLECULE TYPE: peptide ( x i ) SEQUENCE DESCRIPTION: SEQ ID NO:21:

Met Glu Glu Phe Phe Arg Gln Gly Asp Lys Glu
1               5                   10

( 2 ) INFORMATION FOR SEQ ID NO:22:

( i ) SEQUENCE CHARACTERISTICS:
( A ) LENGTH: 412 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 1..412

( x i ) SEQUENCE DESCRIPTION: SEQ ID NO:22:

```
ATT CAT GAT TAT AAC ACA CGG GGC ACT ACC AAC AGC TTC CAC ATC CAG          48
Ile His Asp Tyr Asn Thr Arg Gly Thr Thr Asn Ser Phe His Ile Gln
1               5                   10                  15

ACC AAA TCG GAA TGC GCC ATC CTG TAC AAC GAC CGC TCA GTG CTG GAG          96
Thr Lys Ser Glu Cys Ala Ile Leu Tyr Asn Asp Arg Ser Val Leu Glu
            20                  25                  30

AAT CAC CAC ATC AGC TCG GTT TTC CGA ATG ATG CAG GAC GAC GAC ATG         144
```

| | | | | | | | | | | | | | | | |
|---|---|---|---|---|---|---|---|---|---|---|---|---|---|---|---|
|Asn|His|His 35|Ile|Ser|Ser|Val|Phe 40|Arg|Met|Met|Gln|Asp 45|Asp|Asp|Met|

AAC ATC TTC ATC AAC CTC ACC AAG GAT GAG TTT GTA GAG CTG CGG GCT    192
Asn Ile Phe Ile Asn Leu Thr Lys Asp Glu Phe Val Glu Leu Arg Ala
     50                  55              60

CTG GTC ATT GAG ATG GTG TTG GCC ACA GAC ATG TCC TGC CAT TTC CAG    240
Leu Val Ile Glu Met Val Leu Ala Thr Asp Met Ser Cys His Phe Gln
65           70                  75                           80

CAA GTG AAG TCC ATG AAG ACA GCC TTG CAG CAG CTG GAG AGG ATT GAC    288
Gln Val Lys Ser Met Lys Thr Ala Leu Gln Gln Leu Glu Arg Ile Asp
             85                  90                   95

AAG TCC AAG GCC CTC TCT CTG CTG CTT CAT GCT GCT GAC ATC AGC CAC    336
Lys Ser Lys Ala Leu Ser Leu Leu Leu His Ala Ala Asp Ile Ser His
             100             105                  110

CCC ACC AAG CAG TGG TCG GTT CAC AGC CGC TGG ACC AAG GCC CTC ATG    384
Pro Thr Lys Gln Trp Ser Val His Ser Arg Trp Thr Lys Ala Leu Met
             115             120                  125

GAG GAG TTC TTC CGA CAA GGG GAC AAA G                              412
Glu Glu Phe Phe Arg Gln Gly Asp Lys
130                 135

( 2 ) INFORMATION FOR SEQ ID NO:23:

( i ) SEQUENCE CHARACTERISTICS:
        ( A ) LENGTH: 137 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

Ile His Asp Tyr Asn Thr Arg Gly Thr Thr Asn Ser Phe His Ile Gln
1               5                   10                  15

Thr Lys Ser Glu Cys Ala Ile Leu Tyr Asn Asp Arg Ser Val Leu Glu
             20                  25                  30

Asn His His Ile Ser Ser Val Phe Arg Met Met Gln Asp Asp Asp Met
         35                  40                  45

Asn Ile Phe Ile Asn Leu Thr Lys Asp Glu Phe Val Glu Leu Arg Ala
     50                  55                  60

Leu Val Ile Glu Met Val Leu Ala Thr Asp Met Ser Cys His Phe Gln
65               70                  75                       80

Gln Val Lys Ser Met Lys Thr Ala Leu Gln Gln Leu Glu Arg Ile Asp
             85                  90                  95

Lys Ser Lys Ala Leu Ser Leu Leu Leu His Ala Ala Asp Ile Ser His
             100                 105                 110

Pro Thr Lys Gln Trp Ser Val His Ser Arg Trp Thr Lys Ala Leu Met
             115                 120                 125

Glu Glu Phe Phe Arg Gln Gly Asp Lys
130                 135

( 2 ) INFORMATION FOR SEQ ID NO:24:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:24:

AARAARAAYY TNGARTAYAC NGC    23

5,602,019

55                                                                              56
-continued ( 2 ) INFORMATION FOR SEQ ID NO:25:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

```
Lys  Lys  Asn  Leu  Glu  Tyr  Thr  Ala
 1                    5
```

( 2 ) INFORMATION FOR SEQ ID NO:26:

( i ) SEQUENCE CHARACTERISTICS:
        ( A ) LENGTH: 1844 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 114..1715

( x i ) SEQUENCE DESCRIPTION: SEQ ID NO:26:

```
GGCTGGGCAG  CGGGAAAGGA  GGAGCCGCAG  GAACTGCAGC  TCTGCCAGCT  TGGGCCGAGC                    60

TTTAGAGACC  CCCGGCCTGG  CTGGTCCCTG  CCAGCCGCAG  ACGGAGGCTG  AGC ATG                       116
                                                                 Met
                                                                  1

GAG  CTG  TCC  CCC  CGC  AGC  CCT  CCC  GAG  ATG  CTA  GAG  TCG  GAC  TGC  CCT           164
Glu  Leu  Ser  Pro  Arg  Ser  Pro  Pro  Glu  Met  Leu  Glu  Ser  Asp  Cys  Pro
               5                        10                       15

TCA  CCC  CTG  GAG  CTG  AAG  TCA  GCC  CCC  AGC  AAG  AAG  ATG  TGG  ATT  AAG           212
Ser  Pro  Leu  Glu  Leu  Lys  Ser  Ala  Pro  Ser  Lys  Lys  Met  Trp  Ile  Lys
          20                        25                       30

CTC  CGG  TCT  CTG  CTG  CGC  TAC  ATG  GTG  AAG  CAG  TTG  GAG  AAC  GGG  GAG           260
Leu  Arg  Ser  Leu  Leu  Arg  Tyr  Met  Val  Lys  Gln  Leu  Glu  Asn  Gly  Glu
     35                        40                       45

GTA  AAC  ATT  GAG  GAG  CTG  AAG  AAA  AAC  CTG  GAG  TAC  ACA  GCT  TCT  CTG           308
Val  Asn  Ile  Glu  Glu  Leu  Lys  Lys  Asn  Leu  Glu  Tyr  Thr  Ala  Ser  Leu
 50                       55                       60                       65

CTG  GAG  GCC  GTC  TAT  ATA  GAT  GAG  ACT  CGG  CAA  ATC  CTG  GAC  ACG  GAG           356
Leu  Glu  Ala  Val  Tyr  Ile  Asp  Glu  Thr  Arg  Gln  Ile  Leu  Asp  Thr  Glu
                    70                       75                       80

GAT  GAG  CTG  CAG  GAG  CTG  CGG  TCT  GAT  GCG  GTG  CCT  TCA  GAG  GTG  CGG           404
Asp  Glu  Leu  Gln  Glu  Leu  Arg  Ser  Asp  Ala  Val  Pro  Ser  Glu  Val  Arg
               85                        90                       95

GAC  TGG  CTG  GCC  TCC  ACC  TTC  ACC  CAG  CAG  ACC  CGG  GCC  AAA  GGC  CCG           452
Asp  Trp  Leu  Ala  Ser  Thr  Phe  Thr  Gln  Gln  Thr  Arg  Ala  Lys  Gly  Pro
          100                       105                      110

AGC  GAA  GAG  AAG  CCC  AAG  TTC  CGG  AGC  ATC  GTG  CAC  GCG  GTG  CAG  GCT           500
Ser  Glu  Glu  Lys  Pro  Lys  Phe  Arg  Ser  Ile  Val  His  Ala  Val  Gln  Ala
     115                       120                      125

GGC  ATC  TTT  GTG  GAG  CGG  ATG  TTC  CGG  AGA  ACG  TAC  ACC  TCT  GTG  GGC           548
Gly  Ile  Phe  Val  Glu  Arg  Met  Phe  Arg  Arg  Thr  Tyr  Thr  Ser  Val  Gly
130                       135                      140                      145

CCC  ACC  TAC  TCC  ACT  GCC  GTC  CTC  AAC  TGT  CTC  AAG  AAC  GTG  GAC  CTT           596
Pro  Thr  Tyr  Ser  Thr  Ala  Val  Leu  Asn  Cys  Leu  Lys  Asn  Val  Asp  Leu
                    150                      155                      160

TGG  TGC  TTT  GAT  GTC  TTT  TCC  TTG  AAC  CGG  GCA  GCA  GAT  GAC  CAC  GCC           644
```

|     |     |     |     |     |     |     |     |     |     |     |     |     |     |     |
|---|---|---|---|---|---|---|---|---|---|---|---|---|---|---|
| Trp | Cys | Phe | Asp | Val | Phe | Ser | Leu | Asn | Arg | Ala | Ala | Asp | His | Ala |
|     |     | 165 |     |     |     |     | 170 |     |     |     |     | 175 |     |     |

| CTG | AGG | ACC | ATC | GTT | TTT | GAG | CTG | CTG | ACT | CGG | CAC | AAC | CTC | ATC | AGC | 692 |
|---|---|---|---|---|---|---|---|---|---|---|---|---|---|---|---|---|
| Leu | Arg | Thr | Ile | Val | Phe | Glu | Leu | Leu | Thr | Arg | His | Asn | Leu | Ile | Ser |   |
|     |     | 180 |     |     |     |     | 185 |     |     |     |     | 190 |     |     |     |   |

| CGC | TTT | AAG | ATT | CCC | ACT | GTG | TTT | TTG | ATG | ACT | TTC | CTG | GAT | GCC | TTG | 740 |
|---|---|---|---|---|---|---|---|---|---|---|---|---|---|---|---|---|
| Arg | Phe | Lys | Ile | Pro | Thr | Val | Phe | Leu | Met | Thr | Phe | Leu | Asp | Ala | Leu |   |
|     | 195 |     |     |     |     | 200 |     |     |     |     | 205 |     |     |     |     |   |

| GAG | ACA | GGC | TAC | GGA | AAG | TAC | AAG | AAC | CCT | TAC | CAC | AAC | CAG | ATC | CAC | 788 |
|---|---|---|---|---|---|---|---|---|---|---|---|---|---|---|---|---|
| Glu | Thr | Gly | Tyr | Gly | Lys | Tyr | Lys | Asn | Pro | Tyr | His | Asn | Gln | Ile | His |   |
| 210 |     |     |     |     | 215 |     |     |     |     | 220 |     |     |     |     | 225 |   |

| GCA | GCT | GAC | GTC | ACC | CAG | ACG | GTC | CAC | TGC | TTC | TTG | CTC | CGC | ACA | GGG | 836 |
|---|---|---|---|---|---|---|---|---|---|---|---|---|---|---|---|---|
| Ala | Ala | Asp | Val | Thr | Gln | Thr | Val | His | Cys | Phe | Leu | Leu | Arg | Thr | Gly |   |
|     |     |     |     | 230 |     |     |     |     | 235 |     |     |     |     | 240 |     |   |

| ATG | GTG | CAC | TGC | CTG | TCG | GAG | ATT | GAG | GTC | CTG | GCC | ATC | ATC | TTT | GCT | 884 |
|---|---|---|---|---|---|---|---|---|---|---|---|---|---|---|---|---|
| Met | Val | His | Cys | Leu | Ser | Glu | Ile | Glu | Val | Leu | Ala | Ile | Ile | Phe | Ala |   |
|     |     |     | 245 |     |     |     |     | 250 |     |     |     |     | 255 |     |     |   |

| GCA | GCG | ATC | CAC | GAC | TAT | GAG | CAC | ACT | GGC | ACT | ACC | AAC | AGC | TTC | CAC | 932 |
|---|---|---|---|---|---|---|---|---|---|---|---|---|---|---|---|---|
| Ala | Ala | Ile | His | Asp | Tyr | Glu | His | Thr | Gly | Thr | Thr | Asn | Ser | Phe | His |   |
|     |     | 260 |     |     |     |     | 265 |     |     |     |     | 270 |     |     |     |   |

| ATC | CAG | ACC | AAA | TCG | GAA | TGC | GCC | ATC | CTG | TAC | AAC | GAC | CGC | TCA | GTG | 980 |
|---|---|---|---|---|---|---|---|---|---|---|---|---|---|---|---|---|
| Ile | Gln | Thr | Lys | Ser | Glu | Cys | Ala | Ile | Leu | Tyr | Asn | Asp | Arg | Ser | Val |   |
| 275 |     |     |     |     | 280 |     |     |     |     | 285 |     |     |     |     |     |   |

| CTG | GAG | AAT | CAC | CAC | ATC | AGC | TCG | GTT | TTC | CGA | ATG | ATG | CAG | GAC | GAC | 1028 |
|---|---|---|---|---|---|---|---|---|---|---|---|---|---|---|---|---|
| Leu | Glu | Asn | His | His | Ile | Ser | Ser | Val | Phe | Arg | Met | Met | Gln | Asp | Asp |   |
| 290 |     |     |     |     | 295 |     |     |     |     | 300 |     |     |     |     | 305 |   |

| GAG | ATG | AAC | ATC | TTC | ATC | AAC | CTC | ACC | AAG | GAT | GAG | TTT | GTA | GAG | CTG | 1076 |
|---|---|---|---|---|---|---|---|---|---|---|---|---|---|---|---|---|
| Glu | Met | Asn | Ile | Phe | Ile | Asn | Leu | Thr | Lys | Asp | Glu | Phe | Val | Glu | Leu |   |
|     |     |     |     | 310 |     |     |     |     | 315 |     |     |     |     | 320 |     |   |

| CGG | GCT | CTG | GTC | ATT | GAG | ATG | GTG | TTG | GCC | ACA | GAC | ATG | TCC | TGC | CAT | 1124 |
|---|---|---|---|---|---|---|---|---|---|---|---|---|---|---|---|---|
| Arg | Ala | Leu | Val | Ile | Glu | Met | Val | Leu | Ala | Thr | Asp | Met | Ser | Cys | His |   |
|     |     |     | 325 |     |     |     |     | 330 |     |     |     |     | 335 |     |     |   |

| TTC | CAG | CAA | GTG | AAG | TCC | ATG | AAG | ACA | GCC | TTG | CAG | CAG | CTG | GAG | AGG | 1172 |
|---|---|---|---|---|---|---|---|---|---|---|---|---|---|---|---|---|
| Phe | Gln | Gln | Val | Lys | Ser | Met | Lys | Thr | Ala | Leu | Gln | Gln | Leu | Glu | Arg |   |
|     | 340 |     |     |     |     | 345 |     |     |     |     | 350 |     |     |     |     |   |

| ATT | GAC | AAG | TCC | AAG | GCC | CTC | TCT | CTG | CTG | CTT | CAT | GCT | GCT | GAC | ATC | 1220 |
|---|---|---|---|---|---|---|---|---|---|---|---|---|---|---|---|---|
| Ile | Asp | Lys | Ser | Lys | Ala | Leu | Ser | Leu | Leu | Leu | His | Ala | Ala | Asp | Ile |   |
| 355 |     |     |     |     | 360 |     |     |     |     | 365 |     |     |     |     |     |   |

| AGC | CAC | CCC | ACC | AAG | CAG | TGG | TCG | GTT | CAC | AGC | CGC | TGG | ACC | AAG | GCC | 1268 |
|---|---|---|---|---|---|---|---|---|---|---|---|---|---|---|---|---|
| Ser | His | Pro | Thr | Lys | Gln | Trp | Ser | Val | His | Ser | Arg | Trp | Thr | Lys | Ala |   |
| 370 |     |     |     |     | 375 |     |     |     |     | 380 |     |     |     |     | 385 |   |

| CTC | ATG | GAG | GAA | TTC | TTC | CGC | CAG | GGT | GAC | AAG | GAG | GCT | GAG | CTG | GGC | 1316 |
|---|---|---|---|---|---|---|---|---|---|---|---|---|---|---|---|---|
| Leu | Met | Glu | Glu | Phe | Phe | Arg | Gln | Gly | Asp | Lys | Glu | Ala | Glu | Leu | Gly |   |
|     |     |     |     | 390 |     |     |     |     | 395 |     |     |     |     | 400 |     |   |

| CTG | CCC | TTT | TCT | CCG | CTC | TGT | GAC | CGC | ACT | TCC | ACC | CTC | GTG | GCG | CAG | 1364 |
|---|---|---|---|---|---|---|---|---|---|---|---|---|---|---|---|---|
| Leu | Pro | Phe | Ser | Pro | Leu | Cys | Asp | Arg | Thr | Ser | Thr | Leu | Val | Ala | Gln |   |
|     |     |     | 405 |     |     |     |     | 410 |     |     |     |     | 415 |     |     |   |

| TCC | CAG | ATT | GGT | TTC | ATC | GAC | TTC | ATT | GTG | GAG | CCC | ACG | TTC | TCT | GTG | 1412 |
|---|---|---|---|---|---|---|---|---|---|---|---|---|---|---|---|---|
| Ser | Gln | Ile | Gly | Phe | Ile | Asp | Phe | Ile | Val | Glu | Pro | Thr | Phe | Ser | Val |   |
|     |     | 420 |     |     |     |     | 425 |     |     |     |     | 430 |     |     |     |   |

| CTC | ACC | GAT | GTG | GCT | GAG | AAG | AGT | GTC | CAG | CCC | ACC | GGG | GAC | GAC | GAC | 1460 |
|---|---|---|---|---|---|---|---|---|---|---|---|---|---|---|---|---|
| Leu | Thr | Asp | Val | Ala | Glu | Lys | Ser | Val | Gln | Pro | Thr | Gly | Asp | Asp | Asp |   |
|     | 435 |     |     |     |     | 440 |     |     |     |     | 445 |     |     |     |     |   |

| TCG | AAG | TCT | AAA | AAC | CAG | CCC | AGC | TTC | CAG | TGG | CGC | CAG | CCT | TCT | CTG | 1508 |
|---|---|---|---|---|---|---|---|---|---|---|---|---|---|---|---|---|
| Ser | Lys | Ser | Lys | Asn | Gln | Pro | Ser | Phe | Gln | Trp | Arg | Gln | Pro | Ser | Leu |   |
| 450 |     |     |     |     | 455 |     |     |     |     | 460 |     |     |     |     | 465 |   |

| GAT | GTA | GAA | GTG | GGA | GAC | CCC | AAC | CCT | GAC | GTG | GTC | AGC | TTC | CGC | TCC | 1556 |
|---|---|---|---|---|---|---|---|---|---|---|---|---|---|---|---|---|
| Asp | Val | Glu | Val | Gly | Asp | Pro | Asn | Pro | Asp | Val | Val | Ser | Phe | Arg | Ser |   |
|     |     |     |     | 470 |     |     |     |     | 475 |     |     |     |     | 480 |     |   |

| ACC | TGG | ACC | AAA | TAC | ATT | CAG | GAG | AAC | AAG | CAG | AAA | TGG | AAG | GAA | CGG | 1604 |
|---|---|---|---|---|---|---|---|---|---|---|---|---|---|---|---|---|

-continued

```
Thr  Trp  Thr  Lys  Tyr  Ile  Gln  Glu  Asn  Lys  Gln  Lys  Trp  Lys  Glu  Arg
               485                      490                      495

GCG  GCG  AGC  GGC  ATC  ACC  AAC  CAG  ATG  TCC  ATT  GAC  GAA  CTG  TCC  CCT      1652
Ala  Ala  Ser  Gly  Ile  Thr  Asn  Gln  Met  Ser  Ile  Asp  Glu  Leu  Ser  Pro
               500                      505                      510

TGT  GAG  GAA  GAG  GCC  CCA  GCC  TCC  CCT  GCC  GAA  GAC  GAG  CAC  AAC  CAG      1700
Cys  Glu  Glu  Glu  Ala  Pro  Ala  Ser  Pro  Ala  Glu  Asp  Glu  His  Asn  Gln
     515                      520                      525

AAC  GGG  AAT  CTG  GAC  TAGCGGGGCC  TGGCCAGGTC  CTCACTGAGT  CCTGAGTGTT            1755
Asn  Gly  Asn  Leu  Asp
530

CGATGTCATC  AGCACCATCC  ATCGGGACTG  GCTCCCCCAT  CTGCTCCGAG  GGCGAATGGA             1815

TGTCAAGGAA  CAGAAAACCC  ACCCGAAGA                                                  1844
```

( 2 ) INFORMATION FOR SEQ ID NO:27:

( i ) SEQUENCE CHARACTERISTICS:
        ( A ) LENGTH: 534 amino acids
        ( B ) TYPE: amino acid
        ( D ) TOPOLOGY: linear ( i i ) MOLECULE TYPE: protein ( x i ) SEQUENCE DESCRIPTION: SEQ ID NO:27:

```
Met  Glu  Leu  Ser  Pro  Arg  Ser  Pro  Pro  Glu  Met  Leu  Glu  Ser  Asp  Cys
1                   5                   10                      15

Pro  Ser  Pro  Leu  Glu  Leu  Lys  Ser  Ala  Pro  Ser  Lys  Lys  Met  Trp  Ile
               20                      25                      30

Lys  Leu  Arg  Ser  Leu  Leu  Arg  Tyr  Met  Val  Lys  Gln  Leu  Glu  Asn  Gly
          35                      40                      45

Glu  Val  Asn  Ile  Glu  Glu  Leu  Lys  Lys  Asn  Leu  Glu  Tyr  Thr  Ala  Ser
     50                      55                      60

Leu  Leu  Glu  Ala  Val  Tyr  Ile  Asp  Glu  Thr  Arg  Gln  Ile  Leu  Asp  Thr
65                       70                      75                           80

Glu  Asp  Glu  Leu  Gln  Glu  Leu  Arg  Ser  Asp  Ala  Val  Pro  Ser  Glu  Val
               85                      90                      95

Arg  Asp  Trp  Leu  Ala  Ser  Thr  Phe  Thr  Gln  Gln  Thr  Arg  Ala  Lys  Gly
               100                     105                     110

Pro  Ser  Glu  Glu  Lys  Pro  Lys  Phe  Arg  Ser  Ile  Val  His  Ala  Val  Gln
          115                     120                     125

Ala  Gly  Ile  Phe  Val  Glu  Arg  Met  Phe  Arg  Arg  Thr  Tyr  Thr  Ser  Val
     130                     135                     140

Gly  Pro  Thr  Tyr  Ser  Thr  Ala  Val  Leu  Asn  Cys  Leu  Lys  Asn  Val  Asp
145                      150                     155                          160

Leu  Trp  Cys  Phe  Asp  Val  Phe  Ser  Leu  Asn  Arg  Ala  Ala  Asp  Asp  His
               165                     170                     175

Ala  Leu  Arg  Thr  Ile  Val  Phe  Glu  Leu  Leu  Thr  Arg  His  Asn  Leu  Ile
               180                     185                     190

Ser  Arg  Phe  Lys  Ile  Pro  Thr  Val  Phe  Leu  Met  Thr  Phe  Leu  Asp  Ala
          195                     200                     205

Leu  Glu  Thr  Gly  Tyr  Gly  Lys  Tyr  Lys  Asn  Pro  Tyr  His  Asn  Gln  Ile
     210                     215                     220

His  Ala  Ala  Asp  Val  Thr  Gln  Thr  Val  His  Cys  Phe  Leu  Leu  Arg  Thr
225                      230                     235                          240

Gly  Met  Val  His  Cys  Leu  Ser  Glu  Ile  Glu  Val  Leu  Ala  Ile  Ile  Phe
               245                     250                     255

Ala  Ala  Ala  Ile  His  Asp  Tyr  Glu  His  Thr  Gly  Thr  Thr  Asn  Ser  Phe
```

|     |     |     |     | 260 |     |     |     |     |     | 265 |     |     |     |     |     | 270 |     |     |
| --- | --- | --- | --- | --- | --- | --- | --- | --- | --- | --- | --- | --- | --- | --- | --- | --- | --- | --- |
| His | Ile | Gln | Thr | Lys | Ser | Glu | Cys | Ala | Ile | Leu | Tyr | Asn | Asp | Arg | Ser |
|     |     |     | 275 |     |     |     | 280 |     |     |     |     | 285 |     |     |     |
| Val | Leu | Glu | Asn | His | His | Ile | Ser | Ser | Val | Phe | Arg | Met | Met | Gln | Asp |
|     |     | 290 |     |     |     | 295 |     |     |     |     |     | 300 |     |     |     |
| Asp | Glu | Met | Asn | Ile | Phe | Ile | Asn | Leu | Thr | Lys | Asp | Glu | Phe | Val | Glu |
| 305 |     |     |     |     | 310 |     |     |     |     | 315 |     |     |     |     | 320 |
| Leu | Arg | Ala | Leu | Val | Ile | Glu | Met | Val | Leu | Ala | Thr | Asp | Met | Ser | Cys |
|     |     |     |     | 325 |     |     |     |     | 330 |     |     |     |     | 335 |     |
| His | Phe | Gln | Gln | Val | Lys | Ser | Met | Lys | Thr | Ala | Leu | Gln | Gln | Leu | Glu |
|     |     |     |     | 340 |     |     |     |     | 345 |     |     |     |     | 350 |     |
| Arg | Ile | Asp | Lys | Ser | Lys | Ala | Leu | Ser | Leu | Leu | Leu | His | Ala | Ala | Asp |
|     |     |     | 355 |     |     |     |     | 360 |     |     |     |     | 365 |     |     |
| Ile | Ser | His | Pro | Thr | Lys | Gln | Trp | Ser | Val | His | Ser | Arg | Trp | Thr | Lys |
|     | 370 |     |     |     |     |     | 375 |     |     |     |     | 380 |     |     |     |
| Ala | Leu | Met | Glu | Glu | Phe | Phe | Arg | Gln | Gly | Asp | Lys | Glu | Ala | Glu | Leu |
| 385 |     |     |     |     | 390 |     |     |     |     | 395 |     |     |     |     | 400 |
| Gly | Leu | Pro | Phe | Ser | Pro | Leu | Cys | Asp | Arg | Thr | Ser | Thr | Leu | Val | Ala |
|     |     |     |     | 405 |     |     |     |     | 410 |     |     |     |     | 415 |     |
| Gln | Ser | Gln | Ile | Gly | Phe | Ile | Asp | Phe | Ile | Val | Glu | Pro | Thr | Phe | Ser |
|     |     |     |     | 420 |     |     |     |     | 425 |     |     |     |     | 430 |     |
| Val | Leu | Thr | Asp | Val | Ala | Glu | Lys | Ser | Val | Gln | Pro | Thr | Gly | Asp | Asp |
|     |     |     | 435 |     |     |     |     | 440 |     |     |     |     | 445 |     |     |
| Asp | Ser | Lys | Ser | Lys | Asn | Gln | Pro | Ser | Phe | Gln | Trp | Arg | Gln | Pro | Ser |
|     |     | 450 |     |     |     |     | 455 |     |     |     |     | 460 |     |     |     |
| Leu | Asp | Val | Glu | Val | Gly | Asp | Pro | Asn | Pro | Asp | Val | Val | Ser | Phe | Arg |
| 465 |     |     |     |     | 470 |     |     |     |     | 475 |     |     |     |     | 480 |
| Ser | Thr | Trp | Thr | Lys | Tyr | Ile | Gln | Glu | Asn | Lys | Gln | Lys | Trp | Lys | Glu |
|     |     |     |     | 485 |     |     |     |     | 490 |     |     |     |     | 495 |     |
| Arg | Ala | Ala | Ser | Gly | Ile | Thr | Asn | Gln | Met | Ser | Ile | Asp | Glu | Leu | Ser |
|     |     |     |     | 500 |     |     |     |     | 505 |     |     |     |     | 510 |     |
| Pro | Cys | Glu | Glu | Glu | Ala | Pro | Ala | Ser | Pro | Ala | Glu | Asp | Glu | His | Asn |
|     |     |     | 515 |     |     |     |     | 520 |     |     |     |     | 525 |     |     |
| Gln | Asn | Gly | Asn | Leu | Asp |
|     |     |     |     | 530 |     |

( 2 ) INFORMATION FOR SEQ ID NO:28:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:28:

| Gln | Leu | Glu | Asn | Gly | Glu | Val | Asn | Ile | Glu | Glu | Leu | Lys | Lys |
| --- | --- | --- | --- | --- | --- | --- | --- | --- | --- | --- | --- | --- | --- |
| 1 |   |   |   | 5 |   |   |   |   | 10 |

( 2 ) INFORMATION FOR SEQ ID NO:29:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:29:

```
       Gln  Leu  Ile  Pro  Gly  Arg  Val  Asn  Ile  Ile  Ser  Leu  Lys  Lys
        1              5                        10
```

(2) INFORMATION FOR SEQ ID NO:30:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:30:

```
   Lys  Ser  Glu  Cys  Ala  Ile  Leu  Tyr  Asn  Asp  Arg  Ser  Val  Leu  Glu  Asn
    1              5                        10                        15
```

(2) INFORMATION FOR SEQ ID NO:31:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:31:

```
   Lys  Asp  Glu  Thr  Ala  Ile  Leu  Tyr  Asn  Asp  Arg  Thr  Val  Leu  Glu  Asn
    1              5                        10                        15
```

(2) INFORMATION FOR SEQ ID NO:32:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

```
GGATCCGGAT  CCCGCAGACG  GAGGCTGAGC  ATGG                                      34
```

(2) INFORMATION FOR SEQ ID NO:33:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

```
GGATCCGGAT  CCAGGACCTG  GCCAGGCCCG  GC                                        32
```

(2) INFORMATION FOR SEQ ID NO:34:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:34:

```
   Glu  Met  Met  Met  Tyr  His  Met  Lys
    1              5
```

(2) INFORMATION FOR SEQ ID NO:35:

( i ) SEQUENCE CHARACTERISTICS:
   ( A ) LENGTH: 8 amino acids
   ( B ) TYPE: amino acid
   ( D ) TOPOLOGY: linear ( i i ) MOLECULE TYPE: peptide ( x i ) SEQUENCE DESCRIPTION: SEQ ID NO:35:

Tyr His Asn Trp Met His Ala Phe
1               5

( 2 ) INFORMATION FOR SEQ ID NO:36:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:36:

TTCATRTGRT ACATCATCAT YTC                23

( 2 ) INFORMATION FOR SEQ ID NO:37:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:37:

AANGCRTGCA TCCARTTRTG RTA                23

( 2 ) INFORMATION FOR SEQ ID NO:38:

( i ) SEQUENCE CHARACTERISTICS:
      ( A ) LENGTH: 4131 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:
      ( A ) NAME/KEY: CDS
      ( B ) LOCATION: 148..2910

( x i ) SEQUENCE DESCRIPTION: SEQ ID NO:38:

AGGCGCAGCG GCCGGGCCGG CGGGCGGGCG GGCGGCTGCG AGCATGGTCC TGGTGCTGCA         60

CCACATCCTC ATCGCTGTTG TCCAATTCTT CAGGCGGGGC CAGCAGGTCT TCCTCAAGCC        120

GGACGAGCCG CCGCCGCCGC CGCAGCC ATG CGC CGA CAG CCT GCA GCC AGC            171
                              Met Arg Arg Gln Pro Ala Ala Ser
                                1               5

CGG GAC CTC TTT GCA CAG GAG CCA GTG CCC CCA GGG AGT GGA GAC GGC          219
Arg Asp Leu Phe Ala Gln Glu Pro Val Pro Pro Gly Ser Gly Asp Gly
    10              15                  20

GCA TTG CAG GAT GCT TTG CTG AGC CTG GGC TCC GTC ATC GAC GTT GCA          267
Ala Leu Gln Asp Ala Leu Leu Ser Leu Gly Ser Val Ile Asp Val Ala
25                  30                  35                  40

GGC TTG CAA CAG GCT GTC AAG GAG GCC CTG TCG GCT GTG CTT CCC AAA          315
Gly Leu Gln Gln Ala Val Lys Glu Ala Leu Ser Ala Val Leu Pro Lys
            45                  50                  55

-continued

| | | | | | | | | | | | | | | | | |
|---|---|---|---|---|---|---|---|---|---|---|---|---|---|---|---|---|
| GTG | GAG | ACG | GTC | TAC | ACC | TAC | CTG | CTG | GAT | GGG | GAA | TCC | CGG | CTG | GTG | 363 |
| Val | Glu | Thr | Val 60 | Tyr | Thr | Tyr | Leu | Leu 65 | Asp | Gly | Glu | Ser | Arg 70 | Leu | Val | |
| TGT | GAG | GAG | CCC | CCC | CAC | GAG | CTG | CCC | CAG | GAG | GGG | AAA | GTG | CGA | GAG | 411 |
| Cys | Glu | Glu 75 | Pro | Pro | His | Glu | Leu 80 | Pro | Gln | Glu | Gly | Lys 85 | Val | Arg | Glu | |
| GCT | GTG | ATC | TCC | CGG | AAG | CGG | CTG | GGC | TGC | AAT | GGA | CTG | GGC | CCC | TCA | 459 |
| Ala | Val 90 | Ile | Ser | Arg | Lys | Arg 95 | Leu | Gly | Cys | Asn | Gly 100 | Leu | Gly | Pro | Ser | |
| GAC | CTG | CCT | GGG | AAG | CCC | TTG | GCA | AGG | CTG | GTG | GCT | CCA | CTG | GCT | CCT | 507 |
| Asp 105 | Leu | Pro | Gly | Lys | Pro 110 | Leu | Ala | Arg | Leu | Val 115 | Ala | Pro | Leu | Ala | Pro 120 | |
| GAC | ACC | CAA | GTG | CTG | GTC | ATA | CCG | CTG | GTG | GAC | AAG | GAG | GCC | GGG | GCT | 555 |
| Asp | Thr | Gln | Val | Leu 125 | Val | Ile | Pro | Leu | Val 130 | Asp | Lys | Glu | Ala | Gly 135 | Ala | |
| GTG | GCA | GCT | GTC | ATC | TTG | GTG | CAC | TGT | GGT | CAG | CTG | AGT | GAC | AAT | GAG | 603 |
| Val | Ala | Ala | Val 140 | Ile | Leu | Val | His | Cys 145 | Gly | Gln | Leu | Ser | Asp 150 | Asn | Glu | |
| GAG | TGG | AGC | CTG | CAA | GCT | GTG | GAG | AAG | CAT | ACC | CTG | GTG | GCC | CTG | AAA | 651 |
| Glu | Trp | Ser 155 | Leu | Gln | Ala | Val | Glu 160 | Lys | His | Thr | Leu | Val 165 | Ala | Leu | Lys | |
| AGG | GTG | CAG | GCC | TTG | CAG | CAG | CGC | GAG | TCC | AGC | GTG | GCC | CCG | GAA | GCG | 699 |
| Arg | Val 170 | Gln | Ala | Leu | Gln | Gln 175 | Arg | Glu | Ser | Ser | Val 180 | Ala | Pro | Glu | Ala | |
| ACC | CAG | AAT | CCT | CCG | GAG | GAG | GCA | GCG | GGA | GAC | CAG | AAG | GGT | GGG | GTC | 747 |
| Thr 185 | Gln | Asn | Pro | Pro | Glu 190 | Glu | Ala | Ala | Gly | Asp 195 | Gln | Lys | Gly | Gly | Val 200 | |
| GCA | TAC | ACA | AAC | CAA | GAC | CGA | AAG | ATC | CTG | CAG | CTT | TGC | GGG | GAG | CTC | 795 |
| Ala | Tyr | Thr | Asn | Gln 205 | Asp | Arg | Lys | Ile | Leu 210 | Gln | Leu | Cys | Gly | Glu 215 | Leu | |
| TAC | GAC | CTG | GAT | GCA | TCT | TCC | CTG | CAG | CTC | AAA | GTC | CTC | CAA | TAT | CTG | 843 |
| Tyr | Asp | Leu | Asp 220 | Ala | Ser | Ser | Leu | Gln 225 | Leu | Lys | Val | Leu | Gln 230 | Tyr | Leu | |
| CAA | CAG | GAG | ACC | CAG | GCA | TCC | CGC | TGC | TGC | CTG | CTG | CTG | GTA | TCC | GAG | 891 |
| Gln | Gln | Glu | Thr 235 | Gln | Ala | Ser | Arg | Cys 240 | Cys | Leu | Leu | Leu | Val 245 | Ser | Glu | |
| GAC | AAT | CTT | CAG | CTC | TCC | TGC | AAG | GTC | ATT | GGA | GAT | AAA | GTA | CTG | GAG | 939 |
| Asp | Asn | Leu 250 | Gln | Leu | Ser | Cys | Lys 255 | Val | Ile | Gly | Asp | Lys 260 | Val | Leu | Glu | |
| GAA | GAG | ATC | AGC | TTT | CCG | TTG | ACC | ACA | GGA | CGC | CTG | GGC | CAA | GTG | GTG | 987 |
| Glu 265 | Glu | Ile | Ser | Phe | Pro 270 | Leu | Thr | Thr | Gly | Arg 275 | Leu | Gly | Gln | Val | Val 280 | |
| GAA | GAC | AAG | AAG | TCT | ATC | CAG | CTG | AAA | GAT | CTC | ACC | TCC | GAG | GAT | ATG | 1035 |
| Glu | Asp | Lys | Lys | Ser 285 | Ile | Gln | Leu | Lys | Asp 290 | Leu | Thr | Ser | Glu | Asp 295 | Met | |
| CAA | CAG | CTG | CAA | AGC | ATG | TTG | GGC | TGT | GAG | GTG | CAG | GCC | ATG | CTC | TGT | 1083 |
| Gln | Gln | Leu | Gln 300 | Ser | Met | Leu | Gly | Cys 305 | Glu | Val | Gln | Ala | Met 310 | Leu | Cys | |
| GTC | CCT | GTC | ATC | AGC | CGG | GCC | ACT | GAC | CAG | GTC | GTG | GCC | CTG | GCC | TGT | 1131 |
| Val | Pro | Val 315 | Ile | Ser | Arg | Ala | Thr 320 | Asp | Gln | Val | Val | Ala 325 | Leu | Ala | Cys | |
| GCC | TTC | AAC | AAG | CTC | GGA | GGA | GAC | TTG | TTC | ACA | GAC | CAG | GAC | GAG | CAC | 1179 |
| Ala | Phe 330 | Asn | Lys | Leu | Gly | Gly 335 | Asp | Leu | Phe | Thr | Asp 340 | Gln | Asp | Glu | His | |
| GTG | ATC | CAG | CAC | TGC | TTC | CAC | TAC | ACC | AGC | ACA | GTG | CTC | ACC | AGC | ACC | 1227 |
| Val | Ile | Gln | His 345 | Cys | Phe | His 350 | Tyr | Thr | Ser | Thr | Val 355 | Leu | Thr | Ser | Thr 360 | |
| CTG | GCC | TTC | CAG | AAG | GAG | CAG | AAG | CTC | AAG | TGT | GAG | TGC | CAG | GCT | CTT | 1275 |
| Leu | Ala | Phe | Gln | Lys 365 | Glu | Gln | Lys | Leu | Lys 370 | Cys | Glu | Cys | Gln | Ala 375 | Leu | |

| | | | | | | | | | | | | | | | | |
|---|---|---|---|---|---|---|---|---|---|---|---|---|---|---|---|---|
| CTC | CAA | GTG | GCG | AAG | AAC | CTC | TTC | ACT | CAT | CTG | GAT | GAC | GTC | TCC | GTG | 1323 |
| Leu | Gln | Val | Ala | Lys | Asn | Leu | Phe | Thr | His | Leu | Asp | Asp | Val | Ser | Val | |
| | | | 380 | | | | 385 | | | | | 390 | | | | |
| CTG | CTC | CAG | GAG | ATC | ATC | ACA | GAG | GCC | AGG | AAC | CTC | AGC | AAT | GCT | GAG | 1371 |
| Leu | Leu | Gln | Glu | Ile | Ile | Thr | Glu | Ala | Arg | Asn | Leu | Ser | Asn | Ala | Glu | |
| | | 395 | | | | | 400 | | | | | 405 | | | | |
| ATC | TGC | TCT | GTG | TTC | CTG | CTG | GAT | CAG | AAC | GAG | CTG | GTG | GCC | AAG | GTG | 1419 |
| Ile | Cys | Ser | Val | Phe | Leu | Leu | Asp | Gln | Asn | Glu | Leu | Val | Ala | Lys | Val | |
| | 410 | | | | | 415 | | | | | 420 | | | | | |
| TTC | GAT | GGG | GGT | GTG | GTG | GAA | GAT | GAG | AGC | TAT | GAG | ATC | CGC | ATT | CCC | 1467 |
| Phe | Asp | Gly | Gly | Val | Val | Glu | Asp | Glu | Ser | Tyr | Glu | Ile | Arg | Ile | Pro | |
| 425 | | | | | 430 | | | | 435 | | | | | 440 | | |
| GCT | GAC | CAG | GGC | ATC | GCG | GGT | CAT | GTG | GCG | ACC | ACC | GGC | CAG | ATC | CTA | 1515 |
| Ala | Asp | Gln | Gly | Ile | Ala | Gly | His | Val | Ala | Thr | Thr | Gly | Gln | Ile | Leu | |
| | | | | 445 | | | | | 450 | | | | | 455 | | |
| AAC | ATC | CCA | GAT | GCT | TAC | GCA | CAT | CCG | CTT | TTC | TAC | CGA | GGC | GTG | GAC | 1563 |
| Asn | Ile | Pro | Asp | Ala | Tyr | Ala | His | Pro | Leu | Phe | Tyr | Arg | Gly | Val | Asp | |
| | | | 460 | | | | | 465 | | | | | 470 | | | |
| GAC | AGC | ACC | GGC | TTC | CGG | ACG | CGC | AAC | ATC | CTC | TGC | TTC | CCC | ATC | AAG | 1611 |
| Asp | Ser | Thr | Gly | Phe | Arg | Thr | Arg | Asn | Ile | Leu | Cys | Phe | Pro | Ile | Lys | |
| | | 475 | | | | | 480 | | | | | 485 | | | | |
| AAC | GAG | AAC | CAG | GAG | GTC | ATC | GGT | GTG | GCC | GAG | CTG | GTG | AAC | AAG | ATC | 1659 |
| Asn | Glu | Asn | Gln | Glu | Val | Ile | Gly | Val | Ala | Glu | Leu | Val | Asn | Lys | Ile | |
| | 490 | | | | | 495 | | | | | 500 | | | | | |
| AAT | GGA | CCA | TGG | TTC | AGC | AAG | TTT | GAT | GAA | GAC | CTG | GCT | ACA | GCC | TTC | 1707 |
| Asn | Gly | Pro | Trp | Phe | Ser | Lys | Phe | Asp | Glu | Asp | Leu | Ala | Thr | Ala | Phe | |
| 505 | | | | | 510 | | | | | 515 | | | | | 520 | |
| TCC | ATC | TAC | TGT | GGC | ATC | AGC | ATT | GCC | CAT | TCC | CTC | CTA | TAC | AAG | AAA | 1755 |
| Ser | Ile | Tyr | Cys | Gly | Ile | Ser | Ile | Ala | His | Ser | Leu | Leu | Tyr | Lys | Lys | |
| | | | | 525 | | | | | 530 | | | | | 535 | | |
| GTG | AAT | GAG | GCG | CAG | TAT | CGC | AGC | CAC | CTT | GCC | AAT | GAG | ATG | ATG | ATG | 1803 |
| Val | Asn | Glu | Ala | Gln | Tyr | Arg | Ser | His | Leu | Ala | Asn | Glu | Met | Met | Met | |
| | | | 540 | | | | | 545 | | | | | 550 | | | |
| TAC | CAC | ATG | AAG | GTC | TCT | GAT | GAC | GAG | TAC | ACC | AAA | CTT | CTC | CAT | GAC | 1851 |
| Tyr | His | Met | Lys | Val | Ser | Asp | Asp | Glu | Tyr | Thr | Lys | Leu | Leu | His | Asp | |
| | | 555 | | | | | 560 | | | | | 565 | | | | |
| GGG | ATC | CAG | CCT | GTG | GCT | GCC | ATC | GAC | TCC | AAC | TTT | GCC | AGT | TTC | ACA | 1899 |
| Gly | Ile | Gln | Pro | Val | Ala | Ala | Ile | Asp | Ser | Asn | Phe | Ala | Ser | Phe | Thr | |
| | 570 | | | | | 575 | | | | | 580 | | | | | |
| TAC | ACT | CCT | CGC | TCT | CTG | CCC | GAG | GAT | GAC | ACT | TCC | ATG | GCC | ATC | CTG | 1947 |
| Tyr | Thr | Pro | Arg | Ser | Leu | Pro | Glu | Asp | Asp | Thr | Ser | Met | Ala | Ile | Leu | |
| 585 | | | | | 590 | | | | | 595 | | | | | 600 | |
| AGC | ATG | CTG | CAG | GAC | ATG | AAT | TTC | ATC | AAT | AAC | TAC | AAA | ATT | GAC | TGC | 1995 |
| Ser | Met | Leu | Gln | Asp | Met | Asn | Phe | Ile | Asn | Asn | Tyr | Lys | Ile | Asp | Cys | |
| | | | | 605 | | | | | 610 | | | | | 615 | | |
| CCG | ACA | CTG | GCC | CGG | TTC | TGT | TTG | ATG | GTG | AAG | AAG | GGC | TAC | CGG | GAT | 2043 |
| Pro | Thr | Leu | Ala | Arg | Phe | Cys | Leu | Met | Val | Lys | Lys | Gly | Tyr | Arg | Asp | |
| | | | 620 | | | | | 625 | | | | | 630 | | | |
| CCC | CCC | TAC | CAC | AAC | TGG | ATG | CAC | GCC | TTT | TCT | GTC | TCC | CAC | TTC | TGC | 2091 |
| Pro | Pro | Tyr | His | Asn | Trp | Met | His | Ala | Phe | Ser | Val | Ser | His | Phe | Cys | |
| | | 635 | | | | | 640 | | | | | 645 | | | | |
| TAC | CTG | CTC | TAC | AAG | AAC | CTG | GAG | CTC | ACC | AAC | TAC | CTC | GAG | GAC | ATG | 2139 |
| Tyr | Leu | Leu | Tyr | Lys | Asn | Leu | Glu | Leu | Thr | Asn | Tyr | Leu | Glu | Asp | Met | |
| | 650 | | | | | 655 | | | | | 660 | | | | | |
| GAG | ATC | TTT | GCC | TTG | TTT | ATT | TCC | TGC | ATG | TGT | CAC | GAC | CTG | GAC | CAC | 2187 |
| Glu | Ile | Phe | Ala | Leu | Phe | Ile | Ser | Cys | Met | Cys | His | Asp | Leu | Asp | His | |
| 665 | | | | | 670 | | | | | 675 | | | | | 680 | |
| AGA | GGC | ACA | AAC | AAC | TCC | TTC | CAG | GTG | GCC | TCG | AAA | TCT | GTG | CTG | GCC | 2235 |
| Arg | Gly | Thr | Asn | Asn | Ser | Phe | Gln | Val | Ala | Ser | Lys | Ser | Val | Leu | Ala | |
| | | | | 685 | | | | | 690 | | | | | 695 | | |

| | |
|---|---|
| GCG CTC TAC AGC TCG GAA GGC TCT GTC ATG GAG AGG CAC CAC TTC GCT<br>Ala Leu Tyr Ser Ser Glu Gly Ser Val Met Glu Arg His His Phe Ala<br>700 705 710 | 2283 |
| CAG GCC ATT GCC ATC CTC AAC ACC CAC GGC TGC AAC ATC TTT GAC CAC<br>Gln Ala Ile Ala Ile Leu Asn Thr His Gly Cys Asn Ile Phe Asp His<br>715 720 725 | 2331 |
| TTC TCC CGG AAG GAT TAT CAG CGC ATG TTG GAC CTG ATG CGG GAC ATC<br>Phe Ser Arg Lys Asp Tyr Gln Arg Met Leu Asp Leu Met Arg Asp Ile<br>730 735 740 | 2379 |
| ATC TTG GCC ACA GAT CTG GCC CAC CAC CTC CGC ATC TTC AAG GAC CTC<br>Ile Leu Ala Thr Asp Leu Ala His His Leu Arg Ile Phe Lys Asp Leu<br>745 750 755 760 | 2427 |
| CAA AAG ATG GCC GAA GTG GGC TAT GAT CGA ACC AAC AAG CAG CAC CAC<br>Gln Lys Met Ala Glu Val Gly Tyr Asp Arg Thr Asn Lys Gln His His<br>765 770 775 | 2475 |
| AGC CTC CTT CTC TGC CTC CTT ATG ACC TCC TGT GAC CTC TCT GAC CAG<br>Ser Leu Leu Leu Cys Leu Leu Met Thr Ser Cys Asp Leu Ser Asp Gln<br>780 785 790 | 2523 |
| ACC AAG GGC TGG AAG ACC ACG AGG AAG ATC GCG GAG CTG ATC TAC AAA<br>Thr Lys Gly Trp Lys Thr Thr Arg Lys Ile Ala Glu Leu Ile Tyr Lys<br>795 800 805 | 2571 |
| GAG TTC TTC TCC CAG GGA GAC TTG GAG AAG GCC ATG GGC AAC AGG CCG<br>Glu Phe Phe Ser Gln Gly Asp Leu Glu Lys Ala Met Gly Asn Arg Pro<br>810 815 820 | 2619 |
| ATG GAG ATG ATG GAC CGT GAG AAG GCC TAC ATC CCC GAG CTG CAG ATC<br>Met Glu Met Met Asp Arg Glu Lys Ala Tyr Ile Pro Glu Leu Gln Ile<br>825 830 835 840 | 2667 |
| AGC TTC ATG GAG CAC ATC GCA ATG CCC ATC TAC AAG CTG CTG CAA GAC<br>Ser Phe Met Glu His Ile Ala Met Pro Ile Tyr Lys Leu Leu Gln Asp<br>845 850 855 | 2715 |
| CTG TTC CCC AAG GCG GCC GAG TTG TAC GAA CGC GTG GCC TCT AAT CGT<br>Leu Phe Pro Lys Ala Ala Glu Leu Tyr Glu Arg Val Ala Ser Asn Arg<br>860 865 870 | 2763 |
| GAG CAC TGG ACC AAG GTG TCA CAC AAG TTC ACC ATC CGA GGC CTC CCG<br>Glu His Trp Thr Lys Val Ser His Lys Phe Thr Ile Arg Gly Leu Pro<br>875 880 885 | 2811 |
| AGC AAC AAC TCG TTG GAC TTC CTG GAC GAG GAG TAT GAG GTG CCT GAC<br>Ser Asn Asn Ser Leu Asp Phe Leu Asp Glu Glu Tyr Glu Val Pro Asp<br>890 895 900 | 2859 |
| CTG GAT GGC GCT AGG GCT CCC ATC AAT GGC TGT TGC AGC CTT GAT GCT<br>Leu Asp Gly Ala Arg Ala Pro Ile Asn Gly Cys Cys Ser Leu Asp Ala<br>905 910 915 920 | 2907 |
| GAG TGAGTCCCTC CTGGGACCCC TCCCTGTCCA GGCCTCCTCC CACAAGCCTC<br>Glu | 2960 |
| CACGGGCCTG GCCGCACGCC CTGGGACCAG AGCCAAGGGT CCTGGATTCT AGGCCAGGAC | 3020 |
| TTCCCATGTG ACCCGGGCGA GGTCTGACCT TCCCGGGCCT CAGCTTTCTT GTCTGTATAA | 3080 |
| TGGAAGACTT CAGCCTCACT GAGACTTTGT CACTTGTCCT CTGAGAGCAC AGGGGTAACC | 3140 |
| AATGAGCAGT GGACCCTGCT CTGCACCTCT GACCGCATCT TGGCAAGTCC CCACCCTCCA | 3200 |
| GGCCACTCCT TCTCTGAGGC AGCCGGATGG TTTCTTCTGG GCCCCATTCC TGCCCTACCA | 3260 |
| GACCTGTGCC CTTTCCTGTG GGGGCACCCT CACTGGCTCC CAGGATCCTC AGGCAAGAAC | 3320 |
| ATGAGACATC TGAGTGGGCA AAGGGTGGGT CTTAGAGACA GTTATCAGCC TGGCTGGAGG | 3380 |
| ACTAGAAGTA GCCATGGGAC CACCTGTGGC CCAGAGGACT GCCTTTGTAC TTATGGTGGG | 3440 |
| GACTGGGACC TGGGGATATA AGGGTCCCAG GAGGACACTG CCAGGGGCC AGTGCAGTGC | 3500 |
| TCTGGGGAGA GGGGGCTCAG GAAGAGAGGA GGATAAGAAC AGTGAGAAGG AAGGATCCCT | 3560 |
| GGGTTGGGAG GCAGGCCCAG CATGGGTCAG CCATGCTTCC TCCTGGCTGT GTGACCCTGG | 3620 |

-continued

```
GCAAGTCCCT TCCCCTCTCT GCGAAACAGT AGGGTGAGAC AATCCATTCT CTAAGACCCC    3680
TTTTAGATCC AAGTCCCCAT AGTTCTGTGG AGTCCCAGTA GAGGCCACCG AGGGTCCCTG    3740
GCCCCCTTGG GCACAGAGCT GACACTGAGT CCCTCAGTGG CCCCCTGAGT ATACCCCTT     3800
AGCCGGAGCC CCTTCCCCAT TCCTACAGCC AGAGGGGAC CTGGCCTCAG CCTGGCAGGG     3860
CCTCTCTCCT CTTCAAGGCC ATATCCACCT GTGCCCGGG GCTTGGGAGA CCCCTAGGG      3920
CCGGAGCTCT GGGGTCATCC TGGCCACTGG CTTCTCCTTT CTCTGTTTTG TTCTGTATGT    3980
GTTGTGGGGT GGGGGGAGGG GGGCCACCTG CCTTACCTAT TCTGAGTTGC CTTTAGAGAG    4040
ATGCGTTTTT TCTAGGACTC TGTGCAACTG TTGTATATGG TTCCGTGGGC TGACCGCTTT    4100
GTACATGAGA ATAAATCTAT TTCTTTCTAC C                                   4131
```

( 2 ) INFORMATION FOR SEQ ID NO:39:

( i ) SEQUENCE CHARACTERISTICS:
        ( A ) LENGTH: 921 amino acids
        ( B ) TYPE: amino acid
        ( D ) TOPOLOGY: linear ( i i ) MOLECULE TYPE: protein ( x i ) SEQUENCE DESCRIPTION: SEQ ID NO:39:

```
Met Arg Arg Gln Pro Ala Ala Ser Arg Asp Leu Phe Ala Gln Glu Pro
  1               5                  10                  15

Val Pro Pro Gly Ser Gly Asp Gly Ala Leu Gln Asp Ala Leu Leu Ser
                 20                  25                  30

Leu Gly Ser Val Ile Asp Val Ala Gly Leu Gln Gln Ala Val Lys Glu
             35                  40                  45

Ala Leu Ser Ala Val Leu Pro Lys Val Glu Thr Val Tyr Thr Tyr Leu
 50                  55                  60

Leu Asp Gly Glu Ser Arg Leu Val Cys Glu Glu Pro Pro His Glu Leu
 65                  70                  75                  80

Pro Gln Glu Gly Lys Val Arg Glu Ala Val Ile Ser Arg Lys Arg Leu
                 85                  90                  95

Gly Cys Asn Gly Leu Gly Pro Ser Asp Leu Pro Gly Lys Pro Leu Ala
                100                 105                 110

Arg Leu Val Ala Pro Leu Ala Pro Asp Thr Gln Val Leu Val Ile Pro
            115                 120                 125

Leu Val Asp Lys Glu Ala Gly Ala Val Ala Ala Val Ile Leu Val His
130                 135                 140

Cys Gly Gln Leu Ser Asp Asn Glu Glu Trp Ser Leu Gln Ala Val Glu
145                 150                 155                 160

Lys His Thr Leu Val Ala Leu Lys Arg Val Gln Ala Leu Gln Gln Arg
                165                 170                 175

Glu Ser Ser Val Ala Pro Glu Ala Thr Gln Asn Pro Pro Glu Glu Ala
            180                 185                 190

Ala Gly Asp Gln Lys Gly Gly Val Ala Tyr Thr Asn Gln Asp Arg Lys
        195                 200                 205

Ile Leu Gln Leu Cys Gly Glu Leu Tyr Asp Leu Asp Ala Ser Ser Leu
    210                 215                 220

Gln Leu Lys Val Leu Gln Tyr Leu Gln Gln Glu Thr Gln Ala Ser Arg
225                 230                 235                 240

Cys Cys Leu Leu Leu Val Ser Glu Asp Asn Leu Gln Leu Ser Cys Lys
                245                 250                 255

Val Ile Gly Asp Lys Val Leu Glu Glu Glu Ile Ser Phe Pro Leu Thr
```

```
                    260                        265                         270
Thr  Gly  Arg  Leu  Gly  Gln  Val  Val  Glu  Asp  Lys  Lys  Ser  Ile  Gln  Leu
               275                        280                   285
Lys  Asp  Leu  Thr  Ser  Glu  Asp  Met  Gln  Gln  Leu  Gln  Ser  Met  Leu  Gly
          290                        295                   300
Cys  Glu  Val  Gln  Ala  Met  Leu  Cys  Val  Pro  Val  Ile  Ser  Arg  Ala  Thr
305                        310                        315                   320
Asp  Gln  Val  Val  Ala  Leu  Ala  Cys  Ala  Phe  Asn  Lys  Leu  Gly  Gly  Asp
                    325                        330                        335
Leu  Phe  Thr  Asp  Gln  Asp  Glu  His  Val  Ile  Gln  His  Cys  Phe  His  Tyr
               340                        345                        350
Thr  Ser  Thr  Val  Leu  Thr  Ser  Thr  Leu  Ala  Phe  Gln  Lys  Glu  Gln  Lys
               355                        360                   365
Leu  Lys  Cys  Glu  Cys  Gln  Ala  Leu  Leu  Gln  Val  Ala  Lys  Asn  Leu  Phe
          370                        375                   380
Thr  His  Leu  Asp  Asp  Val  Ser  Val  Leu  Leu  Gln  Glu  Ile  Ile  Thr  Glu
385                        390                        395                   400
Ala  Arg  Asn  Leu  Ser  Asn  Ala  Glu  Ile  Cys  Ser  Val  Phe  Leu  Leu  Asp
                    405                        410                        415
Gln  Asn  Glu  Leu  Val  Ala  Lys  Val  Phe  Asp  Gly  Gly  Val  Val  Glu  Asp
               420                        425                   430
Glu  Ser  Tyr  Glu  Ile  Arg  Ile  Pro  Ala  Asp  Gln  Gly  Ile  Ala  Gly  His
               435                        440                        445
Val  Ala  Thr  Thr  Gly  Gln  Ile  Leu  Asn  Ile  Pro  Asp  Ala  Tyr  Ala  His
          450                        455                   460
Pro  Leu  Phe  Tyr  Arg  Gly  Val  Asp  Asp  Ser  Thr  Gly  Phe  Arg  Thr  Arg
465                        470                        475                   480
Asn  Ile  Leu  Cys  Phe  Pro  Ile  Lys  Asn  Glu  Asn  Gln  Glu  Val  Ile  Gly
                    485                        490                        495
Val  Ala  Glu  Leu  Val  Asn  Lys  Ile  Asn  Gly  Pro  Trp  Phe  Ser  Lys  Phe
               500                        505                        510
Asp  Glu  Asp  Leu  Ala  Thr  Ala  Phe  Ser  Ile  Tyr  Cys  Gly  Ile  Ser  Ile
          515                        520                   525
Ala  His  Ser  Leu  Leu  Tyr  Lys  Lys  Val  Asn  Glu  Ala  Gln  Tyr  Arg  Ser
          530                        535                   540
His  Leu  Ala  Asn  Glu  Met  Met  Met  Tyr  His  Met  Lys  Val  Ser  Asp  Asp
545                        550                        555                   560
Glu  Tyr  Thr  Lys  Leu  Leu  His  Asp  Gly  Ile  Gln  Pro  Val  Ala  Ala  Ile
               565                        570                        575
Asp  Ser  Asn  Phe  Ala  Ser  Phe  Thr  Tyr  Thr  Pro  Arg  Ser  Leu  Pro  Glu
               580                        585                   590
Asp  Asp  Thr  Ser  Met  Ala  Ile  Leu  Ser  Met  Leu  Gln  Asp  Met  Asn  Phe
               595                        600                   605
Ile  Asn  Asn  Tyr  Lys  Ile  Asp  Cys  Pro  Thr  Leu  Ala  Arg  Phe  Cys  Leu
     610                        615                   620
Met  Val  Lys  Lys  Gly  Tyr  Arg  Asp  Pro  Pro  Tyr  His  Asn  Trp  Met  His
625                        630                        635                   640
Ala  Phe  Ser  Val  Ser  His  Phe  Cys  Tyr  Leu  Leu  Tyr  Lys  Asn  Leu  Glu
                    645                        650                        655
Leu  Thr  Asn  Tyr  Leu  Glu  Asp  Met  Glu  Ile  Phe  Ala  Leu  Phe  Ile  Ser
               660                        665                        670
Cys  Met  Cys  His  Asp  Leu  Asp  His  Arg  Gly  Thr  Asn  Asn  Ser  Phe  Gln
          675                        680                        685
```

| | | | | | | | | | | | | | | |
|---|---|---|---|---|---|---|---|---|---|---|---|---|---|---|
| Val | Ala | Ser | Lys | Ser | Val | Leu | Ala | Ala | Leu | Tyr | Ser | Glu | Gly | Ser |
| 690 | | | | | 695 | | | | | 700 | | | | |
| Val | Met | Glu | Arg | His | His | Phe | Ala | Gln | Ala | Ile | Ala | Ile | Leu | Asn | Thr |
| 705 | | | | | 710 | | | | | 715 | | | | | 720 |
| His | Gly | Cys | Asn | Ile | Phe | Asp | His | Phe | Ser | Arg | Lys | Asp | Tyr | Gln | Arg |
| | | | | 725 | | | | | 730 | | | | | 735 | |
| Met | Leu | Asp | Leu | Met | Arg | Asp | Ile | Ile | Leu | Ala | Thr | Asp | Leu | Ala | His |
| | | | 740 | | | | | 745 | | | | | 750 | | |
| His | Leu | Arg | Ile | Phe | Lys | Asp | Leu | Gln | Lys | Met | Ala | Glu | Val | Gly | Tyr |
| | | 755 | | | | | 760 | | | | | 765 | | | |
| Asp | Arg | Thr | Asn | Lys | Gln | His | His | Ser | Leu | Leu | Leu | Cys | Leu | Leu | Met |
| | 770 | | | | | 775 | | | | | 780 | | | | |
| Thr | Ser | Cys | Asp | Leu | Ser | Asp | Gln | Thr | Lys | Gly | Trp | Lys | Thr | Thr | Arg |
| 785 | | | | | 790 | | | | | 795 | | | | | 800 |
| Lys | Ile | Ala | Glu | Leu | Ile | Tyr | Lys | Glu | Phe | Phe | Ser | Gln | Gly | Asp | Leu |
| | | | | 805 | | | | | 810 | | | | | 815 | |
| Glu | Lys | Ala | Met | Gly | Asn | Arg | Pro | Met | Glu | Met | Met | Asp | Arg | Glu | Lys |
| | | | 820 | | | | | 825 | | | | | 830 | | |
| Ala | Tyr | Ile | Pro | Glu | Leu | Gln | Ile | Ser | Phe | Met | Glu | His | Ile | Ala | Met |
| | | 835 | | | | | 840 | | | | | 845 | | | |
| Pro | Ile | Tyr | Lys | Leu | Leu | Gln | Asp | Leu | Phe | Pro | Lys | Ala | Ala | Glu | Leu |
| | 850 | | | | | 855 | | | | | 860 | | | | |
| Tyr | Glu | Arg | Val | Ala | Ser | Asn | Arg | Glu | His | Trp | Thr | Lys | Val | Ser | His |
| 865 | | | | | 870 | | | | | 875 | | | | | 880 |
| Lys | Phe | Thr | Ile | Arg | Gly | Leu | Pro | Ser | Asn | Asn | Ser | Leu | Asp | Phe | Leu |
| | | | | 885 | | | | | 890 | | | | | 895 | |
| Asp | Glu | Glu | Tyr | Glu | Val | Pro | Asp | Leu | Asp | Gly | Ala | Arg | Ala | Pro | Ile |
| | | | 900 | | | | | 905 | | | | | 910 | | |
| Asn | Gly | Cys | Cys | Ser | Leu | Asp | Ala | Glu | | | | | | | |
| | | 915 | | | | | 920 | | | | | | | | |

( 2 ) INFORMATION FOR SEQ ID NO:40:

( i ) SEQUENCE CHARACTERISTICS:
        ( A ) LENGTH: 249 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:40:

| | | | | | |
|---|---|---|---|---|---|
| ATATCGAATT | CGGTTTAGTC | TGGTTGGGGA | GGCAGACGAT | GAGGAGCGAT | GGGGCAGGCA | 60 |
| TGCGGCCACT | CCATCCTCTG | CAGGAGCCAG | CAGTACCCGG | CTGCGCGACC | GGCTGAGCCG | 120 |
| CGGGGCCAGC | AGGTCTTCCT | CAAGCCGGAC | GAGCCGCCGC | CGCCGCCGCA | GCCATGCGCC | 180 |
| GACAGCCTGC | AGGATGCTTT | GCTGAGCCTG | GGCTCCGTCA | TTGAGCTTGC | AGGCTTGCGA | 240 |
| CAGGCTGTC | | | | | | 249 |

( 2 ) INFORMATION FOR SEQ ID NO:41:

( i ) SEQUENCE CHARACTERISTICS:
        ( A ) LENGTH: 250 base pairs
        ( B ) TYPE: nucleic acid
        ( C ) STRANDEDNESS: single
        ( D ) TOPOLOGY: linear ( i i ) MOLECULE TYPE: cDNA ( i v ) ANTI-SENSE: YES ( x i ) SEQUENCE DESCRIPTION: SEQ ID NO:41:

| | | | | | |
|---|---|---|---|---|---|
| GAATTCGGGT | AGAGCAGGTA | GCAGAAGTGG | GAGACAGAAA | AGGCGTGCAT | CCAGTTGTGG | 60
| TAGGGGGGAT | CCCGGTAGCC | CTTCTTCACC | ATCAAACAGA | ACCGGGCCAG | TGTCGGGCAG | 120
| TCAATTTTGT | AGTTATTGAT | GAAATTCATG | TTCTGCAGCA | TGCTCAGGAT | GGCCATGGAG | 180
| TGTCATCCTT | GGGCAGAGAG | CGAGGAGTGT | ATGTGAACTG | GCAAGTTGGA | GTCGATGGCA | 240
| GCCACAGGCT | | | | | | 250

( 2 ) INFORMATION FOR SEQ ID NO:42:

( i ) SEQUENCE CHARACTERISTICS:
        ( A ) LENGTH: 3789 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 181..3006

( x i ) SEQUENCE DESCRIPTION: SEQ ID NO:42:

| | | | | | |
|---|---|---|---|---|---|
| GCGGGAACTG | CCAGGGCAGC | AGGGCTGGAT | TGGGGTGTTG | AGTCCAGGCT | GAGTCGGGGA | 60
| CAGGCCACTG | TTCTTGGTCC | CCGTGCCTGC | TGGGCCAGGC | GCCCTGCCTG | GAGCCCCGGG | 120
| CAGGGTGGAC | AGGGTGAGGT | GCCACTTTAG | TCTGGTTGGG | GAGGCAGACG | ATGAGGAGCG | 180

| ATG Met 1 | GGG Gly | CAG Gln | GCA Ala | TGC Cys 5 | GGC Gly | CAC His | TCC Ser | ATC Ile | CTC Leu 10 | TGC Cys | AGG Arg | AGC Ser | CAG Gln | CAG Gln 15 | TAC Tyr | 228 |
| CCG Pro | GCT Ala | GCG Ala | CGA Arg 20 | CCG Pro | GCT Ala | GAG Glu | CCG Pro | CGG Arg 25 | GGC Gly | CAG Gln | CAG Gln | GTC Val | TTC Phe 30 | CTC Leu | AAG Lys | 276 |
| CCG Pro | GAC Asp | GAG Glu 35 | CCG Pro | CCG Pro | CCG Pro | CCG Pro | CAG Gln 40 | CCA Pro | TGC Cys | GCC Ala | GAC Asp | AGC Ser 45 | CTG Leu | CAG Gln | | 324 |
| GAT Asp | GCT Ala 50 | TTG Leu | CTG Leu | AGC Ser | CTG Leu | GGC Gly 55 | TCC Ser | GTC Val | ATT Ile | GAC Asp | GTT Val 60 | GCA Ala | GGC Gly | TTG Leu | CAA Gln | 372 |
| CAG Gln 65 | GCT Ala | GTC Val | AAG Lys | GAG Glu | GCC Ala 70 | CTG Leu | TCG Ser | GCT Ala | GTG Val | CTT Leu 75 | CCC Pro | AAA Lys | GTG Val | GAG Glu | ACG Thr 80 | 420 |
| GTC Val | TAC Tyr | ACC Thr | TAC Tyr | CTG Leu 85 | CTG Leu | GAT Asp | GGG Gly | GAA Glu | TCC Ser 90 | CGG Arg | CTG Leu | GTG Val | TGT Cys | GAG Glu 95 | GAG Glu | 468 |
| CCC Pro | CCC Pro | CAC His | GAG Glu 100 | CTG Leu | CCC Pro | CAG Gln | GAG Glu | GGG Gly 105 | AAA Lys | GTG Val | CGA Arg | GAG Glu | GCT Ala 110 | GTG Val | ATC Ile | 516 |
| TCC Ser | CGG Arg | AAG Lys 115 | CGG Arg | CTG Leu | GGC Gly | TGC Cys | AAT Asn 120 | GGA Gly | CTG Leu | GGC Gly | CCC Pro | TCA Ser 125 | GAC Asp | CTG Leu | CCT Pro | 564 |
| GGG Gly | AAG Lys 130 | CCC Pro | TTG Leu | GCA Ala | AGG Arg | CTG Leu 135 | GTG Val | GCT Ala | CCA Pro | CTG Leu | GCT Ala 140 | CCT Pro | GAC Asp | ACC Thr | CAA Gln | 612 |
| GTG Val 145 | CTG Leu | GTC Val | ATA Ile | CCG Pro | CTG Leu 150 | GTG Val | GAC Asp | AAG Lys | GAG Glu | GCC Ala 155 | GGG Gly | GCT Ala | GTG Val | GCA Ala | GCT Ala 160 | 660 |
| GTC Val | ATC Ile | TTG Leu | GTG Val | CAC His 165 | TGT Cys | GGT Gly | CAG Gln | CTG Leu | AGT Ser 170 | GAC Asp | AAT Asn | GAG Glu | GAG Glu | TGG Trp 175 | AGC Ser | 708 |

| | | | | | | | | | | | | | | | | |
|---|---|---|---|---|---|---|---|---|---|---|---|---|---|---|---|---|
| CTG | CAA | GCT | GTG | GAG | AAG | CAT | ACC | CTG | GTG | GCC | CTG | AAA | AGG | GTG | CAG | 756 |
| Leu | Gln | Ala | Val | Glu | Lys | His | Thr | Leu | Val | Ala | Leu | Lys | Arg | Val | Gln | |
| | | | 180 | | | | 185 | | | | | | 190 | | | |
| GCC | TTG | CAG | CAG | CGC | GAG | TCC | AGC | GTG | GCC | CCG | GAA | GCG | ACC | CAG | AAT | 804 |
| Ala | Leu | Gln | Gln | Arg | Glu | Ser | Ser | Val | Ala | Pro | Glu | Ala | Thr | Gln | Asn | |
| | | | 195 | | | | 200 | | | | | | 205 | | | |
| CCT | CCG | GAG | GAG | GCA | GCG | GGA | GAC | CAG | AAG | GGT | GGG | GTC | GCA | TAC | ACA | 852 |
| Pro | Pro | Glu | Glu | Ala | Ala | Gly | Asp | Gln | Lys | Gly | Gly | Val | Ala | Tyr | Thr | |
| | 210 | | | | | 215 | | | | | 220 | | | | | |
| GAC | CAA | GAC | CGA | AAG | ATC | CTG | CAG | CTT | TGC | GGG | GAG | CTC | TAC | GAC | CTG | 900 |
| Asp | Gln | Asp | Arg | Lys | Ile | Leu | Gln | Leu | Cys | Gly | Glu | Leu | Tyr | Asp | Leu | |
| 225 | | | | | 230 | | | | 235 | | | | | 240 | | |
| GAT | GCA | TCT | TCC | CTG | CAG | CTC | AAA | GTC | CTC | CAA | TAT | CTG | CAA | CAG | GAG | 948 |
| Asp | Ala | Ser | Ser | Leu | Gln | Leu | Lys | Val | Leu | Gln | Tyr | Leu | Gln | Gln | Glu | |
| | | | | 245 | | | | | 250 | | | | | 255 | | |
| ACC | CAG | GCA | TCC | CGC | TGC | TGC | CTG | CTG | CTG | GTA | TCC | GAG | GAC | AAT | CTT | 996 |
| Thr | Gln | Ala | Ser | Arg | Cys | Cys | Leu | Leu | Leu | Val | Ser | Glu | Asp | Asn | Leu | |
| | | | 260 | | | | | 265 | | | | | 270 | | | |
| CAG | CTC | TCC | TGC | AAG | GTC | ATT | GGA | GAT | AAA | GTA | CTG | GAG | GAA | GAG | ATC | 1044 |
| Gln | Leu | Ser | Cys | Lys | Val | Ile | Gly | Asp | Lys | Val | Leu | Glu | Glu | Glu | Ile | |
| | | 275 | | | | | 280 | | | | | 285 | | | | |
| AGC | TTT | CCG | TTG | ACC | ACA | GGA | CGC | CTG | GGC | CAA | GTG | GTG | GAA | GAC | AAG | 1092 |
| Ser | Phe | Pro | Leu | Thr | Thr | Gly | Arg | Leu | Gly | Gln | Val | Val | Glu | Asp | Lys | |
| | 290 | | | | | 295 | | | | | 300 | | | | | |
| AAG | TCT | ATC | CAG | CTG | AAA | GAT | CTC | ACC | TCC | GAG | GAT | ATG | CAA | CAG | CTG | 1140 |
| Lys | Ser | Ile | Gln | Leu | Lys | Asp | Leu | Thr | Ser | Glu | Asp | Met | Gln | Gln | Leu | |
| 305 | | | | | 310 | | | | | 315 | | | | | 320 | |
| CAA | AGC | ATG | TTG | GGC | TGT | GAG | GTG | CAG | GCC | ATG | CTC | TGT | GTC | CCT | GTC | 1188 |
| Gln | Ser | Met | Leu | Gly | Cys | Glu | Val | Gln | Ala | Met | Leu | Cys | Val | Pro | Val | |
| | | | | 325 | | | | | 330 | | | | | 335 | | |
| ATC | AGC | CGG | GCC | ACT | GAC | CAG | GTC | GTG | GCC | CTG | GCC | TGT | GCC | TTC | AAC | 1236 |
| Ile | Ser | Arg | Ala | Thr | Asp | Gln | Val | Val | Ala | Leu | Ala | Cys | Ala | Phe | Asn | |
| | | | 340 | | | | | 345 | | | | | 350 | | | |
| AAG | CTC | GGA | GGA | GAC | TTG | TTC | ACA | GAC | CAG | GAC | GAG | CAC | GTG | ATC | CAG | 1284 |
| Lys | Leu | Gly | Gly | Asp | Leu | Phe | Thr | Asp | Gln | Asp | Glu | His | Val | Ile | Gln | |
| | | 355 | | | | | 360 | | | | | 365 | | | | |
| CAC | TGC | TTC | CAC | TAC | ACC | AGC | ACA | GTG | CTC | ACC | AGC | ACC | CTG | GCC | TTC | 1332 |
| His | Cys | Phe | His | Tyr | Thr | Ser | Thr | Val | Leu | Thr | Ser | Thr | Leu | Ala | Phe | |
| | 370 | | | | | 375 | | | | | 380 | | | | | |
| CAG | AAG | GAG | CAG | AAG | CTC | AAG | TGT | GAG | TGC | CAG | GCT | CTT | CTC | CAA | GTG | 1380 |
| Gln | Lys | Glu | Gln | Lys | Leu | Lys | Cys | Glu | Cys | Gln | Ala | Leu | Leu | Gln | Val | |
| 385 | | | | | 390 | | | | | 395 | | | | | 400 | |
| GCG | AAG | AAC | CTC | TTC | ACT | CAT | CTG | GAT | GAC | GTC | TCC | GTG | CTG | CTC | CAG | 1428 |
| Ala | Lys | Asn | Leu | Phe | Thr | His | Leu | Asp | Asp | Val | Ser | Val | Leu | Leu | Gln | |
| | | | | 405 | | | | | 410 | | | | | 415 | | |
| GAG | ATC | ATC | ACA | GAG | GCC | AGG | AAC | CTC | AGC | AAT | GCT | GAG | ATC | TGC | TCT | 1476 |
| Glu | Ile | Ile | Thr | Glu | Ala | Arg | Asn | Leu | Ser | Asn | Ala | Glu | Ile | Cys | Ser | |
| | | | 420 | | | | | 425 | | | | | 430 | | | |
| GTG | TTC | CTG | CTG | GAT | CAG | AAC | GAG | CTG | GTG | GCC | AAG | GTG | TTC | GAT | GGG | 1524 |
| Val | Phe | Leu | Leu | Asp | Gln | Asn | Glu | Leu | Val | Ala | Lys | Val | Phe | Asp | Gly | |
| | | 435 | | | | | 440 | | | | | 445 | | | | |
| GGT | GTG | GTG | GAA | GAT | GAG | AGC | TAT | GAG | ATC | CGC | ATT | CCC | GCT | GAC | CAG | 1572 |
| Gly | Val | Val | Glu | Asp | Glu | Ser | Tyr | Glu | Ile | Arg | Ile | Pro | Ala | Asp | Gln | |
| | 450 | | | | | 455 | | | | | 460 | | | | | |
| GGC | ATC | GCG | GGT | CAT | GTG | GCG | ACC | ACC | GGC | CAG | ATC | CTA | AAC | ATC | CCA | 1620 |
| Gly | Ile | Ala | Gly | His | Val | Ala | Thr | Thr | Gly | Gln | Ile | Leu | Asn | Ile | Pro | |
| 465 | | | | | 470 | | | | | 475 | | | | | 480 | |
| GAT | GCT | TAC | GCA | CAT | CCG | CTT | TTC | TAC | CGA | GGC | GTG | GAC | GAC | AGC | ACC | 1668 |
| Asp | Ala | Tyr | Ala | His | Pro | Leu | Phe | Tyr | Arg | Gly | Val | Asp | Asp | Ser | Thr | |
| | | | | 485 | | | | | 490 | | | | | 495 | | |

```
GGC  TTC  CGG  ACG  CGC  AAC  ATC  CTC  TGC  TTC  CCC  ATC  AAG  AAC  GAG  AAC    1716
Gly  Phe  Arg  Thr  Arg  Asn  Ile  Leu  Cys  Phe  Pro  Ile  Lys  Asn  Glu  Asn
               500                      505                      510

CAG  GAG  GTC  ATC  GGT  GTG  GCC  GAG  CTG  GTG  AAC  AAG  ATC  AAT  GGA  CCA    1764
Gln  Glu  Val  Ile  Gly  Val  Ala  Glu  Leu  Val  Asn  Lys  Ile  Asn  Gly  Pro
               515                      520                      525

TGG  TTC  AGC  AAG  TTT  GAT  GAA  GAC  CTG  GCT  ACA  GCC  TTC  TCC  ATC  TAC    1812
Trp  Phe  Ser  Lys  Phe  Asp  Glu  Asp  Leu  Ala  Thr  Ala  Phe  Ser  Ile  Tyr
     530                      535                      540

TGT  GGC  ATC  AGC  ATT  GCC  CAT  TCC  CTC  CTA  TAC  AAG  AAA  GTG  AAT  GAG    1860
Cys  Gly  Ile  Ser  Ile  Ala  His  Ser  Leu  Leu  Tyr  Lys  Lys  Val  Asn  Glu
545                      550                      555                      560

GCG  CAG  TAT  CGC  AGC  CAC  CTT  GCC  AAT  GAG  ATG  ATG  ATG  TAC  CAC  ATG    1908
Ala  Gln  Tyr  Arg  Ser  His  Leu  Ala  Asn  Glu  Met  Met  Met  Tyr  His  Met
                    565                      570                      575

AAG  GTC  TCT  GAT  GAC  GAG  TAC  ACC  AAA  CTT  CTC  CAT  GAC  GGG  ATC  CAG    1956
Lys  Val  Ser  Asp  Asp  Glu  Tyr  Thr  Lys  Leu  Leu  His  Asp  Gly  Ile  Gln
               580                      585                      590

CCT  GTG  GCT  GCC  ATC  GAC  TCC  AAC  TTT  GCC  AGT  TTC  ACA  TAC  ACT  CCT    2004
Pro  Val  Ala  Ala  Ile  Asp  Ser  Asn  Phe  Ala  Ser  Phe  Thr  Tyr  Thr  Pro
               595                      600                      605

CGC  TCT  CTG  CCC  GAG  GAT  GAC  ACT  TCC  ATG  GCC  ATC  CTG  AGC  ATG  CTG    2052
Arg  Ser  Leu  Pro  Glu  Asp  Asp  Thr  Ser  Met  Ala  Ile  Leu  Ser  Met  Leu
     610                      615                      620

CAG  GAC  ATG  AAT  TTC  ATC  AAT  AAC  TAC  AAA  ATT  GAC  TGC  CCG  ACA  CTG    2100
Gln  Asp  Met  Asn  Phe  Ile  Asn  Asn  Tyr  Lys  Ile  Asp  Cys  Pro  Thr  Leu
625                      630                      635                      640

GCC  CGG  TTC  TGT  TTG  ATG  GTG  AAG  AAG  GGC  TAC  CGG  GAT  CCC  CCC  TAC    2148
Ala  Arg  Phe  Cys  Leu  Met  Val  Lys  Lys  Gly  Tyr  Arg  Asp  Pro  Pro  Tyr
               645                      650                      655

CAC  AAC  TGG  ATG  CAC  GCC  TTT  TCT  GTC  TCC  CAC  TTC  TGC  TAC  CTG  CTC    2196
His  Asn  Trp  Met  His  Ala  Phe  Ser  Val  Ser  His  Phe  Cys  Tyr  Leu  Leu
               660                      665                      670

TAC  AAG  AAC  CTG  GAG  CTC  ACC  AAC  TAC  CTC  GAG  GAC  ATG  GAG  ATC  TTT    2244
Tyr  Lys  Asn  Leu  Glu  Leu  Thr  Asn  Tyr  Leu  Glu  Asp  Met  Glu  Ile  Phe
          675                      680                      685

GCC  TTG  TTT  ATT  TCC  TGC  ATG  TGT  CAC  GAC  CTG  GAC  CAC  AGA  GGC  ACA    2292
Ala  Leu  Phe  Ile  Ser  Cys  Met  Cys  His  Asp  Leu  Asp  His  Arg  Gly  Thr
     690                      695                      700

AAC  AAC  TCC  TTC  CAG  GTG  GCC  TCG  AAA  TCT  GTG  CTG  GCC  GCG  CTC  TAC    2340
Asn  Asn  Ser  Phe  Gln  Val  Ala  Ser  Lys  Ser  Val  Leu  Ala  Ala  Leu  Tyr
705                      710                      715                      720

AGC  TCG  GAA  GGC  TCT  GTC  ATG  GAG  AGG  CAC  CAC  TTC  GCT  CAG  GCC  ATT    2388
Ser  Ser  Glu  Gly  Ser  Val  Met  Glu  Arg  His  His  Phe  Ala  Gln  Ala  Ile
               725                      730                      735

GCC  ATC  CTC  AAC  ACC  CAC  GGC  TGC  AAC  ATC  TTT  GAC  CAC  TTC  TCC  CGG    2436
Ala  Ile  Leu  Asn  Thr  His  Gly  Cys  Asn  Ile  Phe  Asp  His  Phe  Ser  Arg
               740                      745                      750

AAG  GAT  TAT  CAG  CGC  ATG  TTG  GAC  CTG  ATG  CGG  GAC  ATC  ATC  TTG  GCC    2484
Lys  Asp  Tyr  Gln  Arg  Met  Leu  Asp  Leu  Met  Arg  Asp  Ile  Ile  Leu  Ala
          755                      760                      765

ACA  GAT  CTG  GCC  CAC  CAC  CTC  CGC  ATC  TTC  AAG  GAC  CTC  CAA  AAG  ATG    2532
Thr  Asp  Leu  Ala  His  His  Leu  Arg  Ile  Phe  Lys  Asp  Leu  Gln  Lys  Met
     770                      775                      780

GCC  GAA  GTG  GGC  TAT  GAT  CGA  ACC  AAC  AAG  CAG  CAC  CAC  AGC  CTC  CTT    2580
Ala  Glu  Val  Gly  Tyr  Asp  Arg  Thr  Asn  Lys  Gln  His  His  Ser  Leu  Leu
785                      790                      795                      800

CTC  TGC  CTC  CTT  ATG  ACC  TCC  TGT  GAC  CTC  TCT  GAC  CAG  ACC  AAG  GGC    2628
Leu  Cys  Leu  Leu  Met  Thr  Ser  Cys  Asp  Leu  Ser  Asp  Gln  Thr  Lys  Gly
               805                      810                      815
```

| | | | | | | | | | | | | | | | | |
|---|---|---|---|---|---|---|---|---|---|---|---|---|---|---|---|---|
| TGG | AAG | ACC | ACG | AGG | AAG | ATC | GCG | GAG | CTG | ATC | TAC | AAA | GAG | TTC | TTC | 2676 |
| Trp | Lys | Thr | Thr | Arg | Lys | Ile | Ala | Glu | Leu | Ile | Tyr | Lys | Glu | Phe | Phe | |
| | | | 820 | | | | | 825 | | | | | 830 | | | |
| TCC | CAG | GGA | GAC | TTG | GAG | AAG | GCC | ATG | GGC | AAC | AGG | CCG | ATG | GAG | ATG | 2724 |
| Ser | Gln | Gly | Asp | Leu | Glu | Lys | Ala | Met | Gly | Asn | Arg | Pro | Met | Glu | Met | |
| | | | 835 | | | | 840 | | | | | 845 | | | | |
| ATG | GAC | CGT | GAG | AAG | GCC | TAC | ATC | CCC | GAG | CTG | CAG | ATC | AGC | TTC | ATG | 2772 |
| Met | Asp | Arg | Glu | Lys | Ala | Tyr | Ile | Pro | Glu | Leu | Gln | Ile | Ser | Phe | Met | |
| | 850 | | | | | 855 | | | | | 860 | | | | | |
| GAG | CAC | ATC | GCA | ATG | CCC | ATC | TAC | AAG | CTG | CTG | CAA | GAC | CTG | TTC | CCC | 2820 |
| Glu | His | Ile | Ala | Met | Pro | Ile | Tyr | Lys | Leu | Leu | Gln | Asp | Leu | Phe | Pro | |
| 865 | | | | | 870 | | | | | 875 | | | | | 880 | |
| AAG | GCG | GCC | GAG | TTG | TAC | GAA | CGC | GTG | GCC | TCT | AAT | CGT | GAG | CAC | TGG | 2868 |
| Lys | Ala | Ala | Glu | Leu | Tyr | Glu | Arg | Val | Ala | Ser | Asn | Arg | Glu | His | Trp | |
| | | | | 885 | | | | | 890 | | | | | 895 | | |
| ACC | AAG | GTG | TCA | CAC | AAG | TTC | ACC | ATC | CGA | GGC | CTC | CCG | AGC | AAC | AAC | 2916 |
| Thr | Lys | Val | Ser | His | Lys | Phe | Thr | Ile | Arg | Gly | Leu | Pro | Ser | Asn | Asn | |
| | | | 900 | | | | | 905 | | | | | 910 | | | |
| TCG | TTG | GAC | TTC | CTG | GAC | GAG | GAG | TAT | GAG | GTG | CCT | GAC | CTG | GAT | GGC | 2964 |
| Ser | Leu | Asp | Phe | Leu | Asp | Glu | Glu | Tyr | Glu | Val | Pro | Asp | Leu | Asp | Gly | |
| | | | 915 | | | | | 920 | | | | | 925 | | | |
| GCT | AGG | GCT | CCC | ATC | AAT | GGC | TGT | TGC | AGC | CTT | GAT | GCT | GAG | | | 3006 |
| Ala | Arg | Ala | Pro | Ile | Asn | Gly | Cys | Cys | Ser | Leu | Asp | Ala | Glu | | | |
| | | 930 | | | | | 935 | | | | | 940 | | | | |

| | | | | | |
|---|---|---|---|---|---|
| TGAGTCCCTC | CTGGGACCCC | TCCCTGTCCA | GGCCTCCTCC | CACAAGCCTC | CACGGGCCTG | 3066 |
| GCCGCACGCC | CTGGGACCAG | AGCCAAGGGT | CCTGGATTCT | AGGCCAGGAC | TTCCCATGTG | 3126 |
| ACCCGGGCGA | GGTCTGACCT | TCCCGGGCCT | CAGCTTTCTT | GTCTGTATAA | TGGAAGACTT | 3186 |
| CAGCCTCACT | GAGACTTTGT | CACTTGTCCT | CTGAGAGCAC | AGGGGTAACC | AATGAGCAGT | 3246 |
| GGACCCTGCT | CTGCACCTCT | GACCGCATCT | TGGCAAGTCC | CCACCCTCCA | GGCCACTCCT | 3306 |
| TCTCTGAGGC | AGCCGGATGG | TTTCTTCTGG | GCCCCATTCC | TGCCCTACCA | GACCTGTGCC | 3366 |
| CTTTCCTGTG | GGGCACCCT | CACTGGCTCC | CAGGATCCTC | AGGCAAGAAC | ATGAGACATC | 3426 |
| TGAGTGGGCA | AAGGGTGGGT | CTTAGAGACA | GTTATCAGCC | TGGCTGGAGG | ACTAGAAGTA | 3486 |
| GCCATGGGAC | CACCTGTGGC | CCAGAGGACT | GCCTTTGTAC | TTATGGTGGG | GACTGGGACC | 3546 |
| TGGGGATATA | AGGGTCCCAG | GAGGACACTG | CCAGGGGGCC | AGTGCAGTGC | TCTGGGGAGA | 3606 |
| GGGGGCTCAG | GAAGAGAGGA | GGATAAGAAC | AGTGAGAAGG | AAGGATCCCT | GGGTTGGGAG | 3666 |
| GCAGGCCCAG | CATGGGTCAG | CCATGCTTCC | TCCTGGCTGT | GTGACCCTGG | GCAAGTCCCT | 3726 |
| TCCCCTCTCT | GCGAAACAGT | AGGGTGAGAC | AATCCATTCT | CTAAGACCCC | TTTTAGATCC | 3786 |
| AAG | | | | | | 3789 |

( 2 ) INFORMATION FOR SEQ ID NO:43:

( i ) SEQUENCE CHARACTERISTICS:
        ( A ) LENGTH: 942 amino acids
        ( B ) TYPE: amino acid
        ( D ) TOPOLOGY: linear ( i i ) MOLECULE TYPE: protein ( x i ) SEQUENCE DESCRIPTION: SEQ ID NO:43:

| | | | | | | | | | | | | | | |
|---|---|---|---|---|---|---|---|---|---|---|---|---|---|---|
| Met | Gly | Gln | Ala | Cys | Gly | His | Ser | Ile | Leu | Cys | Arg | Ser | Gln | Gln | Tyr |
| 1 | | | | 5 | | | | | 10 | | | | | 15 | |
| Pro | Ala | Ala | Arg | Pro | Ala | Glu | Pro | Arg | Gly | Gln | Gln | Val | Phe | Leu | Lys |
| | | | 20 | | | | | 25 | | | | | 30 | | |
| Pro | Asp | Glu | Pro | Pro | Pro | Pro | Gln | Pro | Cys | Ala | Asp | Ser | Leu | Gln | |
| | | 35 | | | | | 40 | | | | | 45 | | | |

```
Asp  Ala  Leu  Leu  Ser  Leu  Gly  Ser  Val  Ile  Asp  Val  Ala  Gly  Leu  Gln
      50                  55                  60
Gln  Ala  Val  Lys  Glu  Ala  Leu  Ser  Ala  Val  Leu  Pro  Lys  Val  Glu  Thr
 65                  70                  75                             80
Val  Tyr  Thr  Tyr  Leu  Leu  Asp  Gly  Glu  Ser  Arg  Leu  Val  Cys  Glu  Glu
                     85                  90                             95
Pro  Pro  His  Glu  Leu  Pro  Gln  Glu  Gly  Lys  Val  Arg  Glu  Ala  Val  Ile
              100                 105                      110
Ser  Arg  Lys  Arg  Leu  Gly  Cys  Asn  Gly  Leu  Gly  Pro  Ser  Asp  Leu  Pro
              115                 120                      125
Gly  Lys  Pro  Leu  Ala  Arg  Leu  Val  Ala  Pro  Leu  Ala  Pro  Asp  Thr  Gln
              130                 135                      140
Val  Leu  Val  Ile  Pro  Leu  Val  Asp  Lys  Glu  Ala  Gly  Ala  Val  Ala  Ala
145                       150                      155                      160
Val  Ile  Leu  Val  His  Cys  Gly  Gln  Leu  Ser  Asp  Asn  Glu  Glu  Trp  Ser
                    165                       170                      175
Leu  Gln  Ala  Val  Glu  Lys  His  Thr  Leu  Val  Ala  Leu  Lys  Arg  Val  Gln
                    180                       185                      190
Ala  Leu  Gln  Gln  Arg  Glu  Ser  Ser  Val  Ala  Pro  Glu  Ala  Thr  Gln  Asn
              195                 200                      205
Pro  Pro  Glu  Glu  Ala  Ala  Gly  Asp  Gln  Lys  Gly  Gly  Val  Ala  Tyr  Thr
     210                      215                      220
Asp  Gln  Asp  Arg  Lys  Ile  Leu  Gln  Leu  Cys  Gly  Glu  Leu  Tyr  Asp  Leu
225                      230                 235                           240
Asp  Ala  Ser  Ser  Leu  Gln  Leu  Lys  Val  Leu  Gln  Tyr  Leu  Gln  Gln  Glu
               245                       250                           255
Thr  Gln  Ala  Ser  Arg  Cys  Cys  Leu  Leu  Val  Ser  Glu  Asp  Asn  Leu
              260                 265                      270
Gln  Leu  Ser  Cys  Lys  Val  Ile  Gly  Asp  Lys  Val  Leu  Glu  Glu  Glu  Ile
         275                      280                      285
Ser  Phe  Pro  Leu  Thr  Thr  Gly  Arg  Leu  Gly  Gln  Val  Val  Glu  Asp  Lys
     290                      295                      300
Lys  Ser  Ile  Gln  Leu  Lys  Asp  Leu  Thr  Ser  Glu  Asp  Met  Gln  Gln  Leu
305                      310                      315                      320
Gln  Ser  Met  Leu  Gly  Cys  Glu  Val  Gln  Ala  Met  Leu  Cys  Val  Pro  Val
              325                 330                      335
Ile  Ser  Arg  Ala  Thr  Asp  Gln  Val  Val  Ala  Leu  Ala  Cys  Ala  Phe  Asn
              340                 345                      350
Lys  Leu  Gly  Gly  Asp  Leu  Phe  Thr  Asp  Gln  Asp  Glu  His  Val  Ile  Gln
              355                 360                      365
His  Cys  Phe  His  Tyr  Thr  Ser  Thr  Val  Leu  Thr  Ser  Thr  Leu  Ala  Phe
     370                      375                      380
Gln  Lys  Glu  Gln  Lys  Leu  Lys  Cys  Glu  Cys  Gln  Ala  Leu  Leu  Gln  Val
385                      390                      395                      400
Ala  Lys  Asn  Leu  Phe  Thr  His  Leu  Asp  Asp  Val  Ser  Val  Leu  Leu  Gln
               405                      410                           415
Glu  Ile  Ile  Thr  Glu  Ala  Arg  Asn  Leu  Ser  Asn  Ala  Glu  Ile  Cys  Ser
              420                 425                      430
Val  Phe  Leu  Leu  Asp  Gln  Asn  Glu  Leu  Val  Ala  Lys  Val  Phe  Asp  Gly
     435                      440                      445
Gly  Val  Val  Glu  Asp  Glu  Ser  Tyr  Glu  Ile  Arg  Ile  Pro  Ala  Asp  Gln
     450                      455                      460
Gly  Ile  Ala  Gly  His  Val  Ala  Thr  Thr  Gly  Gln  Ile  Leu  Asn  Ile  Pro
```

|     |     |     |     | 465 |     |     |     |     | 470 |     |     |     |     | 475 |     |     |     |     | 480 |
| --- | --- | --- | --- | --- | --- | --- | --- | --- | --- | --- | --- | --- | --- | --- | --- | --- | --- | --- | --- |
| Asp | Ala | Tyr | Ala | His | Pro | Leu | Phe | Tyr | Arg | Gly | Val | Asp | Asp | Ser | Thr |
|     |     |     |     | 485 |     |     |     |     | 490 |     |     |     |     | 495 |     |
| Gly | Phe | Arg | Thr | Arg | Asn | Ile | Leu | Cys | Phe | Pro | Ile | Lys | Asn | Glu | Asn |
|     |     |     | 500 |     |     |     |     | 505 |     |     |     |     | 510 |     |     |
| Gln | Glu | Val | Ile | Gly | Val | Ala | Glu | Leu | Val | Asn | Lys | Ile | Asn | Gly | Pro |
|     |     |     | 515 |     |     |     | 520 |     |     |     |     | 525 |     |     |     |
| Trp | Phe | Ser | Lys | Phe | Asp | Glu | Asp | Leu | Ala | Thr | Ala | Phe | Ser | Ile | Tyr |
|     | 530 |     |     |     |     | 535 |     |     |     |     | 540 |     |     |     |     |
| Cys | Gly | Ile | Ser | Ile | Ala | His | Ser | Leu | Leu | Tyr | Lys | Lys | Val | Asn | Glu |
| 545 |     |     |     |     | 550 |     |     |     |     | 555 |     |     |     |     | 560 |
| Ala | Gln | Tyr | Arg | Ser | His | Leu | Ala | Asn | Glu | Met | Met | Met | Tyr | His | Met |
|     |     |     |     | 565 |     |     |     |     | 570 |     |     |     |     | 575 |     |
| Lys | Val | Ser | Asp | Asp | Glu | Tyr | Thr | Lys | Leu | Leu | His | Asp | Gly | Ile | Gln |
|     |     |     | 580 |     |     |     |     | 585 |     |     |     |     | 590 |     |     |
| Pro | Val | Ala | Ala | Ile | Asp | Ser | Asn | Phe | Ala | Ser | Phe | Thr | Tyr | Thr | Pro |
|     |     |     | 595 |     |     |     | 600 |     |     |     |     | 605 |     |     |     |
| Arg | Ser | Leu | Pro | Glu | Asp | Asp | Thr | Ser | Met | Ala | Ile | Leu | Ser | Met | Leu |
|     | 610 |     |     |     |     | 615 |     |     |     |     | 620 |     |     |     |     |
| Gln | Asp | Met | Asn | Phe | Ile | Asn | Asn | Tyr | Lys | Ile | Asp | Cys | Pro | Thr | Leu |
| 625 |     |     |     |     | 630 |     |     |     |     | 635 |     |     |     |     | 640 |
| Ala | Arg | Phe | Cys | Leu | Met | Val | Lys | Lys | Gly | Tyr | Arg | Asp | Pro | Pro | Tyr |
|     |     |     |     | 645 |     |     |     |     | 650 |     |     |     |     | 655 |     |
| His | Asn | Trp | Met | His | Ala | Phe | Ser | Val | Ser | His | Phe | Cys | Tyr | Leu | Leu |
|     |     |     | 660 |     |     |     |     | 665 |     |     |     |     | 670 |     |     |
| Tyr | Lys | Asn | Leu | Glu | Leu | Thr | Asn | Tyr | Leu | Glu | Asp | Met | Glu | Ile | Phe |
|     |     | 675 |     |     |     |     | 680 |     |     |     |     | 685 |     |     |     |
| Ala | Leu | Phe | Ile | Ser | Cys | Met | Cys | His | Asp | Leu | Asp | His | Arg | Gly | Thr |
|     | 690 |     |     |     |     | 695 |     |     |     |     | 700 |     |     |     |     |
| Asn | Asn | Ser | Phe | Gln | Val | Ala | Ser | Lys | Ser | Val | Leu | Ala | Ala | Leu | Tyr |
| 705 |     |     |     |     | 710 |     |     |     |     | 715 |     |     |     |     | 720 |
| Ser | Ser | Glu | Gly | Ser | Val | Met | Glu | Arg | His | His | Phe | Ala | Gln | Ala | Ile |
|     |     |     |     | 725 |     |     |     |     | 730 |     |     |     |     | 735 |     |
| Ala | Ile | Leu | Asn | Thr | His | Gly | Cys | Asn | Ile | Phe | Asp | His | Phe | Ser | Arg |
|     |     |     | 740 |     |     |     |     | 745 |     |     |     |     | 750 |     |     |
| Lys | Asp | Tyr | Gln | Arg | Met | Leu | Asp | Leu | Met | Arg | Asp | Ile | Ile | Leu | Ala |
|     |     | 755 |     |     |     |     | 760 |     |     |     |     | 765 |     |     |     |
| Thr | Asp | Leu | Ala | His | His | Leu | Arg | Ile | Phe | Lys | Asp | Leu | Gln | Lys | Met |
|     | 770 |     |     |     |     | 775 |     |     |     |     | 780 |     |     |     |     |
| Ala | Glu | Val | Gly | Tyr | Asp | Arg | Thr | Asn | Lys | Gln | His | His | Ser | Leu | Leu |
| 785 |     |     |     |     | 790 |     |     |     |     | 795 |     |     |     |     | 800 |
| Leu | Cys | Leu | Leu | Met | Thr | Ser | Cys | Asp | Leu | Ser | Asp | Gln | Thr | Lys | Gly |
|     |     |     |     | 805 |     |     |     |     | 810 |     |     |     |     | 815 |     |
| Trp | Lys | Thr | Thr | Arg | Lys | Ile | Ala | Glu | Leu | Ile | Tyr | Lys | Glu | Phe | Phe |
|     |     |     | 820 |     |     |     |     | 825 |     |     |     |     | 830 |     |     |
| Ser | Gln | Gly | Asp | Leu | Glu | Lys | Ala | Met | Gly | Asn | Arg | Pro | Met | Glu | Met |
|     |     | 835 |     |     |     |     | 840 |     |     |     |     | 845 |     |     |     |
| Met | Asp | Arg | Glu | Lys | Ala | Tyr | Ile | Pro | Glu | Leu | Gln | Ile | Ser | Phe | Met |
|     | 850 |     |     |     |     | 855 |     |     |     |     | 860 |     |     |     |     |
| Glu | His | Ile | Ala | Met | Pro | Ile | Tyr | Lys | Leu | Leu | Gln | Asp | Leu | Phe | Pro |
| 865 |     |     |     |     | 870 |     |     |     |     | 875 |     |     |     |     | 880 |
| Lys | Ala | Ala | Glu | Leu | Tyr | Glu | Arg | Val | Ala | Ser | Asn | Arg | Glu | His | Trp |
|     |     |     |     | 885 |     |     |     |     | 890 |     |     |     |     | 895 |     |

| | | | | | | | | | | | | | | |
|---|---|---|---|---|---|---|---|---|---|---|---|---|---|---|
| Thr | Lys | Val | Ser | His | Lys | Phe | Thr | Ile | Arg | Gly | Leu | Pro | Ser | Asn | Asn |
| | | | 900 | | | | 905 | | | | | 910 | | | |
| Ser | Leu | Asp | Phe | Leu | Asp | Glu | Glu | Tyr | Glu | Val | Pro | Asp | Leu | Asp | Gly |
| | | | 915 | | | | 920 | | | | | 925 | | | |
| Ala | Arg | Ala | Pro | Ile | Asn | Gly | Cys | Cys | Ser | Leu | Asp | Ala | Glu | | |
| | | 930 | | | | 935 | | | | | 940 | | | | |

( 2 ) INFORMATION FOR SEQ ID NO:44:

( i ) SEQUENCE CHARACTERISTICS:
        ( A ) LENGTH: 3044 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 12..2834

( x i ) SEQUENCE DESCRIPTION: SEQ ID NO:44:

| | | | | | | | | | | | | | | |
|---|---|---|---|---|---|---|---|---|---|---|---|---|---|---|
| GAATTCTGAT | A | ATG | GGG | CAG | GCA | TGC | GGC | CAC | TCC | ATC | CTC | TGC | AGG | AGC | 50 |
| | | Met | Gly | Gln | Ala | Cys | Gly | His | Ser | Ile | Leu | Cys | Arg | Ser | |
| | | 1 | | | 5 | | | | | 10 | | | | | |
| CAG | CAG | TAC | CCG | GCA | GCG | CGA | CCG | GCT | GAG | CCG | CGG | GGC | CAG | CAG | GTC | 98 |
| Gln | Gln | Tyr | Pro | Ala | Ala | Arg | Pro | Ala | Glu | Pro | Arg | Gly | Gln | Gln | Val |
| | 15 | | | | 20 | | | | | 25 | | | | | |
| TTC | CTC | AAG | CCG | GAC | GAG | CCG | CCG | CCG | CCG | CAG | CCA | TGC | GCC | GAC | 146 |
| Phe | Leu | Lys | Pro | Asp | Glu | Pro | Pro | Pro | Pro | Gln | Pro | Cys | Ala | Asp |
| 30 | | | | 35 | | | | | 40 | | | | | 45 |
| AGC | CTG | CAG | GAC | GCC | TTG | CTG | AGT | CTG | GGC | TCT | GTC | ATC | GAC | ATT | TCA | 194 |
| Ser | Leu | Gln | Asp | Ala | Leu | Leu | Ser | Leu | Gly | Ser | Val | Ile | Asp | Ile | Ser |
| | | | 50 | | | | 55 | | | | | 60 | | | |
| GGC | CTG | CAA | CGT | GCT | GTC | AAG | GAG | GCC | CTG | TCA | GCT | GTG | CTC | CCC | CGA | 242 |
| Gly | Leu | Gln | Arg | Ala | Val | Lys | Glu | Ala | Leu | Ser | Ala | Val | Leu | Pro | Arg |
| | | 65 | | | | 70 | | | | | 75 | | | | |
| GTG | GAA | ACT | GTC | TAC | ACC | TAC | CTA | CTG | GAT | GGT | GAG | TCC | CAG | CTG | GTG | 290 |
| Val | Glu | Thr | Val | Tyr | Thr | Tyr | Leu | Leu | Asp | Gly | Glu | Ser | Gln | Leu | Val |
| | 80 | | | | 85 | | | | | 90 | | | | | |
| TGT | GAG | GAC | CCC | CCA | CAT | GAG | CTG | CCC | CAG | GAG | GGG | AAA | GTC | CGG | GAG | 338 |
| Cys | Glu | Asp | Pro | Pro | His | Glu | Leu | Pro | Gln | Glu | Gly | Lys | Val | Arg | Glu |
| 95 | | | | 100 | | | | | 105 | | | | | | |
| GCT | ATC | ATC | TCC | CAG | AAG | CGG | CTG | GGC | TGC | AAT | GGG | CTG | GGC | TTC | TCA | 386 |
| Ala | Ile | Ile | Ser | Gln | Lys | Arg | Leu | Gly | Cys | Asn | Gly | Leu | Gly | Phe | Ser |
| 110 | | | | 115 | | | | | 120 | | | | | 125 | |
| GAC | CTG | CCA | GGG | AAG | CCC | TTG | GCC | AGG | CTG | GTG | GCT | CCA | CTG | GCT | CCT | 434 |
| Asp | Leu | Pro | Gly | Lys | Pro | Leu | Ala | Arg | Leu | Val | Ala | Pro | Leu | Ala | Pro |
| | | | 130 | | | | 135 | | | | | 140 | | | |
| GAT | ACC | CAA | GTG | CTG | GTC | ATG | CCG | CTA | GCG | GAC | AAG | GAG | GCT | GGG | GCC | 482 |
| Asp | Thr | Gln | Val | Leu | Val | Met | Pro | Leu | Ala | Asp | Lys | Glu | Ala | Gly | Ala |
| | | 145 | | | | 150 | | | | | 155 | | | | |
| GTG | GCA | GCT | GTC | ATC | TTG | GTG | CAC | TGT | GGC | CAG | CTG | AGT | GAT | AAT | GAG | 530 |
| Val | Ala | Ala | Val | Ile | Leu | Val | His | Cys | Gly | Gln | Leu | Ser | Asp | Asn | Glu |
| | | 160 | | | | 165 | | | | | 170 | | | | |
| GAA | TGG | AGC | CTG | CAG | GCG | GTG | GAG | AAG | CAT | ACC | CTG | GTC | GCC | CTG | CGG | 578 |
| Glu | Trp | Ser | Leu | Gln | Ala | Val | Glu | Lys | His | Thr | Leu | Val | Ala | Leu | Arg |
| | 175 | | | | 180 | | | | | 185 | | | | | |
| AGG | GTG | CAG | GTC | CTG | CAG | CAG | CGC | GGG | CCC | AGG | GAG | GCT | CCC | CGA | GCC | 626 |
| Arg | Val | Gln | Val | Leu | Gln | Gln | Arg | Gly | Pro | Arg | Glu | Ala | Pro | Arg | Ala |
| 190 | | | | 195 | | | | | 200 | | | | | 205 | |
| GTC | CAG | AAC | CCC | CCG | GAG | GGG | ACG | GCG | GAA | GAC | CAG | AAG | GGC | GGG | GCG | 674 |
| Val | Gln | Asn | Pro | Pro | Glu | Gly | Thr | Ala | Glu | Asp | Gln | Lys | Gly | Gly | Ala |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 210 |     |     |     |     | 215 |     |     |     |     | 220 |     |      |
| GCG | TAC | ACC | GAC | CGC | GAC | CGC | AAG | ATC | CTC | CAA | CTG | TGC | GGG | GAA | CTC | 722  |
| Ala | Tyr | Thr | Asp | Arg | Asp | Arg | Lys | Ile | Leu | Gln | Leu | Cys | Gly | Glu | Leu |      |
|     |     |     | 225 |     |     |     |     | 230 |     |     |     |     | 235 |     |     |      |
| TAC | GAC | CTG | GAT | GCC | TCT | TCC | CTG | CAG | CTC | AAA | GTG | CTC | CAA | TAC | CTG | 770  |
| Tyr | Asp | Leu | Asp | Ala | Ser | Ser | Leu | Gln | Leu | Lys | Val | Leu | Gln | Tyr | Leu |      |
|     |     |     | 240 |     |     |     |     | 245 |     |     |     |     | 250 |     |     |      |
| CAG | CAG | GAG | ACC | CGG | GCA | TCC | CGC | TGC | TGC | CTC | CTG | CTG | GTG | TCG | GAG | 818  |
| Gln | Gln | Glu | Thr | Arg | Ala | Ser | Arg | Cys | Cys | Leu | Leu | Leu | Val | Ser | Glu |      |
|     |     | 255 |     |     |     |     | 260 |     |     |     |     | 265 |     |     |     |      |
| GAC | AAT | CTC | CAG | CTT | TCT | TGC | AAG | GTC | ATC | GGA | GAC | AAA | GTG | CTC | GGG | 866  |
| Asp | Asn | Leu | Gln | Leu | Ser | Cys | Lys | Val | Ile | Gly | Asp | Lys | Val | Leu | Gly |      |
|     | 270 |     |     |     |     | 275 |     |     |     |     | 280 |     |     |     | 285 |      |
| GAA | GAG | GTC | AGC | TTT | CCC | TTG | ACA | GGA | TGC | CTG | GGC | CAG | GTG | GTG | GAA | 914  |
| Glu | Glu | Val | Ser | Phe | Pro | Leu | Thr | Gly | Cys | Leu | Gly | Gln | Val | Val | Glu |      |
|     |     |     |     |     | 290 |     |     |     | 295 |     |     |     |     | 300 |     |      |
| GAC | AAG | AAG | TCC | ATC | CAG | CTG | AAG | GAC | CTC | ACC | TCC | GAG | GAT | GTA | CAA | 962  |
| Asp | Lys | Lys | Ser | Ile | Gln | Leu | Lys | Asp | Leu | Thr | Ser | Glu | Asp | Val | Gln |      |
|     |     |     | 305 |     |     |     |     | 310 |     |     |     |     | 315 |     |     |      |
| CAG | CTG | CAG | AGC | ATG | TTG | GGC | TGT | GAG | CTG | CAG | GCC | ATG | CTC | TGT | GTC | 1010 |
| Gln | Leu | Gln | Ser | Met | Leu | Gly | Cys | Glu | Leu | Gln | Ala | Met | Leu | Cys | Val |      |
|     |     | 320 |     |     |     |     | 325 |     |     |     |     | 330 |     |     |     |      |
| CCT | GTC | ATC | AGC | CGG | GCC | ACT | GAC | CAG | GTG | GTG | GCC | TTG | GCC | TGC | GCC | 1058 |
| Pro | Val | Ile | Ser | Arg | Ala | Thr | Asp | Gln | Val | Val | Ala | Leu | Ala | Cys | Ala |      |
|     | 335 |     |     |     |     | 340 |     |     |     |     | 345 |     |     |     |     |      |
| TTC | AAC | AAG | CTA | GAA | GGA | GAC | TTG | TTC | ACC | GAC | GAG | GAC | GAG | CAT | GTG | 1106 |
| Phe | Asn | Lys | Leu | Glu | Gly | Asp | Leu | Phe | Thr | Asp | Glu | Asp | Glu | His | Val |      |
| 350 |     |     |     |     | 355 |     |     |     |     | 360 |     |     |     |     | 365 |      |
| ATC | CAG | CAC | TGC | TTC | CAC | TAC | ACC | AGC | ACC | GTG | CTC | ACC | AGC | ACC | CTG | 1154 |
| Ile | Gln | His | Cys | Phe | His | Tyr | Thr | Ser | Thr | Val | Leu | Thr | Ser | Thr | Leu |      |
|     |     |     | 370 |     |     |     |     | 375 |     |     |     |     | 380 |     |     |      |
| GCC | TTC | CAG | AAG | GAA | CAG | AAA | CTC | AAG | TGT | GAG | TGC | CAG | GCT | CTT | CTC | 1202 |
| Ala | Phe | Gln | Lys | Glu | Gln | Lys | Leu | Lys | Cys | Glu | Cys | Gln | Ala | Leu | Leu |      |
|     |     |     | 385 |     |     |     |     | 390 |     |     |     |     | 395 |     |     |      |
| CAA | GTG | GCA | AAG | AAC | CTC | TTC | ACC | CAC | CTG | GAT | GAC | GTC | TCT | GTC | CTG | 1250 |
| Gln | Val | Ala | Lys | Asn | Leu | Phe | Thr | His | Leu | Asp | Asp | Val | Ser | Val | Leu |      |
|     |     | 400 |     |     |     |     | 405 |     |     |     |     | 410 |     |     |     |      |
| CTC | CAG | GAG | ATC | ATC | ACG | GAG | GCC | AGA | AAC | CTC | AGC | AAC | GCA | GAG | ATC | 1298 |
| Leu | Gln | Glu | Ile | Ile | Thr | Glu | Ala | Arg | Asn | Leu | Ser | Asn | Ala | Glu | Ile |      |
| 415 |     |     |     |     | 420 |     |     |     |     | 425 |     |     |     |     |     |      |
| TGC | TCT | GTG | TTC | CTG | CTG | GAT | CAG | AAT | GAG | CTG | GTG | GCC | AAG | GTG | TTC | 1346 |
| Cys | Ser | Val | Phe | Leu | Leu | Asp | Gln | Asn | Glu | Leu | Val | Ala | Lys | Val | Phe |      |
| 430 |     |     |     |     | 435 |     |     |     |     | 440 |     |     |     |     | 445 |      |
| GAC | GGG | GGC | GTG | GTG | GAT | GAT | GAG | AGC | TAT | GAG | ATC | CGC | ATC | CCG | GCC | 1394 |
| Asp | Gly | Gly | Val | Val | Asp | Asp | Glu | Ser | Tyr | Glu | Ile | Arg | Ile | Pro | Ala |      |
|     |     |     |     | 450 |     |     |     |     | 455 |     |     |     |     | 460 |     |      |
| GAT | CAG | GGC | ATC | GCG | GGA | CAC | GTG | GCG | ACC | ACG | GGC | CAG | ATC | CTG | AAC | 1442 |
| Asp | Gln | Gly | Ile | Ala | Gly | His | Val | Ala | Thr | Thr | Gly | Gln | Ile | Leu | Asn |      |
|     |     |     | 465 |     |     |     |     | 470 |     |     |     |     | 475 |     |     |      |
| ATC | CCT | GAC | GCA | TAT | GCC | CAT | CCG | CTT | TTC | TAC | CGC | GGC | GTG | GAC | GAC | 1490 |
| Ile | Pro | Asp | Ala | Tyr | Ala | His | Pro | Leu | Phe | Tyr | Arg | Gly | Val | Asp | Asp |      |
|     |     | 480 |     |     |     |     | 485 |     |     |     |     | 490 |     |     |     |      |
| AGC | ACC | GGC | TTC | CGC | ACG | CGC | AAC | ATC | CTC | TGC | TTC | CCC | ATC | AAG | AAC | 1538 |
| Ser | Thr | Gly | Phe | Arg | Thr | Arg | Asn | Ile | Leu | Cys | Phe | Pro | Ile | Lys | Asn |      |
|     | 495 |     |     |     |     | 500 |     |     |     |     | 505 |     |     |     |     |      |
| GAG | AAC | CAG | GAG | GTC | ATC | GGT | GTG | GCC | GAG | CTG | GTG | AAC | AAG | ATC | AAT | 1586 |
| Glu | Asn | Gln | Glu | Val | Ile | Gly | Val | Ala | Glu | Leu | Val | Asn | Lys | Ile | Asn |      |
| 510 |     |     |     |     | 515 |     |     |     |     | 520 |     |     |     |     | 525 |      |
| GGG | CCA | TGG | TTC | AGC | AAG | TTC | GAC | GAG | GAC | CTG | GCG | ACG | GCC | TTC | TCC | 1634 |
| Gly | Pro | Trp | Phe | Ser | Lys | Phe | Asp | Glu | Asp | Leu | Ala | Thr | Ala | Phe | Ser |      |

|  |  |  |  |  |  |  |  |  |  |  |  |  |  |  |  |
|---|---|---|---|---|---|---|---|---|---|---|---|---|---|---|---|
| ATC | TAC | TGC | GGC | ATC | AGC | ATC | GCC | CAT | TCT | CTC | CTA | TAC | AAA | AAA | GTG |
| Ile | Tyr | Cys | Gly | Ile | Ser | Ile | Ala | His | Ser | Leu | Leu | Tyr | Lys | Lys | Val |
|  |  |  | 545 |  |  |  |  | 550 |  |  |  |  | 555 |  |  |

1682

|  |  |  |  |  |  |  |  |  |  |  |  |  |  |  |  |
|---|---|---|---|---|---|---|---|---|---|---|---|---|---|---|---|
| AAT | GAG | GCT | CAG | TAT | CGC | AGC | CAC | CTG | GCC | AAT | GAG | ATG | ATG | ATG | TAC |
| Asn | Glu | Ala | Gln | Tyr | Arg | Ser | His | Leu | Ala | Asn | Glu | Met | Met | Met | Tyr |
|  |  | 560 |  |  |  |  | 565 |  |  |  |  | 570 |  |  |  |

1730

|  |  |  |  |  |  |  |  |  |  |  |  |  |  |  |  |
|---|---|---|---|---|---|---|---|---|---|---|---|---|---|---|---|
| CAC | ATG | AAG | GTC | TCC | GAC | GAT | GAG | TAT | ACC | AAA | CTT | CTC | CAT | GAT | GGG |
| His | Met | Lys | Val | Ser | Asp | Asp | Glu | Tyr | Thr | Lys | Leu | Leu | His | Asp | Gly |
|  | 575 |  |  |  |  | 580 |  |  |  |  | 585 |  |  |  |  |

1778

|  |  |  |  |  |  |  |  |  |  |  |  |  |  |  |  |
|---|---|---|---|---|---|---|---|---|---|---|---|---|---|---|---|
| ATC | CAG | CCT | GTG | GCT | GCC | ATT | GAC | TCC | AAT | TTT | GCA | AGT | TTC | ACC | TAT |
| Ile | Gln | Pro | Val | Ala | Ala | Ile | Asp | Ser | Asn | Phe | Ala | Ser | Phe | Thr | Tyr |
| 590 |  |  |  |  | 595 |  |  |  |  | 600 |  |  |  |  | 605 |

1826

|  |  |  |  |  |  |  |  |  |  |  |  |  |  |  |  |
|---|---|---|---|---|---|---|---|---|---|---|---|---|---|---|---|
| ACC | CCT | CGT | TCC | CTG | CCC | GAG | GAT | GAC | ACG | TCC | ATG | GCC | ATC | CTG | AGC |
| Thr | Pro | Arg | Ser | Leu | Pro | Glu | Asp | Asp | Thr | Ser | Met | Ala | Ile | Leu | Ser |
|  |  |  |  | 610 |  |  |  |  | 615 |  |  |  |  | 620 |  |

1874

|  |  |  |  |  |  |  |  |  |  |  |  |  |  |  |  |
|---|---|---|---|---|---|---|---|---|---|---|---|---|---|---|---|
| ATG | CTG | CAG | GAC | ATG | AAT | TTC | ATC | AAC | AAC | TAC | AAA | ATT | GAC | TGC | CCG |
| Met | Leu | Gln | Asp | Met | Asn | Phe | Ile | Asn | Asn | Tyr | Lys | Ile | Asp | Cys | Pro |
|  |  |  | 625 |  |  |  |  | 630 |  |  |  |  | 635 |  |  |

1922

|  |  |  |  |  |  |  |  |  |  |  |  |  |  |  |  |
|---|---|---|---|---|---|---|---|---|---|---|---|---|---|---|---|
| ACC | CTG | GCC | CGG | TTC | TGT | TTG | ATG | GTG | AAG | AAG | GGC | TAC | CGG | GAT | CCC |
| Thr | Leu | Ala | Arg | Phe | Cys | Leu | Met | Val | Lys | Lys | Gly | Tyr | Arg | Asp | Pro |
|  |  | 640 |  |  |  |  | 645 |  |  |  |  | 650 |  |  |  |

1970

|  |  |  |  |  |  |  |  |  |  |  |  |  |  |  |  |
|---|---|---|---|---|---|---|---|---|---|---|---|---|---|---|---|
| CCC | TAC | CAC | AAC | TGG | ATG | CAC | GCC | TTT | TCT | GTC | TCC | CAC | TTC | TGC | TAC |
| Pro | Tyr | His | Asn | Trp | Met | His | Ala | Phe | Ser | Val | Ser | His | Phe | Cys | Tyr |
|  | 655 |  |  |  |  | 660 |  |  |  |  | 665 |  |  |  |  |

2018

|  |  |  |  |  |  |  |  |  |  |  |  |  |  |  |  |
|---|---|---|---|---|---|---|---|---|---|---|---|---|---|---|---|
| CTG | CTC | TAC | AAG | AAC | CTG | GAG | CTC | ACC | AAC | TAC | CTC | GAG | GAC | ATC | GAG |
| Leu | Leu | Tyr | Lys | Asn | Leu | Glu | Leu | Thr | Asn | Tyr | Leu | Glu | Asp | Ile | Glu |
| 670 |  |  |  |  | 675 |  |  |  |  | 680 |  |  |  |  | 685 |

2066

|  |  |  |  |  |  |  |  |  |  |  |  |  |  |  |  |
|---|---|---|---|---|---|---|---|---|---|---|---|---|---|---|---|
| ATC | TTT | GCC | TTG | TTT | ATT | TCC | TGC | ATG | TGT | CAT | GAC | CTG | GAC | CAC | AGA |
| Ile | Phe | Ala | Leu | Phe | Ile | Ser | Cys | Met | Cys | His | Asp | Leu | Asp | His | Arg |
|  |  |  |  | 690 |  |  |  |  | 695 |  |  |  |  | 700 |  |

2114

|  |  |  |  |  |  |  |  |  |  |  |  |  |  |  |  |
|---|---|---|---|---|---|---|---|---|---|---|---|---|---|---|---|
| GGC | ACA | AAC | AAC | TCT | TTC | CAG | GTG | GCC | TCG | AAA | TCT | GTG | CTG | GCT | GCG |
| Gly | Thr | Asn | Asn | Ser | Phe | Gln | Val | Ala | Ser | Lys | Ser | Val | Leu | Ala | Ala |
|  |  |  | 705 |  |  |  |  | 710 |  |  |  |  | 715 |  |  |

2162

|  |  |  |  |  |  |  |  |  |  |  |  |  |  |  |  |
|---|---|---|---|---|---|---|---|---|---|---|---|---|---|---|---|
| CTC | TAC | AGC | TCT | GAG | GGC | TCC | GTC | ATG | GAG | AGG | CAC | CAC | TTT | GCT | CAG |
| Leu | Tyr | Ser | Ser | Glu | Gly | Ser | Val | Met | Glu | Arg | His | His | Phe | Ala | Gln |
|  |  | 720 |  |  |  |  | 725 |  |  |  |  | 730 |  |  |  |

2210

|  |  |  |  |  |  |  |  |  |  |  |  |  |  |  |  |
|---|---|---|---|---|---|---|---|---|---|---|---|---|---|---|---|
| GCC | ATC | GCC | ATC | CTC | AAC | ACC | CAC | GGC | TGC | AAC | ATC | TTT | GAT | CAT | TTC |
| Ala | Ile | Ala | Ile | Leu | Asn | Thr | His | Gly | Cys | Asn | Ile | Phe | Asp | His | Phe |
| 735 |  |  |  |  | 740 |  |  |  |  | 745 |  |  |  |  |  |

2258

|  |  |  |  |  |  |  |  |  |  |  |  |  |  |  |  |
|---|---|---|---|---|---|---|---|---|---|---|---|---|---|---|---|
| TCC | CGG | AAG | GAC | TAT | CAG | CGC | ATG | CTG | GAT | CTG | ATG | CGG | GAC | ATC | ATC |
| Ser | Arg | Lys | Asp | Tyr | Gln | Arg | Met | Leu | Asp | Leu | Met | Arg | Asp | Ile | Ile |
| 750 |  |  |  |  | 755 |  |  |  |  | 760 |  |  |  |  | 765 |

2306

|  |  |  |  |  |  |  |  |  |  |  |  |  |  |  |  |
|---|---|---|---|---|---|---|---|---|---|---|---|---|---|---|---|
| TTG | GCC | ACA | GAC | CTG | GCC | CAC | CAT | CTC | CGC | ATC | TTC | AAG | GAC | CTC | CAG |
| Leu | Ala | Thr | Asp | Leu | Ala | His | His | Leu | Arg | Ile | Phe | Lys | Asp | Leu | Gln |
|  |  |  |  | 770 |  |  |  |  | 775 |  |  |  |  | 780 |  |

2354

|  |  |  |  |  |  |  |  |  |  |  |  |  |  |  |  |
|---|---|---|---|---|---|---|---|---|---|---|---|---|---|---|---|
| AAG | ATG | GCT | GAG | GTG | GGC | TAC | GAC | CGA | AAC | AAC | AAG | CAG | CAC | CAC | AGA |
| Lys | Met | Ala | Glu | Val | Gly | Tyr | Asp | Arg | Asn | Asn | Lys | Gln | His | His | Arg |
|  |  |  | 785 |  |  |  |  | 790 |  |  |  |  | 795 |  |  |

2402

|  |  |  |  |  |  |  |  |  |  |  |  |  |  |  |  |
|---|---|---|---|---|---|---|---|---|---|---|---|---|---|---|---|
| CTT | CTC | CTC | TGC | CTC | CTC | ATG | ACC | TCC | TGT | GAC | CTC | TCT | GAC | CAG | ACC |
| Leu | Leu | Leu | Cys | Leu | Leu | Met | Thr | Ser | Cys | Asp | Leu | Ser | Asp | Gln | Thr |
|  |  | 800 |  |  |  |  | 805 |  |  |  |  | 810 |  |  |  |

2450

|  |  |  |  |  |  |  |  |  |  |  |  |  |  |  |  |
|---|---|---|---|---|---|---|---|---|---|---|---|---|---|---|---|
| AAG | GGC | TGG | AAG | ACT | ACG | AGA | AAG | ATC | GCG | GAG | CTG | ATC | TAC | AAA | GAA |
| Lys | Gly | Trp | Lys | Thr | Thr | Arg | Lys | Ile | Ala | Glu | Leu | Ile | Tyr | Lys | Glu |
|  | 815 |  |  |  |  | 820 |  |  |  |  | 825 |  |  |  |  |

2498

|  |  |  |  |  |  |  |  |  |  |  |  |  |  |  |  |
|---|---|---|---|---|---|---|---|---|---|---|---|---|---|---|---|
| TTC | TTC | TCC | CAG | GGA | GAC | CTG | GAG | AAG | GCC | ATG | GGC | AAC | AGG | CCG | ATG |
| Phe | Phe | Ser | Gln | Gly | Asp | Leu | Glu | Lys | Ala | Met | Gly | Asn | Arg | Pro | Met |
| 830 |  |  |  |  | 835 |  |  |  |  | 840 |  |  |  |  | 845 |

2546

|  |  |  |  |  |  |  |  |  |  |  |  |  |  |  |  |
|---|---|---|---|---|---|---|---|---|---|---|---|---|---|---|---|
| GAG | ATG | ATG | GAC | CGG | GAG | AAG | GCC | TAT | ATC | CCT | GAG | CTG | CAA | ATC | AGC |
| Glu | Met | Met | Asp | Arg | Glu | Lys | Ala | Tyr | Ile | Pro | Glu | Leu | Gln | Ile | Ser |

2594

|   |   |   |   |   |   |   |   |   |   |   |   |   |   |   |   |      |
|---|---|---|---|---|---|---|---|---|---|---|---|---|---|---|---|------|
|   |   |   | 850 |   |   |   |   | 855 |   |   |   |   | 860 |   |   |      |
| TTC | ATG | GAG | CAC | ATT | GCA | ATG | CCC | ATC | TAC | AAG | CTG | TTG | CAG | GAC | CTG | 2642 |
| Phe | Met | Glu | His | Ile | Ala | Met | Pro | Ile | Tyr | Lys | Leu | Leu | Gln | Asp | Leu |      |
|   |   |   | 865 |   |   |   |   | 870 |   |   |   |   | 875 |   |   |      |
| TTC | CCC | AAA | GCG | GCA | GAG | CTG | TAC | GAG | CGC | GTG | GCC | TCC | AAC | CGT | GAG | 2690 |
| Phe | Pro | Lys | Ala | Ala | Glu | Leu | Tyr | Glu | Arg | Val | Ala | Ser | Asn | Arg | Glu |      |
|   |   | 880 |   |   |   |   | 885 |   |   |   |   | 890 |   |   |   |      |
| CAC | TGG | ACC | AAG | GTG | TCC | CAC | AAG | TTC | ACC | ATC | CGC | GGC | CTC | CCA | AGT | 2738 |
| His | Trp | Thr | Lys | Val | Ser | His | Lys | Phe | Thr | Ile | Arg | Gly | Leu | Pro | Ser |      |
|   | 895 |   |   |   |   | 900 |   |   |   |   | 905 |   |   |   |   |      |
| AAC | AAC | TCG | CTG | GAC | TTC | CTG | GAT | GAG | GAG | TAC | GAG | GTG | CCT | GAT | CTG | 2786 |
| Asn | Asn | Ser | Leu | Asp | Phe | Leu | Asp | Glu | Glu | Tyr | Glu | Val | Pro | Asp | Leu |      |
| 910 |   |   |   |   | 915 |   |   |   |   | 920 |   |   |   |   | 925 |      |
| GAT | GGC | ACT | AGG | GCC | CCC | ATC | AAT | GGC | TGC | TGC | AGC | CTT | GAT | GCT | GAG | 2834 |
| Asp | Gly | Thr | Arg | Ala | Pro | Ile | Asn | Gly | Cys | Cys | Ser | Leu | Asp | Ala | Glu |      |
|   |   |   |   | 930 |   |   |   |   | 935 |   |   |   |   | 940 |   |      |

| | | |
|---|---|---|
| TGACTCGAGC | GTCATATTAA TGGACGCAAA GCAAGGAAAT TGCGAGCGGG AAATAAGAAA | 2894 |
| CGATAGAAGT | AGGAATCGAT ACCCGGTGCG TGCACATAAC AGTCTTTTAC CAATTAACAG | 2954 |
| GAGAGATTGA | AGTGTCGAGA TACGAAATGA AATTTACTAC GACTACCGTA AAGAAATGCA | 3014 |
| TAAGCTCTGT | TAGAGAAAAA TTGGTAGCCA | 3044 |

( 2 ) INFORMATION FOR SEQ ID NO:45:

( i ) SEQUENCE CHARACTERISTICS:
        ( A ) LENGTH: 941 amino acids
        ( B ) TYPE: amino acid
        ( D ) TOPOLOGY: linear ( i i ) MOLECULE TYPE: protein ( x i ) SEQUENCE DESCRIPTION: SEQ ID NO:45:

| | | | | | | | | | | | | | | |
|---|---|---|---|---|---|---|---|---|---|---|---|---|---|---|
| Met | Gly | Gln | Ala | Cys | Gly | His | Ser | Ile | Leu | Cys | Arg | Ser | Gln | Gln | Tyr |
| 1 |   |   |   | 5 |   |   |   |   | 10 |   |   |   |   | 15 |   |
| Pro | Ala | Ala | Arg | Pro | Ala | Glu | Pro | Arg | Gly | Gln | Gln | Val | Phe | Leu | Lys |
|   |   |   | 20 |   |   |   |   | 25 |   |   |   |   | 30 |   |   |
| Pro | Asp | Glu | Pro | Pro | Pro | Pro | Gln | Pro | Cys | Ala | Asp | Ser | Leu | Gln |
|   |   | 35 |   |   |   |   | 40 |   |   |   |   | 45 |   |   |
| Asp | Ala | Leu | Leu | Ser | Leu | Gly | Ser | Val | Ile | Asp | Ile | Ser | Gly | Leu | Gln |
|   | 50 |   |   |   |   | 55 |   |   |   |   | 60 |   |   |   |   |
| Arg | Ala | Val | Lys | Glu | Ala | Leu | Ser | Ala | Val | Leu | Pro | Arg | Val | Glu | Thr |
| 65 |   |   |   |   | 70 |   |   |   |   | 75 |   |   |   |   | 80 |
| Val | Tyr | Thr | Tyr | Leu | Leu | Asp | Gly | Glu | Ser | Gln | Leu | Val | Cys | Glu | Asp |
|   |   |   |   | 85 |   |   |   |   | 90 |   |   |   |   | 95 |   |
| Pro | Pro | His | Glu | Leu | Pro | Gln | Glu | Gly | Lys | Val | Arg | Glu | Ala | Ile | Ile |
|   |   |   | 100 |   |   |   |   | 105 |   |   |   |   | 110 |   |   |
| Ser | Gln | Lys | Arg | Leu | Gly | Cys | Asn | Gly | Leu | Gly | Phe | Ser | Asp | Leu | Pro |
|   |   | 115 |   |   |   |   | 120 |   |   |   |   | 125 |   |   |   |
| Gly | Lys | Pro | Leu | Ala | Arg | Leu | Val | Ala | Pro | Leu | Ala | Pro | Asp | Thr | Gln |
|   | 130 |   |   |   |   | 135 |   |   |   |   | 140 |   |   |   |   |
| Val | Leu | Val | Met | Pro | Leu | Ala | Asp | Lys | Glu | Ala | Gly | Ala | Val | Ala | Ala |
| 145 |   |   |   |   | 150 |   |   |   |   | 155 |   |   |   |   | 160 |
| Val | Ile | Leu | Val | His | Cys | Gly | Gln | Leu | Ser | Asp | Asn | Glu | Glu | Trp | Ser |
|   |   |   |   | 165 |   |   |   |   | 170 |   |   |   |   | 175 |   |
| Leu | Gln | Ala | Val | Glu | Lys | His | Thr | Leu | Val | Ala | Leu | Arg | Arg | Val | Gln |
|   |   |   | 180 |   |   |   |   | 185 |   |   |   |   | 190 |   |   |
| Val | Leu | Gln | Gln | Arg | Gly | Pro | Arg | Glu | Ala | Pro | Arg | Ala | Val | Gln | Asn |
|   |   | 195 |   |   |   |   | 200 |   |   |   |   | 205 |   |   |   |

| | | | | | | | | | | | | | |
|---|---|---|---|---|---|---|---|---|---|---|---|---|---|
| Pro | Pro 210 | Glu | Gly | Thr | Ala | Glu 215 | Asp | Gln | Lys | Gly 220 | Gly | Ala | Ala | Tyr | Thr |
| Asp 225 | Arg | Asp | Arg | Lys | Ile 230 | Leu | Gln | Leu | Cys | Gly 235 | Glu | Leu | Tyr | Asp | Leu 240 |
| Asp | Ala | Ser | Ser | Leu 245 | Gln | Leu | Lys | Val | Leu 250 | Gln | Tyr | Leu | Gln | Gln 255 | Glu |
| Thr | Arg | Ala | Ser | Arg 260 | Cys | Cys | Leu | Leu | Leu 265 | Val | Ser | Glu | Asp 270 | Asn | Leu |
| Gln | Leu | Ser 275 | Cys | Lys | Val | Ile | Gly 280 | Asp | Lys | Val | Leu | Gly 285 | Glu | Glu | Val |
| Ser | Phe 290 | Pro | Leu | Thr | Gly | Cys 295 | Leu | Gly | Gln | Val | Val 300 | Glu | Asp | Lys | Lys |
| Ser 305 | Ile | Gln | Leu | Lys | Asp 310 | Leu | Thr | Ser | Glu | Asp 315 | Val | Gln | Gln | Leu | Gln 320 |
| Ser | Met | Leu | Gly | Cys 325 | Glu | Leu | Gln | Ala | Met 330 | Leu | Cys | Val | Pro | Val 335 | Ile |
| Ser | Arg | Ala | Thr 340 | Asp | Gln | Val | Val | Ala 345 | Leu | Ala | Cys | Ala | Phe 350 | Asn | Lys |
| Leu | Glu | Gly 355 | Asp | Leu | Phe | Thr | Asp 360 | Glu | Asp | Glu | His | Val 365 | Ile | Gln | His |
| Cys | Phe 370 | His | Tyr | Thr | Ser | Thr 375 | Val | Leu | Thr | Ser | Thr 380 | Leu | Ala | Phe | Gln |
| Lys 385 | Glu | Gln | Lys | Leu | Lys 390 | Cys | Glu | Cys | Gln | Ala 395 | Leu | Leu | Gln | Val | Ala 400 |
| Lys | Asn | Leu | Phe | Thr 405 | His | Leu | Asp | Asp | Val 410 | Ser | Val | Leu | Leu | Gln 415 | Glu |
| Ile | Ile | Thr | Glu 420 | Ala | Arg | Asn | Leu | Ser 425 | Asn | Ala | Glu | Ile | Cys 430 | Ser | Val |
| Phe | Leu | Leu 435 | Asp | Gln | Asn | Glu | Leu 440 | Val | Ala | Lys | Val | Phe 445 | Asp | Gly | Gly |
| Val | Val 450 | Asp | Asp | Glu | Ser | Tyr 455 | Glu | Ile | Arg | Ile | Pro 460 | Ala | Asp | Gln | Gly |
| Ile 465 | Ala | Gly | His | Val | Ala 470 | Thr | Thr | Gly | Gln | Ile 475 | Leu | Asn | Ile | Pro | Asp 480 |
| Ala | Tyr | Ala | His | Pro 485 | Leu | Phe | Tyr | Arg | Gly 490 | Val | Asp | Asp | Ser | Thr 495 | Gly |
| Phe | Arg | Thr | Arg 500 | Asn | Ile | Leu | Cys | Phe 505 | Pro | Ile | Lys | Asn | Glu 510 | Asn | Gln |
| Glu | Val | Ile 515 | Gly | Val | Ala | Glu | Leu 520 | Val | Asn | Lys | Ile | Asn 525 | Gly | Pro | Trp |
| Phe | Ser 530 | Lys | Phe | Asp | Glu | Asp 535 | Leu | Ala | Thr | Ala | Phe 540 | Ser | Ile | Tyr | Cys |
| Gly 545 | Ile | Ser | Ile | Ala | His 550 | Ser | Leu | Leu | Tyr | Lys 555 | Lys | Val | Asn | Glu | Ala 560 |
| Gln | Tyr | Arg | Ser | His 565 | Leu | Ala | Asn | Glu | Met 570 | Met | Tyr | His | Met 575 | Lys |
| Val | Ser | Asp | Asp 580 | Glu | Tyr | Thr | Lys | Leu 585 | Leu | His | Asp | Gly | Ile 590 | Gln | Pro |
| Val | Ala | Ala 595 | Ile | Asp | Ser | Asn | Phe 600 | Ala | Ser | Phe | Thr | Tyr 605 | Thr | Pro | Arg |
| Ser | Leu 610 | Pro | Glu | Asp | Asp | Thr 615 | Ser | Met | Ala | Ile | Leu 620 | Ser | Met | Leu | Gln |
| Asp | Met | Asn | Phe | Ile | Asn | Asn | Tyr | Lys | Ile | Asp | Cys | Pro | Thr | Leu | Ala |

|  | 625 |  |  |  | 630 |  |  |  | 635 |  |  |  | 640 |
|---|---|---|---|---|---|---|---|---|---|---|---|---|---|
| Arg | Phe | Cys | Leu | Met 645 | Val | Lys | Lys | Gly | Tyr 650 | Arg | Asp | Pro | Pro | Tyr 655 | His |
| Asn | Trp | Met | His 660 | Ala | Phe | Ser | Val | Ser 665 | His | Phe | Cys | Tyr | Leu 670 | Leu | Tyr |
| Lys | Asn | Leu 675 | Glu | Leu | Thr | Asn | Tyr 680 | Leu | Glu | Asp | Ile | Glu 685 | Ile | Phe | Ala |
| Leu | Phe 690 | Ile | Ser | Cys | Met | Cys 695 | His | Asp | Leu | Asp | His 700 | Arg | Gly | Thr | Asn |
| Asn 705 | Ser | Phe | Gln | Val | Ala 710 | Ser | Lys | Ser | Val | Leu 715 | Ala | Ala | Leu | Tyr | Ser 720 |
| Ser | Glu | Gly | Ser | Val 725 | Met | Glu | Arg | His | His 730 | Phe | Ala | Gln | Ala | Ile 735 | Ala |
| Ile | Leu | Asn | Thr 740 | His | Gly | Cys | Asn | Ile 745 | Phe | Asp | His | Phe | Ser 750 | Arg | Lys |
| Asp | Tyr | Gln 755 | Arg | Met | Leu | Asp | Leu 760 | Met | Arg | Asp | Ile | Ile 765 | Leu | Ala | Thr |
| Asp | Leu 770 | Ala | His | His | Leu | Arg 775 | Ile | Phe | Lys | Asp | Leu 780 | Gln | Lys | Met | Ala |
| Glu 785 | Val | Gly | Tyr | Asp | Arg 790 | Asn | Asn | Lys | Gln | His 795 | His | Arg | Leu | Leu | Leu 800 |
| Cys | Leu | Leu | Met | Thr 805 | Ser | Cys | Asp | Leu | Ser 810 | Asp | Gln | Thr | Lys | Gly 815 | Trp |
| Lys | Thr | Thr | Arg 820 | Lys | Ile | Ala | Glu | Leu 825 | Ile | Tyr | Lys | Glu | Phe 830 | Phe | Ser |
| Gln | Gly | Asp 835 | Leu | Glu | Lys | Ala | Met 840 | Gly | Asn | Arg | Pro | Met 845 | Glu | Met | Met |
| Asp | Arg 850 | Glu | Lys | Ala | Tyr | Ile 855 | Pro | Glu | Leu | Gln | Ile 860 | Ser | Phe | Met | Glu |
| His 865 | Ile | Ala | Met | Pro | Ile 870 | Tyr | Lys | Leu | Leu | Gln 875 | Asp | Leu | Phe | Pro | Lys 880 |
| Ala | Ala | Glu | Leu | Tyr 885 | Glu | Arg | Val | Ala | Ser 890 | Asn | Arg | Glu | His | Trp 895 | Thr |
| Lys | Val | Ser | His 900 | Lys | Phe | Thr | Ile | Arg 905 | Gly | Leu | Pro | Ser | Asn 910 | Asn | Ser |
| Leu | Asp | Phe 915 | Leu | Asp | Glu | Glu | Tyr 920 | Glu | Val | Pro | Asp | Leu 925 | Asp | Gly | Thr |
| Arg | Ala 930 | Pro | Ile | Asn | Gly | Cys 935 | Cys | Ser | Leu | Asp | Ala 940 | Glu |

( 2 ) INFORMATION FOR SEQ ID NO:46:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( i v ) ANTI-SENSE: YES ( x i ) SEQUENCE DESCRIPTION: SEQ ID NO:46:

TCRTTNGTNG TNCCYTTCAT RTT    23

( 2 ) INFORMATION FOR SEQ ID NO:47:

( i ) SEQUENCE CHARACTERISTICS:

5,602,019

103                                                                                          104
-continued ( A ) LENGTH: 8 amino acids
   ( B ) TYPE: amino acid
   ( D ) TOPOLOGY: linear ( i i ) MOLECULE TYPE: peptide ( x i ) SEQUENCE DESCRIPTION: SEQ ID NO:47:

Asn Met Lys Gly Thr Thr Asn Asp
 1               5

( 2 ) INFORMATION FOR SEQ ID NO:48:

( i ) SEQUENCE CHARACTERISTICS:
       ( A ) LENGTH: 1625 base pairs
       ( B ) TYPE: nucleic acid
       ( C ) STRANDEDNESS: single
       ( D ) TOPOLOGY: linear ( i i ) MOLECULE TYPE: cDNA ( i x ) FEATURE:
       ( A ) NAME/KEY: CDS
       ( B ) LOCATION: 12..1616

( x i ) SEQUENCE DESCRIPTION: SEQ ID NO:48:

| GAATTCTGAT C | ATG | GGG | TCT | AGT | GCC | ACA | GAG | ATT | GAA | GAA | TTG | GAA | AAC | 50 |
|              | Met | Gly | Ser | Ser | Ala | Thr | Glu | Ile | Glu | Glu | Leu | Glu | Asn | |
|              | 1   |     |     |     | 5   |     |     |     |     | 10  |     |     |     | |

| ACC | ACT | TTT | AAG | TAT | CTT | ACA | GGA | GAA | CAG | ACT | GAA | AAA | ATG | TGG | CAG | 98 |
| Thr | Thr | Phe | Lys | Tyr | Leu | Thr | Gly | Glu | Gln | Thr | Glu | Lys | Met | Trp | Gln | |
|     | 15  |     |     |     |     | 20  |     |     |     |     | 25  |     |     |     |     | |

| CGC | CTG | AAA | GGA | ATA | CTA | AGA | TGC | TTG | GTG | AAG | CAG | CTG | GAA | AGA | GGT | 146 |
| Arg | Leu | Lys | Gly | Ile | Leu | Arg | Cys | Leu | Val | Lys | Gln | Leu | Glu | Arg | Gly | |
| 30  |     |     |     |     | 35  |     |     |     |     | 40  |     |     |     |     | 45  | |

| GAT | GTT | AAC | GTC | GTC | GAC | TTA | AAG | AAG | AAT | ATT | GAA | TAT | GCG | GCA | TCT | 194 |
| Asp | Val | Asn | Val | Val | Asp | Leu | Lys | Lys | Asn | Ile | Glu | Tyr | Ala | Ala | Ser | |
|     |     |     |     | 50  |     |     |     |     | 55  |     |     |     |     | 60  |     | |

| GTG | CTG | GAA | GCA | GTT | TAT | ATC | GAT | GAA | ACA | AGA | AGA | CTT | CTG | GAT | ACT | 242 |
| Val | Leu | Glu | Ala | Val | Tyr | Ile | Asp | Glu | Thr | Arg | Arg | Leu | Leu | Asp | Thr | |
|     |     |     | 65  |     |     |     |     | 70  |     |     |     |     | 75  |     |     | |

| GAA | GAT | GAG | CTC | AGT | GAC | ATT | CAG | ACT | GAC | TCA | GTC | CCA | TCT | GAA | GTC | 290 |
| Glu | Asp | Glu | Leu | Ser | Asp | Ile | Gln | Thr | Asp | Ser | Val | Pro | Ser | Glu | Val | |
|     |     | 80  |     |     |     |     | 85  |     |     |     |     | 90  |     |     |     | |

| CGG | GAC | TGG | TTG | GCT | TCT | ACC | TTT | ACA | CGG | AAA | ATG | GGG | ATG | ACA | AAA | 338 |
| Arg | Asp | Trp | Leu | Ala | Ser | Thr | Phe | Thr | Arg | Lys | Met | Gly | Met | Thr | Lys | |
|     | 95  |     |     |     |     | 100 |     |     |     |     | 105 |     |     |     |     | |

| AAG | AAA | CCT | GAG | GAA | AAA | CCA | AAA | TTT | CGG | AGC | ATT | GTG | CAT | GCT | GTT | 386 |
| Lys | Lys | Pro | Glu | Glu | Lys | Pro | Lys | Phe | Arg | Ser | Ile | Val | His | Ala | Val | |
| 110 |     |     |     |     | 115 |     |     |     |     | 120 |     |     |     |     | 125 | |

| CAA | GCT | GGA | ATT | TTT | GTG | GAA | AGA | ATG | TAC | CGA | AAA | ACA | TAT | CAT | ATG | 434 |
| Gln | Ala | Gly | Ile | Phe | Val | Glu | Arg | Met | Tyr | Arg | Lys | Thr | Tyr | His | Met | |
|     |     |     |     | 130 |     |     |     |     | 135 |     |     |     |     | 140 |     | |

| GTT | GGT | TTG | GCA | TAT | CCA | GCA | GCT | GTC | ATC | GTA | ACA | TTA | AAG | GAT | GTT | 482 |
| Val | Gly | Leu | Ala | Tyr | Pro | Ala | Ala | Val | Ile | Val | Thr | Leu | Lys | Asp | Val | |
|     |     |     |     | 145 |     |     |     | 150 |     |     |     |     | 155 |     |     | |

| GAT | AAA | TGG | TCT | TTC | GAT | GTA | TTT | GCC | CTA | AAT | GAA | GCA | AGT | GGA | GAG | 530 |
| Asp | Lys | Trp | Ser | Phe | Asp | Val | Phe | Ala | Leu | Asn | Glu | Ala | Ser | Gly | Glu | |
|     |     | 160 |     |     |     |     | 165 |     |     |     |     | 170 |     |     |     | |

| CAT | AGT | CTG | AAG | TTT | ATG | ATT | TAT | GAA | CTG | TTT | ACC | AGA | TAT | GAT | CTT | 578 |
| His | Ser | Leu | Lys | Phe | Met | Ile | Tyr | Glu | Leu | Phe | Thr | Arg | Tyr | Asp | Leu | |
|     | 175 |     |     |     |     | 180 |     |     |     |     | 185 |     |     |     |     | |

| ATC | AAC | CGT | TTC | AAG | ATT | CCT | GTT | TCT | TGC | CTA | ATC | ACC | TTT | GCA | GAA | 626 |
| Ile | Asn | Arg | Phe | Lys | Ile | Pro | Val | Ser | Cys | Leu | Ile | Thr | Phe | Ala | Glu | |
| 190 |     |     |     |     | 195 |     |     |     |     | 200 |     |     |     |     | 205 | |

| | | | | | | | | | | | | | | | | |
|---|---|---|---|---|---|---|---|---|---|---|---|---|---|---|---|---|
| GCT | TTA | GAA | GTT | GGT | TAC | AGC | AAG | TAC | AAA | AAT | CCA | TAT | CAC | AAT | TTG | 674 |
| Ala | Leu | Glu | Val | Gly 210 | Tyr | Ser | Lys | Tyr 215 | Lys | Asn | Pro | Tyr | His | Asn 220 | Leu | |
| ATT | CAT | GCA | GCT | GAT | GTC | ACT | CAA | ACT | GTG | CAT | TAC | ATA | ATG | CTT | CAT | 722 |
| Ile | His | Ala | Ala 225 | Asp | Val | Thr | Gln | Thr 230 | Val | His | Tyr | Ile | Met 235 | Leu | His | |
| ACA | GGT | ATC | ATG | CAC | TGG | CTC | ACT | GAA | CTG | GAA | ATT | TTA | GCA | ATG | GTC | 770 |
| Thr | Gly | Ile 240 | Met | His | Trp | Leu | Thr 245 | Glu | Leu | Glu | Ile | Leu 250 | Ala | Met | Val | |
| TTT | GCT | GCT | GCC | ATT | CAT | GAT | TAT | GAG | CAT | ACA | GGG | ACA | ACA | AAC | AAC | 818 |
| Phe | Ala | Ala 255 | Ala | Ile | His | Asp | Tyr 260 | Glu | His | Thr | Gly | Thr 265 | Thr | Asn | Asn | |
| TTT | CAC | ATT | CAG | ACA | AGG | TCA | GAT | GTT | GCC | ATT | TTG | TAT | AAT | GAT | CGC | 866 |
| Phe 270 | His | Ile | Gln | Thr | Arg 275 | Ser | Asp | Val | Ala | Ile 280 | Leu | Tyr | Asn | Asp | Arg 285 | |
| TCT | GTC | CTT | GAG | AAT | CAC | CAC | GTG | AGT | GCA | GCT | TAT | CGA | CTT | ATG | CAA | 914 |
| Ser | Val | Leu | Glu | Asn 290 | His | His | Val | Ser 295 | Ala | Ala | Tyr | Arg | Leu 300 | Met | Gln | |
| GAA | GAA | GAA | ATG | AAT | ATC | TTG | ATA | AAT | TTA | TCC | AAA | GAT | GAC | TGG | AGG | 962 |
| Glu | Glu | Glu | Met 305 | Asn | Ile | Leu | Ile | Asn 310 | Leu | Ser | Lys | Asp | Asp 315 | Trp | Arg | |
| GAT | CTT | CGG | AAC | CTA | GTG | ATT | GAA | ATG | GTT | TTA | TCT | ACA | GAC | ATG | TCA | 1010 |
| Asp | Leu | Arg 320 | Asn | Leu | Val | Ile | Glu 325 | Met | Val | Leu | Ser | Thr 330 | Asp | Met | Ser | |
| GGT | CAC | TTC | CAG | CAA | ATT | AAA | AAT | ATA | AGA | AAC | AGT | TTG | CAG | CAG | CCT | 1058 |
| Gly | His 335 | Phe | Gln | Gln | Ile | Lys 340 | Asn | Ile | Arg | Asn | Ser 345 | Leu | Gln | Gln | Pro | |
| GAA | GGG | ATT | GAC | AGA | GCC | AAA | ACC | ATG | TCC | CTG | ATT | CTC | CAC | GCA | GCA | 1106 |
| Glu 350 | Gly | Ile | Asp | Arg | Ala 355 | Lys | Thr | Met | Ser | Leu 360 | Ile | Leu | His | Ala | Ala 365 | |
| GAC | ATC | AGC | CAC | CCA | GCC | AAA | TCC | TGG | AAG | CTG | CAT | TAT | CGG | TGG | ACC | 1154 |
| Asp | Ile | Ser | His | Pro 370 | Ala | Lys | Ser | Trp | Lys 375 | Leu | His | Tyr | Arg | Trp 380 | Thr | |
| ATG | GCC | CTA | ATG | GAG | GAG | TTT | TTC | CTG | CAG | GGA | GAT | AAA | GAA | GCT | GAA | 1202 |
| Met | Ala | Leu | Met 385 | Glu | Glu | Phe | Phe | Leu 390 | Gln | Gly | Asp | Lys | Glu 395 | Ala | Glu | |
| TTA | GGG | CTT | CCA | TTT | TCC | CCA | CTT | TGT | GAT | CGG | AAG | TCA | ACC | ATG | GTG | 1250 |
| Leu | Gly | Leu 400 | Pro | Phe | Ser | Pro | Leu 405 | Cys | Asp | Arg | Lys | Ser 410 | Thr | Met | Val | |
| GCC | CAG | TCA | CAA | ATA | GGT | TTC | ATC | GAT | TTC | ATA | GTA | GAG | CCA | ACA | TTT | 1298 |
| Ala | Gln | Ser 415 | Gln | Ile | Gly | Phe | Ile 420 | Asp | Phe | Ile | Val | Glu 425 | Pro | Thr | Phe | |
| TCT | CTT | CTG | ACA | GAC | TCA | ACA | GAG | AAA | ATT | GTT | ATT | CCT | CTT | ATA | GAG | 1346 |
| Ser | Leu | Leu | Thr 430 | Asp | Ser | Thr | Glu | Lys 435 | Ile | Val | Ile | Pro | Leu 440 | Ile | Glu 445 | |
| GAA | GCC | TCA | AAA | GCC | GAA | ACT | TCT | TCC | TAT | GTG | GCA | AGC | AGC | TCA | ACC | 1394 |
| Glu | Ala | Ser | Lys | Ala 450 | Glu | Thr | Ser | Ser | Tyr 455 | Val | Ala | Ser | Ser | Ser 460 | Thr | |
| ACC | ATT | GTG | GGG | TTA | CAC | ATT | GCT | GAT | GCA | CTA | AGA | CGA | TCA | AAT | ACA | 1442 |
| Thr | Ile | Val | Gly | Leu 465 | His | Ile | Ala | Asp | Ala 470 | Leu | Arg | Arg | Ser | Asn 475 | Thr | |
| AAA | GGC | TCC | ATG | AGT | GAT | GGG | TCC | TAT | TCC | CCA | GAC | TAC | TCC | CTT | GCA | 1490 |
| Lys | Gly | Ser | Met 480 | Ser | Asp | Gly | Ser | Tyr 485 | Ser | Pro | Asp | Tyr | Ser 490 | Leu | Ala | |
| GCA | GTG | GAC | CTG | AAG | AGT | TTC | AAG | AAC | AAC | CTG | GTG | GAC | ATC | ATT | CAG | 1538 |
| Ala | Val | Asp 495 | Leu | Lys | Ser | Phe | Lys 500 | Asn | Asn | Leu | Val | Asp 505 | Ile | Ile | Gln | |
| CAG | AAC | AAA | GAG | AGG | TGG | AAA | GAG | TTA | GCT | GCA | CAA | GAA | GCA | AGA | ACC | 1586 |
| Gln | Asn | Lys | Glu | Arg 515 | Trp | Lys | Glu | Leu | Ala 520 | Ala | Gln | Glu | Ala | Arg 525 | Thr | |

```
AGT  TCA  CAG  AAG  TGT  GAG  TTT  ATT  CAT  CAG  TAACTCGAG                                    1625
Ser  Ser  Gln  Lys  Cys  Glu  Phe  Ile  His  Gln
               530                         535
```

( 2 ) INFORMATION FOR SEQ ID NO:49:

( i ) SEQUENCE CHARACTERISTICS:
        ( A ) LENGTH: 535 amino acids
        ( B ) TYPE: amino acid
        ( D ) TOPOLOGY: linear ( i i ) MOLECULE TYPE: protein ( x i ) SEQUENCE DESCRIPTION: SEQ ID NO:49:

```
Met  Gly  Ser  Ser  Ala  Thr  Glu  Ile  Glu  Glu  Leu  Glu  Asn  Thr  Thr  Phe
 1                  5                       10                      15
Lys  Tyr  Leu  Thr  Gly  Glu  Gln  Thr  Glu  Lys  Met  Trp  Gln  Arg  Leu  Lys
              20                       25                      30
Gly  Ile  Leu  Arg  Cys  Leu  Val  Lys  Gln  Leu  Glu  Arg  Gly  Asp  Val  Asn
              35                  40                      45
Val  Val  Asp  Leu  Lys  Lys  Asn  Ile  Glu  Tyr  Ala  Ala  Ser  Val  Leu  Glu
     50                       55                      60
Ala  Val  Tyr  Ile  Asp  Glu  Thr  Arg  Arg  Leu  Leu  Asp  Thr  Glu  Asp  Glu
 65                      70                      75                      80
Leu  Ser  Asp  Ile  Gln  Thr  Asp  Ser  Val  Pro  Ser  Glu  Val  Arg  Asp  Trp
                   85                       90                       95
Leu  Ala  Ser  Thr  Phe  Thr  Arg  Lys  Met  Gly  Met  Thr  Lys  Lys  Lys  Pro
                  100                      105                     110
Glu  Glu  Lys  Pro  Lys  Phe  Arg  Ser  Ile  Val  His  Ala  Val  Gln  Ala  Gly
              115                     120                     125
Ile  Phe  Val  Glu  Arg  Met  Tyr  Arg  Lys  Thr  Tyr  His  Met  Val  Gly  Leu
     130                     135                     140
Ala  Tyr  Pro  Ala  Ala  Val  Ile  Val  Thr  Leu  Lys  Asp  Val  Asp  Lys  Trp
145                      150                     155                     160
Ser  Phe  Asp  Val  Phe  Ala  Leu  Asn  Glu  Ala  Ser  Gly  Glu  His  Ser  Leu
                   165                     170                     175
Lys  Phe  Met  Ile  Tyr  Glu  Leu  Phe  Thr  Arg  Tyr  Asp  Leu  Ile  Asn  Arg
              180                     185                     190
Phe  Lys  Ile  Pro  Val  Ser  Cys  Leu  Ile  Thr  Phe  Ala  Glu  Ala  Leu  Glu
     195                     200                     205
Val  Gly  Tyr  Ser  Lys  Tyr  Lys  Asn  Pro  Tyr  His  Asn  Leu  Ile  His  Ala
     210                     215                     220
Ala  Asp  Val  Thr  Gln  Thr  Val  His  Tyr  Ile  Met  Leu  His  Thr  Gly  Ile
225                      230                     235                     240
Met  His  Trp  Leu  Thr  Glu  Leu  Glu  Ile  Leu  Ala  Met  Val  Phe  Ala  Ala
                   245                     250                     255
Ala  Ile  His  Asp  Tyr  Glu  His  Thr  Gly  Thr  Thr  Asn  Asn  Phe  His  Ile
                   260                     265                     270
Gln  Thr  Arg  Ser  Asp  Val  Ala  Ile  Leu  Tyr  Asn  Asp  Arg  Ser  Val  Leu
              275                     280                     285
Glu  Asn  His  His  Val  Ser  Ala  Ala  Tyr  Arg  Leu  Met  Gln  Glu  Glu  Glu
     290                     295                     300
Met  Asn  Ile  Leu  Ile  Asn  Leu  Ser  Lys  Asp  Asp  Trp  Arg  Asp  Leu  Arg
305                      310                     315                     320
Asn  Leu  Val  Ile  Glu  Met  Val  Leu  Ser  Thr  Asp  Met  Ser  Gly  His  Phe
                   325                     330                     335
Gln  Gln  Ile  Lys  Asn  Ile  Arg  Asn  Ser  Leu  Gln  Gln  Pro  Glu  Gly  Ile
```

5,602,019

109                                                                                                                                                 110
-continued

|     |     |     | 340 |     |     |     |     | 345 |     |     |     |     | 350 |     |     |
|-----|-----|-----|-----|-----|-----|-----|-----|-----|-----|-----|-----|-----|-----|-----|-----|

Asp Arg Ala Lys Thr Met Ser Leu Ile Leu His Ala Ala Asp Ile Ser
            355                 360                 365

His Pro Ala Lys Ser Trp Lys Leu His Tyr Arg Trp Thr Met Ala Leu
        370                 375                 380

Met Glu Glu Phe Phe Leu Gln Gly Asp Lys Glu Ala Glu Leu Gly Leu
385                     390                 395                     400

Pro Phe Ser Pro Leu Cys Asp Arg Lys Ser Thr Met Val Ala Gln Ser
                405                 410                 415

Gln Ile Gly Phe Ile Asp Phe Ile Val Glu Pro Thr Phe Ser Leu Leu
            420                 425                 430

Thr Asp Ser Thr Glu Lys Ile Val Ile Pro Leu Ile Glu Glu Ala Ser
            435                 440                 445

Lys Ala Glu Thr Ser Ser Tyr Val Ala Ser Ser Ser Thr Thr Ile Val
    450                 455                 460

Gly Leu His Ile Ala Asp Ala Leu Arg Arg Ser Asn Thr Lys Gly Ser
465                 470                 475                     480

Met Ser Asp Gly Ser Tyr Ser Pro Asp Tyr Ser Leu Ala Ala Val Asp
                485                 490                 495

Leu Lys Ser Phe Lys Asn Asn Leu Val Asp Ile Ile Gln Gln Asn Lys
            500                 505                 510

Glu Arg Trp Lys Glu Leu Ala Ala Gln Glu Ala Arg Thr Ser Ser Gln
        515                 520                 525

Lys Cys Glu Phe Ile His Gln
    530                 535

( 2 ) INFORMATION FOR SEQ ID NO:50:

( i ) SEQUENCE CHARACTERISTICS:
            ( A ) LENGTH: 2693 base pairs
            ( B ) TYPE: nucleic acid
            ( C ) STRANDEDNESS: single
            ( D ) TOPOLOGY: linear ( i i ) MOLECULE TYPE: cDNA ( i x ) FEATURE:
            ( A ) NAME/KEY: CDS
            ( B ) LOCATION: 176..2077

( x i ) SEQUENCE DESCRIPTION: SEQ ID NO:50:

GTCGCTTCAA TATTTCAAAA TGGATCCGGT TCTGTGGCGG GTGCGAGAGT GAGGCTGTGG        60

GGGACCTCCA GGCCGAACCT CCGCGAAGCC TCGGCCTTCT GCGTGCCCTG GCCCCGGGAG      120

GATAAGGATT TCCCTTCCCT CCTACTTGCG CGCGGAGCCG AGCTCTTGTT GAGCT ATG       178
                                                               Met
                                                                 1

GAG TCG CCA ACC AAG GAG ATT GAA GAA TTT GAG AGC AAC TCT CTG AAA       226
Glu Ser Pro Thr Lys Glu Ile Glu Glu Phe Glu Ser Asn Ser Leu Lys
              5                  10                  15

TAC CTG CAA CCG GAA CAG ATC GAG AAA ATC TGG CTT CGG CTC CGC GGG       274
Tyr Leu Gln Pro Glu Gln Ile Glu Lys Ile Trp Leu Arg Leu Arg Gly
         20                  25                  30

CTG AGG AAA TAT AAG AAA ACG TCC CAG AGA TTA CGG TCT TTG GTC AAA       322
Leu Arg Lys Tyr Lys Lys Thr Ser Gln Arg Leu Arg Ser Leu Val Lys
     35                  40                  45

CAA TTA GAG AGA GGG GAA GCT TCA GTG GTA GAT CTT AAG AAG AAT TTG       370
Gln Leu Glu Arg Gly Glu Ala Ser Val Val Asp Leu Lys Lys Asn Leu
 50                  55                  60                  65

GAA TAT GCA GCC ACA GTG CTT GAA TCT GTG TAT ATT GAT GAA ACA AGG       418

|  |  |  |  |  |  |  |  |  |  |  |  |  |  |  |  |
|---|---|---|---|---|---|---|---|---|---|---|---|---|---|---|---|
| Glu | Tyr | Ala | Ala | Thr 70 | Val | Leu | Glu | Ser | Val 75 | Tyr | Ile | Asp | Glu | Thr 80 | Arg |

| AGA | CTC | CTG | GAT | ACA | GAG | GAT | GAG | CTC | AGT | GAC | ATT | CAG | TCA | GAT | GCT | 466 |
|---|---|---|---|---|---|---|---|---|---|---|---|---|---|---|---|---|
| Arg | Leu | Leu | Asp 85 | Thr | Glu | Asp | Glu | Leu 90 | Ser | Asp | Ile | Gln | Ser 95 | Asp | Ala | |

| GTG | CCT | TCT | GAG | GTC | CGA | GAC | TGG | CTG | GCC | TCC | ACC | TTC | ACG | CGG | CAG | 514 |
|---|---|---|---|---|---|---|---|---|---|---|---|---|---|---|---|---|
| Val | Pro | Ser 100 | Glu | Val | Arg | Asp | Trp 105 | Leu | Ala | Ser | Thr | Phe 110 | Thr | Arg | Gln | |

| ATG | GGG | ATG | ATG | CTC | AGG | AGG | AGC | GAC | GAG | AAG | CCC | CGG | TTC | AAG | AGC | 562 |
|---|---|---|---|---|---|---|---|---|---|---|---|---|---|---|---|---|
| Met | Gly 115 | Met | Met | Leu | Arg | Arg 120 | Ser | Asp | Glu | Lys | Pro 125 | Arg | Phe | Lys | Ser | |

| ATC | GTT | CAC | GCA | GTG | CAG | GCT | GGG | ATA | TTT | GTG | GAG | AGA | ATG | TAT | AGA | 610 |
|---|---|---|---|---|---|---|---|---|---|---|---|---|---|---|---|---|
| Ile 130 | Val | His | Ala | Val | Gln 135 | Ala | Gly | Ile | Phe | Val 140 | Glu | Arg | Met | Tyr | Arg 145 | |

| CGG | ACA | TCA | AAC | ATG | GTT | GGA | CTG | AGC | TAT | CCA | CCA | GCT | GTT | ATT | GAG | 658 |
|---|---|---|---|---|---|---|---|---|---|---|---|---|---|---|---|---|
| Arg | Thr | Ser | Asn | Met 150 | Val | Gly | Leu | Ser | Tyr 155 | Pro | Pro | Ala | Val | Ile 160 | Glu | |

| GCA | TTA | AAG | GAT | GTG | GAC | AAG | TGG | TCC | TTT | GAC | GTC | TTT | TCC | CTC | AAT | 706 |
|---|---|---|---|---|---|---|---|---|---|---|---|---|---|---|---|---|
| Ala | Leu | Lys | Asp 165 | Val | Asp | Lys | Trp | Ser 170 | Phe | Asp | Val | Phe | Ser 175 | Leu | Asn | |

| GAG | GCC | AGT | GGG | GAT | CAT | GCA | CTG | AAA | TTT | ATT | TTC | TAT | GAA | CTA | CTC | 754 |
|---|---|---|---|---|---|---|---|---|---|---|---|---|---|---|---|---|
| Glu | Ala | Ser 180 | Gly | Asp | His | Ala | Leu 185 | Lys | Phe | Ile | Phe | Tyr 190 | Glu | Leu | Leu | |

| ACA | CGT | TAT | GAT | CTG | ATC | AGC | CGT | TTC | AAG | ATC | CCC | ATT | TCT | GCA | CTT | 802 |
|---|---|---|---|---|---|---|---|---|---|---|---|---|---|---|---|---|
| Thr | Arg 195 | Tyr | Asp | Leu | Ile | Ser 200 | Arg | Phe | Lys | Ile | Pro 205 | Ile | Ser | Ala | Leu | |

| GTC | TCA | TTT | GTG | GAG | GCC | CTG | GAA | GTG | GGA | TAC | AGC | AAG | CAC | AAA | AAT | 850 |
|---|---|---|---|---|---|---|---|---|---|---|---|---|---|---|---|---|
| Val 210 | Ser | Phe | Val | Glu | Ala 215 | Leu | Glu | Val | Gly | Tyr 220 | Ser | Lys | His | Lys | Asn 225 | |

| CCT | TAC | CAT | AAC | TTA | ATG | CAC | GCT | GCC | GAT | GTT | ACA | CAG | ACA | GTG | CAT | 898 |
|---|---|---|---|---|---|---|---|---|---|---|---|---|---|---|---|---|
| Pro | Tyr | His | Asn | Leu 230 | Met | His | Ala | Ala | Asp 235 | Val | Thr | Gln | Thr | Val 240 | His | |

| TAC | CTC | CTC | TAT | AAG | ACA | GGA | GTG | GCG | AAC | TGG | CTG | ACG | GAG | CTG | GAG | 946 |
|---|---|---|---|---|---|---|---|---|---|---|---|---|---|---|---|---|
| Tyr | Leu | Leu | Tyr 245 | Lys | Thr | Gly | Val | Ala 250 | Asn | Trp | Leu | Thr | Glu 255 | Leu | Glu | |

| ATC | TTT | GCT | ATA | ATC | TTC | TCA | GCT | GCC | ATC | CAT | GAC | TAC | GAG | CAT | ACC | 994 |
|---|---|---|---|---|---|---|---|---|---|---|---|---|---|---|---|---|
| Ile | Phe | Ala 260 | Ile | Ile | Phe | Ser | Ala 265 | Ala | Ile | His | Asp | Tyr 270 | Glu | His | Thr | |

| GGA | ACC | ACC | AAC | AAT | TTC | CAC | ATT | CAG | ACT | CGG | TCT | GAT | CCA | GCT | ATT | 1042 |
|---|---|---|---|---|---|---|---|---|---|---|---|---|---|---|---|---|
| Gly | Thr 275 | Thr | Asn | Asn | Phe | His 280 | Ile | Gln | Thr | Arg | Ser 285 | Asp | Pro | Ala | Ile | |

| CTG | TAT | AAT | GAC | AGA | TCT | GTA | CTG | GAG | AAT | CAC | CAT | TTA | AGT | GCA | GCT | 1090 |
|---|---|---|---|---|---|---|---|---|---|---|---|---|---|---|---|---|
| Leu 290 | Tyr | Asn | Asp | Arg | Ser 295 | Val | Leu | Glu | Asn | His 300 | His | Leu | Ser | Ala | Ala 305 | |

| TAT | CGC | CTT | CTG | CAA | GAT | GAC | GAG | GAA | ATG | AAT | ATT | TTG | ATT | AAC | CTC | 1138 |
|---|---|---|---|---|---|---|---|---|---|---|---|---|---|---|---|---|
| Tyr | Arg | Leu | Leu | Gln 310 | Asp | Asp | Glu | Glu | Met 315 | Asn | Ile | Leu | Ile | Asn 320 | Leu | |

| TCA | AAG | GAT | GAC | TGG | AGG | GAG | TTT | CGA | ACC | TTG | GTA | ATT | GAA | ATG | GTG | 1186 |
|---|---|---|---|---|---|---|---|---|---|---|---|---|---|---|---|---|
| Ser | Lys | Asp | Asp 325 | Trp | Arg | Glu | Phe | Arg 330 | Thr | Leu | Val | Ile | Glu 335 | Met | Val | |

| ATG | GCC | ACA | GAT | ATG | TCT | TGT | CAC | TTC | CAA | CAA | ATC | AAA | GCA | ATG | AAG | 1234 |
|---|---|---|---|---|---|---|---|---|---|---|---|---|---|---|---|---|
| Met | Ala | Thr 340 | Asp | Met | Ser | Cys | His 345 | Phe | Gln | Gln | Ile | Lys 350 | Ala | Met | Lys | |

| ACT | GCT | CTG | CAG | CAG | CCA | GAA | GCC | ATT | GAA | AAG | CCA | AAA | GCC | TTA | TCC | 1282 |
|---|---|---|---|---|---|---|---|---|---|---|---|---|---|---|---|---|
| Thr | Ala | Leu 355 | Gln | Gln | Pro | Glu | Ala 360 | Ile | Glu | Lys | Pro | Lys 365 | Ala | Leu | Ser | |

| CTT | ATG | CTG | CAT | ACA | GCA | GAT | ATT | AGC | CAT | CCA | GCA | AAA | GCA | TGG | GAC | 1330 |
|---|---|---|---|---|---|---|---|---|---|---|---|---|---|---|---|---|
| Leu 370 | Met | Leu | His | Thr | Ala 375 | Asp | Ile | Ser | His | Pro 380 | Ala | Lys | Ala | Trp | Asp 385 | |

| CTC | CAT | CAT | CGC | TGG | ACA | ATG | TCA | CTC | CTG | GAG | GAG | TTC | TTC | AGA | CAG | 1378 |

```
Leu His His Arg Trp Thr Met Ser Leu Leu Glu Glu Phe Phe Arg Gln
            390             395                         400

GGT GAC AGA GAA GCA GAG CTG GGG CTG CCT TTT TCT CCT CTG TGT GAC    1426
Gly Asp Arg Glu Ala Glu Leu Gly Leu Pro Phe Ser Pro Leu Cys Asp
            405                         410             415

CGA AAG TCC ACT ATG GTT GCT CAG TCA CAA GTA GGT TTC ATT GAT TTC    1474
Arg Lys Ser Thr Met Val Ala Gln Ser Gln Val Gly Phe Ile Asp Phe
            420                 425                 430

ATC GTG GAA CCC ACC TTC ACT GTG CTT ACG GAC ATG ACC GAG AAG ATT    1522
Ile Val Glu Pro Thr Phe Thr Val Leu Thr Asp Met Thr Glu Lys Ile
    435                         440                 445

GTG AGT CCA TTA ATC GAT GAA ACC TCT CAA ACT GGT GGG ACA GGA CAG    1570
Val Ser Pro Leu Ile Asp Glu Thr Ser Gln Thr Gly Gly Thr Gly Gln
450                     455                 460                 465

AGG CGT TCG AGT TTG AAT AGC ATC AGC TCG TCA GAT GCC AAG CGA TCA    1618
Arg Arg Ser Ser Leu Asn Ser Ile Ser Ser Ser Asp Ala Lys Arg Ser
                470                 475                 480

GGT GTC AAG ACC TCT GGT TCA GAG GGA AGT GCC CCG ATC AAC AAT TCT    1666
Gly Val Lys Thr Ser Gly Ser Glu Gly Ser Ala Pro Ile Asn Asn Ser
            485                 490                 495

GTC ATC TCC GTT GAC TAT AAG AGC TTT AAA GCT ACT TGG ACG GAA GTG    1714
Val Ile Ser Val Asp Tyr Lys Ser Phe Lys Ala Thr Trp Thr Glu Val
        500                 505                 510

GTG CAC ATC AAT CGG GAG AGA TGG AGG GCC AAG GTA CCC AAA GAG GAG    1762
Val His Ile Asn Arg Glu Arg Trp Arg Ala Lys Val Pro Lys Glu Glu
    515                 520                 525

AAG GCC AAG AAG GAA GCA GAG GAA AAG GCT CGC CTG GCC GCA GAG GAG    1810
Lys Ala Lys Lys Glu Ala Glu Glu Lys Ala Arg Leu Ala Ala Glu Glu
530                 535                 540                 545

CAG CAA AAG GAA ATG GAA GCC AAA AGC CAG GCT GAA GAA GGC GCA TCT    1858
Gln Gln Lys Glu Met Glu Ala Lys Ser Gln Ala Glu Glu Gly Ala Ser
                550                 555                 560

GGC AAA GCT GAG AAA AAG ACG TCT GGA GAA ACT AAG AAT CAA GTC AAT    1906
Gly Lys Ala Glu Lys Lys Thr Ser Gly Glu Thr Lys Asn Gln Val Asn
            565                 570                 575

GGA ACA CGG GCA AAC AAA AGT GAC AAC CCT CGT GGG AAA AAT TCC AAA    1954
Gly Thr Arg Ala Asn Lys Ser Asp Asn Pro Arg Gly Lys Asn Ser Lys
            580                 585                 590

GCC GAG AAG TCA TCA GGA GAA CAG CAA CAG AAT GGT GAC TTC AAA GAT    2002
Ala Glu Lys Ser Ser Gly Glu Gln Gln Gln Asn Gly Asp Phe Lys Asp
    595                 600                 605

GGT AAA AAT AAG ACA GAC AAG AAG GAT CAC TCT AAC ATC GGA AAT GAT    2050
Gly Lys Asn Lys Thr Asp Lys Lys Asp His Ser Asn Ile Gly Asn Asp
610                 615                 620                 625

TCA AAG AAA ACA GAT GAT TCA CAA GAG TAAAAAGAC CTCATAGACA           2097
Ser Lys Lys Thr Asp Asp Ser Gln Glu
                630

ATAAAGAGG CTGCCAGTGT CTTGCATCAT TCTAGCTGAG CTTCTTCATT CTCCTTCTTC    2157

TCCTTCTTCC ACAAAGACCC ATATCTGGAG AAGGTGTACA ACTTTCAAAC ACAAGCCCCC    2217

CACCCCCTGA CCCTTGGCCT TCCCTCACAC CATCTCCTTC CAGGGGATGA ATCTTTGGGG    2277

GTTGGTTTGA GGTCTTAGAA CTCTGGGGGA TATTCCCCTG AGCAAAACAA ACAACGTGAG    2337

ATTTTTACTC AAACAGAAAC AAAACATGAA GGGGCATCCT CAAAATCCTT TGCTAATGAC    2397

CTGGCTTTCA AGGCATCTGT CTGGCCTGAT GAGAATGGAC ATCCTGGATA TGCTGGGAGA    2457

GGCCTGAAAA AAGCCACACA CACAGTAATT GCCATTTTAT GACTGTCAAT GCCGTTACTT    2517

TAAATGTTGT CATTTTTGCA CTGGCTACTG ATGATACAGC CATGCTGACA TTCATCACCG    2577

CAAAGATGAT GATTCCAGTC TCTGGTTCCT TTCCTGAGTC AGGAACATTT GTTTTCTCCA    2637
```

ATTTCCTTTC AGACTTAAAA TTGTTCTTAT GCTTTTTTTC CCACTTCTGT AATACA    2693

( 2 ) INFORMATION FOR SEQ ID NO:51:

( i ) SEQUENCE CHARACTERISTICS:
        ( A ) LENGTH: 634 amino acids
        ( B ) TYPE: amino acid
        ( D ) TOPOLOGY: linear ( i i ) MOLECULE TYPE: protein ( x i ) SEQUENCE DESCRIPTION: SEQ ID NO:51:

| | | | | | | | | | | | | | | | |
|---|---|---|---|---|---|---|---|---|---|---|---|---|---|---|---|
| Met | Glu | Ser | Pro | Thr | Lys | Glu | Ile | Glu | Glu | Phe | Glu | Ser | Asn | Ser | Leu |
| 1 | | | | 5 | | | | | 10 | | | | | 15 | |
| Lys | Tyr | Leu | Gln | Pro | Glu | Gln | Ile | Glu | Lys | Ile | Trp | Leu | Arg | Leu | Arg |
| | | | 20 | | | | | 25 | | | | | 30 | | |
| Gly | Leu | Arg | Lys | Tyr | Lys | Lys | Thr | Ser | Gln | Arg | Leu | Arg | Ser | Leu | Val |
| | | | 35 | | | | 40 | | | | | 45 | | | |
| Lys | Gln | Leu | Glu | Arg | Gly | Glu | Ala | Ser | Val | Val | Asp | Leu | Lys | Lys | Asn |
| | | 50 | | | | | 55 | | | | | 60 | | | |
| Leu | Glu | Tyr | Ala | Ala | Thr | Val | Leu | Glu | Ser | Val | Tyr | Ile | Asp | Glu | Thr |
| 65 | | | | | 70 | | | | | 75 | | | | | 80 |
| Arg | Arg | Leu | Leu | Asp | Thr | Glu | Asp | Glu | Leu | Ser | Asp | Ile | Gln | Ser | Asp |
| | | | | 85 | | | | | 90 | | | | | 95 | |
| Ala | Val | Pro | Ser | Glu | Val | Arg | Asp | Trp | Leu | Ala | Ser | Thr | Phe | Thr | Arg |
| | | | 100 | | | | | 105 | | | | | 110 | | |
| Gln | Met | Gly | Met | Met | Leu | Arg | Arg | Ser | Asp | Glu | Lys | Pro | Arg | Phe | Lys |
| | | 115 | | | | | 120 | | | | | 125 | | | |
| Ser | Ile | Val | His | Ala | Val | Gln | Ala | Gly | Ile | Phe | Val | Glu | Arg | Met | Tyr |
| | 130 | | | | | 135 | | | | | 140 | | | | |
| Arg | Arg | Thr | Ser | Asn | Met | Val | Gly | Leu | Ser | Tyr | Pro | Pro | Ala | Val | Ile |
| 145 | | | | | 150 | | | | | 155 | | | | | 160 |
| Glu | Ala | Leu | Lys | Asp | Val | Asp | Lys | Trp | Ser | Phe | Asp | Val | Phe | Ser | Leu |
| | | | | 165 | | | | | 170 | | | | | 175 | |
| Asn | Glu | Ala | Ser | Gly | Asp | His | Ala | Leu | Lys | Phe | Ile | Phe | Tyr | Glu | Leu |
| | | | 180 | | | | | 185 | | | | | 190 | | |
| Leu | Thr | Arg | Tyr | Asp | Leu | Ile | Ser | Arg | Phe | Lys | Ile | Pro | Ile | Ser | Ala |
| | | 195 | | | | | 200 | | | | | 205 | | | |
| Leu | Val | Ser | Phe | Val | Glu | Ala | Leu | Glu | Val | Gly | Tyr | Ser | Lys | His | Lys |
| | 210 | | | | | 215 | | | | | 220 | | | | |
| Asn | Pro | Tyr | His | Asn | Leu | Met | His | Ala | Ala | Asp | Val | Thr | Gln | Thr | Val |
| 225 | | | | | 230 | | | | | 235 | | | | | 240 |
| His | Tyr | Leu | Leu | Tyr | Lys | Thr | Gly | Val | Ala | Asn | Trp | Leu | Thr | Glu | Leu |
| | | | | 245 | | | | | 250 | | | | | 255 | |
| Glu | Ile | Phe | Ala | Ile | Ile | Phe | Ser | Ala | Ala | Ile | His | Asp | Tyr | Glu | His |
| | | | 260 | | | | | 265 | | | | | 270 | | |
| Thr | Gly | Thr | Thr | Asn | Asn | Phe | His | Ile | Gln | Thr | Arg | Ser | Asp | Pro | Ala |
| | | 275 | | | | | 280 | | | | | 285 | | | |
| Ile | Leu | Tyr | Asn | Asp | Arg | Ser | Val | Leu | Glu | Asn | His | His | Leu | Ser | Ala |
| | 290 | | | | | 295 | | | | | 300 | | | | |
| Ala | Tyr | Arg | Leu | Leu | Gln | Asp | Asp | Glu | Glu | Met | Asn | Ile | Leu | Ile | Asn |
| 305 | | | | | 310 | | | | | 315 | | | | | 320 |
| Leu | Ser | Lys | Asp | Asp | Trp | Arg | Glu | Phe | Arg | Thr | Leu | Val | Ile | Glu | Met |
| | | | | 325 | | | | | 330 | | | | | 335 | |
| Val | Met | Ala | Thr | Asp | Met | Ser | Cys | His | Phe | Gln | Gln | Ile | Lys | Ala | Met |
| | | | 340 | | | | | 345 | | | | | 350 | | |

| | | | | | | | | | | | | | | | |
|---|---|---|---|---|---|---|---|---|---|---|---|---|---|---|---|
| Lys | Thr | Ala | Leu | Gln | Gln | Pro | Glu | Ala | Ile | Glu | Lys | Pro | Lys | Ala | Leu |
| | | 355 | | | | 360 | | | | | 365 | | | | |
| Ser | Leu | Met | Leu | His | Thr | Ala | Asp | Ile | Ser | His | Pro | Ala | Lys | Ala | Trp |
| | 370 | | | | | 375 | | | | | | 380 | | | |
| Asp | Leu | His | His | Arg | Trp | Thr | Met | Ser | Leu | Leu | Glu | Glu | Phe | Phe | Arg |
| 385 | | | | | 390 | | | | | 395 | | | | | 400 |
| Gln | Gly | Asp | Arg | Glu | Ala | Glu | Leu | Gly | Leu | Pro | Phe | Ser | Pro | Leu | Cys |
| | | | | 405 | | | | | 410 | | | | | 415 | |
| Asp | Arg | Lys | Ser | Thr | Met | Val | Ala | Gln | Ser | Gln | Val | Gly | Phe | Ile | Asp |
| | | | 420 | | | | | 425 | | | | | 430 | | |
| Phe | Ile | Val | Glu | Pro | Thr | Phe | Thr | Val | Leu | Thr | Asp | Met | Thr | Glu | Lys |
| | | 435 | | | | | 440 | | | | | 445 | | | |
| Ile | Val | Ser | Pro | Leu | Ile | Asp | Glu | Thr | Ser | Gln | Thr | Gly | Gly | Thr | Gly |
| | 450 | | | | | 455 | | | | | 460 | | | | |
| Gln | Arg | Arg | Ser | Ser | Leu | Asn | Ser | Ile | Ser | Ser | Ser | Asp | Ala | Lys | Arg |
| 465 | | | | | 470 | | | | | 475 | | | | | 480 |
| Ser | Gly | Val | Lys | Thr | Ser | Gly | Ser | Glu | Gly | Ser | Ala | Pro | Ile | Asn | Asn |
| | | | | 485 | | | | | 490 | | | | | 495 | |
| Ser | Val | Ile | Ser | Val | Asp | Tyr | Lys | Ser | Phe | Lys | Ala | Thr | Trp | Thr | Glu |
| | | | | 500 | | | | 505 | | | | | 510 | | |
| Val | Val | His | Ile | Asn | Arg | Glu | Arg | Trp | Arg | Ala | Lys | Val | Pro | Lys | Glu |
| | | 515 | | | | | 520 | | | | | 525 | | | |
| Glu | Lys | Ala | Lys | Lys | Glu | Ala | Glu | Glu | Lys | Ala | Arg | Leu | Ala | Ala | Glu |
| | 530 | | | | | 535 | | | | | 540 | | | | |
| Glu | Gln | Gln | Lys | Glu | Met | Glu | Ala | Lys | Ser | Gln | Ala | Glu | Glu | Gly | Ala |
| 545 | | | | | 550 | | | | | 555 | | | | | 560 |
| Ser | Gly | Lys | Ala | Glu | Lys | Lys | Thr | Ser | Gly | Glu | Thr | Lys | Asn | Gln | Val |
| | | | | 565 | | | | | 570 | | | | | 575 | |
| Asn | Gly | Thr | Arg | Ala | Asn | Lys | Ser | Asp | Asn | Pro | Arg | Gly | Lys | Asn | Ser |
| | | | 580 | | | | | 585 | | | | | 590 | | |
| Lys | Ala | Glu | Lys | Ser | Ser | Gly | Glu | Gln | Gln | Gln | Asn | Gly | Asp | Phe | Lys |
| | | 595 | | | | | 600 | | | | | 605 | | | |
| Asp | Gly | Lys | Asn | Lys | Thr | Asp | Lys | Lys | Asp | His | Ser | Asn | Ile | Gly | Asn |
| | 610 | | | | | 615 | | | | | 620 | | | | |
| Asp | Ser | Lys | Lys | Thr | Asp | Asp | Ser | Gln | Glu | | | | | | |
| 625 | | | | | 630 | | | | | | | | | | |

( 2 ) INFORMATION FOR SEQ ID NO:52:

( i ) SEQUENCE CHARACTERISTICS:
  ( A ) LENGTH: 2077 base pairs
  ( B ) TYPE: nucleic acid
  ( C ) STRANDEDNESS: single
  ( D ) TOPOLOGY: linear ( i i ) MOLECULE TYPE: cDNA ( i x ) FEATURE:
  ( A ) NAME/KEY: CDS
  ( B ) LOCATION: 2..1693

( x i ) SEQUENCE DESCRIPTION: SEQ ID NO:52:

```
A   CGG  ACA  TCA  AAC  ATG  GTT  GGA  CTG  AGC  TAT  CCA  CCA  GCT  GTT  ATT        46
    Arg  Thr  Ser  Asn  Met  Val  Gly  Leu  Ser  Tyr  Pro  Pro  Ala  Val  Ile
     1              5                        10                       15

GAG  GCA  TTA  AAG  GAT  GTG  GAC  AAG  TGG  TCC  TTT  GAC  GTC  TTT  TCC  CTC         94
Glu  Ala  Leu  Lys  Asp  Val  Asp  Lys  Trp  Ser  Phe  Asp  Val  Phe  Ser  Leu
              20                       25                       30
```

| | | | | | | | | | | | | | | | | |
|---|---|---|---|---|---|---|---|---|---|---|---|---|---|---|---|---|
| AAT | GAG | GCC | AGT | GGG | GAT | CAT | GCA | CTG | AAA | TTT | ATT | TTC | TAT | GAA | CTA | 142 |
| Asn | Glu | Ala | Ser 35 | Gly | Asp | His | Ala | Leu 40 | Lys | Phe | Ile | Phe | Tyr 45 | Glu | Leu | |
| CTC | ACA | CGT | TAT | GAT | CTG | ATC | AGC | CGT | TTC | AAG | ATC | CCC | ATT | TCT | GCA | 190 |
| Leu | Thr | Arg 50 | Tyr | Asp | Leu | Ile | Ser 55 | Arg | Phe | Lys | Ile | Pro 60 | Ile | Ser | Ala | |
| CTT | GTC | TCA | TTT | GTG | GAG | GCC | CTG | GAA | GTG | GGA | TAC | AGC | AAG | CAC | AAA | 238 |
| Leu | Val 65 | Ser | Phe | Val | Glu 70 | Ala | Leu | Glu | Val | Gly 75 | Tyr | Ser | Lys | His | Lys | |
| AAT | CCT | TAC | CAT | AAC | TTA | ATG | CAC | GCT | GCC | GAT | GTT | ACA | CAG | ACA | GTG | 286 |
| Asn 80 | Pro | Tyr | His | Asn | Leu 85 | Met | His | Ala | Ala | Asp 90 | Val | Thr | Gln | Thr | Val 95 | |
| CAT | TAC | CTC | CTC | TAT | AAG | ACA | GGA | GTG | GCG | AAC | TGG | CTG | ACG | GAG | CTG | 334 |
| His | Tyr | Leu | Leu | Tyr 100 | Lys | Thr | Gly | Val | Ala 105 | Asn | Trp | Leu | Thr | Glu 110 | Leu | |
| GAG | ATC | TTT | GCT | ATA | ATC | TTC | TCA | GCT | GCC | ATC | CAT | GAC | TAC | GAG | CAT | 382 |
| Glu | Ile | Phe | Ala 115 | Ile | Ile | Phe | Ser | Ala 120 | Ala | Ile | His | Asp | Tyr 125 | Glu | His | |
| ACC | GGA | ACC | ACC | AAC | AAT | TTC | CAC | ATT | CAG | ACT | CGG | TCT | GAT | CCA | GCT | 430 |
| Thr | Gly | Thr 130 | Thr | Asn | Asn | Phe | His 135 | Ile | Gln | Thr | Arg | Ser 140 | Asp | Pro | Ala | |
| ATT | CTG | TAT | AAT | GAC | AGA | TCT | GTA | CTG | GAG | AAT | CAC | CAT | TTA | AGT | GCA | 478 |
| Ile | Leu | Tyr 145 | Asn | Asp | Arg | Ser | Val 150 | Leu | Glu | Asn | His | His 155 | Leu | Ser | Ala | |
| GCT | TAT | CGC | CTT | CTG | CAA | GAT | GAC | GAG | GAA | ATG | AAT | ATT | TTG | ATT | AAC | 526 |
| Ala 160 | Tyr | Arg | Leu | Leu | Gln 165 | Asp | Asp | Glu | Glu | Met 170 | Asn | Ile | Leu | Ile | Asn 175 | |
| CTC | TCA | AAG | GAT | GAC | TGG | AGG | GAG | TTT | CGA | ACC | TTG | GTA | ATT | GAA | ATG | 574 |
| Leu | Ser | Lys | Asp | Asp 180 | Trp | Arg | Glu | Phe | Arg 185 | Thr | Leu | Val | Ile | Glu 190 | Met | |
| GTG | ATG | GCC | ACA | GAT | ATG | TCT | TGT | CAC | TTC | CAA | CAA | ATC | AAA | GCA | ATG | 622 |
| Val | Met | Ala | Thr 195 | Asp | Met | Ser | Cys | His 200 | Phe | Gln | Gln | Ile | Lys 205 | Ala | Met | |
| AAG | ACT | GCT | CTG | CAG | CAG | CCA | GAA | GCC | ATT | GAA | AAG | CCA | AAA | GCC | TTA | 670 |
| Lys | Thr | Ala | Leu 210 | Gln | Gln | Pro | Glu | Ala 215 | Ile | Glu | Lys | Pro | Lys 220 | Ala | Leu | |
| TCC | CTT | ATG | CTG | CAT | ACA | GCA | GAT | ATT | AGC | CAT | CCA | GCA | AAA | GCA | TGG | 718 |
| Ser | Leu | Met 225 | Leu | His | Thr | Ala | Asp 230 | Ile | Ser | His | Pro | Ala 235 | Lys | Ala | Trp | |
| GAC | CTC | CAT | CAT | CGC | TGG | ACA | ATG | TCA | CTC | CTG | GAG | GAG | TTC | TTC | AGA | 766 |
| Asp 240 | Leu | His | His | Arg | Trp 245 | Thr | Met | Ser | Leu | Leu 250 | Glu | Glu | Phe | Phe | Arg 255 | |
| CAG | GGT | GAC | AGA | GAA | GCA | GAG | CTG | GGG | CTG | CCT | TTT | TCT | CCT | CTG | TGT | 814 |
| Gln | Gly | Asp | Arg | Glu 260 | Ala | Glu | Leu | Gly | Leu 265 | Pro | Phe | Ser | Pro | Leu 270 | Cys | |
| GAC | CGA | AAG | TCC | ACT | ATG | GTT | GCT | CAG | TCA | CAA | GTA | GGT | TTC | ATT | GAT | 862 |
| Asp | Arg | Lys | Ser 275 | Thr | Met | Val | Ala | Gln 280 | Ser | Gln | Val | Gly | Phe 285 | Ile | Asp | |
| TTC | ATC | GTG | GAA | CCC | ACC | TTC | ACT | GTG | CTT | ACG | GAC | ATG | ACC | GAG | AAG | 910 |
| Phe | Ile | Val | Glu 290 | Pro | Thr | Phe | Thr | Val 295 | Leu | Thr | Asp | Met | Thr 300 | Glu | Lys | |
| ATT | GTG | AGT | CCA | TTA | ATC | GAT | GAA | ACC | TCT | CAA | ACT | GGT | GGG | ACA | GGA | 958 |
| Ile | Val | Ser 305 | Pro | Leu | Ile | Asp | Glu 310 | Thr | Ser | Gln | Thr | Gly 315 | Gly | Thr | Gly | |
| CAG | AGG | CGT | TCG | AGT | TTG | AAT | AGC | ATC | AGC | TCG | TCA | GAT | GCC | AAG | CGA | 1006 |
| Gln | Arg | Arg | Ser 320 | Ser | Leu | Asn | Ser | Ile 325 | Ser | Ser | Ser | Asp | Ala 330 | Lys | Arg 335 | |
| TCA | GGT | GTC | AAG | ACC | TCT | GGT | TCA | GAG | GGA | AGT | GCC | CCG | ATC | AAC | AAT | 1054 |
| Ser | Gly | Val | Lys | Thr 340 | Ser | Gly | Ser | Glu | Gly 345 | Ser | Ala | Pro | Ile | Asn 350 | Asn | |

| | | | | | | | | | | | | | | | |
|---|---|---|---|---|---|---|---|---|---|---|---|---|---|---|---|
| TCT | GTC | ATC | TCC | GTT | GAC | TAT | AAG | AGC | TTT | AAA | GCT | ACT | TGG | ACG | GAA | 1102 |
| Ser | Val | Ile | Ser | Val | Asp | Tyr | Lys | Ser | Phe | Lys | Ala | Thr | Trp | Thr | Glu | |
| | | | 355 | | | | 360 | | | | | | 365 | | | |
| GTG | GTG | CAC | ATC | AAT | CGG | GAG | AGA | TGG | AGG | GCC | AAG | GTA | CCC | AAA | GAG | 1150 |
| Val | Val | His | Ile | Asn | Arg | Glu | Arg | Trp | Arg | Ala | Lys | Val | Pro | Lys | Glu | |
| | | 370 | | | | 375 | | | | | 380 | | | | | |
| GAG | AAG | GCC | AAG | AAG | GAA | GCA | GAG | GAA | AAG | GCT | CGC | CTG | GCC | GCA | GAG | 1198 |
| Glu | Lys | Ala | Lys | Lys | Glu | Ala | Glu | Glu | Lys | Ala | Arg | Leu | Ala | Ala | Glu | |
| | 385 | | | | | 390 | | | | | 395 | | | | | |
| GAG | CAG | CAA | AAG | GAA | ATG | GAA | GCC | AAA | AGC | CAG | GCT | GAA | GAA | GGC | GCA | 1246 |
| Glu | Gln | Gln | Lys | Glu | Met | Glu | Ala | Lys | Ser | Gln | Ala | Glu | Glu | Gly | Ala | |
| 400 | | | | | 405 | | | | 410 | | | | | 415 | | |
| TCT | GGC | AAA | GCT | GAG | AAA | AAG | ACG | TCT | GGA | GAA | ACT | AAG | AAT | CAA | GTC | 1294 |
| Ser | Gly | Lys | Ala | Glu | Lys | Lys | Thr | Ser | Gly | Glu | Thr | Lys | Asn | Gln | Val | |
| | | | | 420 | | | | | 425 | | | | | 430 | | |
| AAT | GGA | ACA | CGG | GCA | AAC | AAA | AGT | GAC | AAC | CCT | CGT | GGG | AAA | AAT | TCC | 1342 |
| Asn | Gly | Thr | Arg | Ala | Asn | Lys | Ser | Asp | Asn | Pro | Arg | Gly | Lys | Asn | Ser | |
| | | | 435 | | | | | 440 | | | | | 445 | | | |
| AAA | GCT | GAG | AAG | TCA | TCA | GGA | GAA | CAG | CAA | CAG | AAT | GGT | GAC | TTC | AAA | 1390 |
| Lys | Ala | Glu | Lys | Ser | Ser | Gly | Glu | Gln | Gln | Gln | Asn | Gly | Asp | Phe | Lys | |
| | | | 450 | | | | 455 | | | | | 460 | | | | |
| GAT | GGT | AAA | AAT | AAG | ACA | GAC | AAG | AAG | GAT | CAC | TCT | AAC | ATC | GGA | AAT | 1438 |
| Asp | Gly | Lys | Asn | Lys | Thr | Asp | Lys | Lys | Asp | His | Ser | Asn | Ile | Gly | Asn | |
| | 465 | | | | | 470 | | | | | 475 | | | | | |
| GAT | TCA | AAG | AAA | ACA | GAT | GGC | ACA | AAA | CAG | CGT | TCT | CAC | GGC | TCA | CCA | 1486 |
| Asp | Ser | Lys | Lys | Thr | Asp | Gly | Thr | Lys | Gln | Arg | Ser | His | Gly | Ser | Pro | |
| 480 | | | | | 485 | | | | 490 | | | | | | 495 | |
| GCC | CCA | AGC | ACC | AGC | TCC | ACG | TGT | CGC | CTT | ACG | TTG | CCA | GTC | ATC | AAG | 1534 |
| Ala | Pro | Ser | Thr | Ser | Ser | Thr | Cys | Arg | Leu | Thr | Leu | Pro | Val | Ile | Lys | |
| | | | | 500 | | | | 505 | | | | | 510 | | | |
| CCT | CCT | TTG | CGT | CAT | TTT | AAA | CGC | CCT | GCT | TAC | GCA | TCT | AGC | TCC | TAT | 1582 |
| Pro | Pro | Leu | Arg | His | Phe | Lys | Arg | Pro | Ala | Tyr | Ala | Ser | Ser | Ser | Tyr | |
| | | | 515 | | | | | 520 | | | | | 525 | | | |
| GCA | CCT | TCA | GTC | TCA | AAG | AAA | ACT | GAT | GAG | CAT | CCT | GCA | AGG | TAC | AAG | 1630 |
| Ala | Pro | Ser | Val | Ser | Lys | Lys | Thr | Asp | Glu | His | Pro | Ala | Arg | Tyr | Lys | |
| | | 530 | | | | | 535 | | | | | 540 | | | | |
| ATG | CTA | GAT | CAG | AGG | ATC | AAA | ATG | AAA | AAG | ATT | CAG | AAC | ATC | TCA | CAT | 1678 |
| Met | Leu | Asp | Gln | Arg | Ile | Lys | Met | Lys | Lys | Ile | Gln | Asn | Ile | Ser | His | |
| | | | 545 | | | | 550 | | | | | 555 | | | | |
| AAC | TGG | AAC | AGA | AAA | TAGGCCGAGG | | GGAAGAAGAG | | AGGGAGTGAA | | GGAGGGTCTA | | | | | 1733 |
| Asn | Trp | Asn | Arg | Lys | | | | | | | | | | | | |
| 560 | | | | | | | | | | | | | | | | |

| | | | | | |
|---|---|---|---|---|---|
| CCTATCTGCT | TCTCAGCACC | CACTGGCCAC | AGCAGGACAC | ACCTCCAAGA | CCCTTGGAGG | 1793 |
| CTGTTGGAGC | AGGTACTATC | CTGGTTGACT | CCACCAAGGT | GAAATGAAAG | TTGTATGTGA | 1853 |
| TTTTCCTCTT | TGTTGTTCTT | GTATAGACTT | TTCAATTGCT | GTATGTGGGA | TCAGCCCAGA | 1913 |
| CGCCAGCAAC | AAACTAGCAA | GAGGGGTGTT | TTTATGGTAT | AAGTCTCTAA | AAGTCTAAAT | 1973 |
| TGGACCAAAA | TTAAAATGAC | ACAAACTTAA | AAAAAAATAA | AATTCCTCTC | ATTGCCACTT | 2033 |
| TTTTCAATCT | CTAAAAGTTA | CTTGCCCCCA | AAAGAATATT | GGTC | | 2077 |

( 2 ) INFORMATION FOR SEQ ID NO:53:

( i ) SEQUENCE CHARACTERISTICS:
        ( A ) LENGTH: 564 amino acids
        ( B ) TYPE: amino acid
        ( D ) TOPOLOGY: linear ( i i ) MOLECULE TYPE: protein ( x i ) SEQUENCE DESCRIPTION: SEQ ID NO:53:

```
Arg  Thr  Ser  Asn  Met  Val  Gly  Leu  Ser  Tyr  Pro  Pro  Ala  Val  Ile  Glu
 1              5                        10                       15

Ala  Leu  Lys  Asp  Val  Asp  Lys  Trp  Ser  Phe  Asp  Val  Phe  Ser  Leu  Asn
              20                        25                       30

Glu  Ala  Ser  Gly  Asp  His  Ala  Leu  Lys  Phe  Ile  Phe  Tyr  Glu  Leu  Leu
         35                        40                       45

Thr  Arg  Tyr  Asp  Leu  Ile  Ser  Arg  Phe  Lys  Ile  Pro  Ile  Ser  Ala  Leu
    50                        55                       60

Val  Ser  Phe  Val  Glu  Ala  Leu  Glu  Val  Gly  Tyr  Ser  Lys  His  Lys  Asn
65                       70                       75                        80

Pro  Tyr  His  Asn  Leu  Met  His  Ala  Ala  Asp  Val  Thr  Gln  Thr  Val  His
              85                        90                            95

Tyr  Leu  Leu  Tyr  Lys  Thr  Gly  Val  Ala  Asn  Trp  Leu  Thr  Glu  Leu  Glu
              100                       105                      110

Ile  Phe  Ala  Ile  Ile  Phe  Ser  Ala  Ala  Ile  His  Asp  Tyr  Glu  His  Thr
         115                       120                      125

Gly  Thr  Thr  Asn  Asn  Phe  His  Ile  Gln  Thr  Arg  Ser  Asp  Pro  Ala  Ile
    130                       135                      140

Leu  Tyr  Asn  Asp  Arg  Ser  Val  Leu  Glu  Asn  His  His  Leu  Ser  Ala  Ala
145                      150                       155                      160

Tyr  Arg  Leu  Leu  Gln  Asp  Asp  Glu  Glu  Met  Asn  Ile  Leu  Ile  Asn  Leu
              165                       170                      175

Ser  Lys  Asp  Asp  Trp  Arg  Glu  Phe  Arg  Thr  Leu  Val  Ile  Glu  Met  Val
              180                       185                      190

Met  Ala  Thr  Asp  Met  Ser  Cys  His  Phe  Gln  Gln  Ile  Lys  Ala  Met  Lys
         195                       200                      205

Thr  Ala  Leu  Gln  Gln  Pro  Glu  Ala  Ile  Glu  Lys  Pro  Lys  Ala  Leu  Ser
    210                       215                      220

Leu  Met  Leu  His  Thr  Ala  Asp  Ile  Ser  His  Pro  Ala  Lys  Ala  Trp  Asp
225                      230                       235                      240

Leu  His  His  Arg  Trp  Thr  Met  Ser  Leu  Leu  Glu  Glu  Phe  Phe  Arg  Gln
              245                       250                      255

Gly  Asp  Arg  Glu  Ala  Glu  Leu  Gly  Leu  Pro  Phe  Ser  Pro  Leu  Cys  Asp
              260                       265                      270

Arg  Lys  Ser  Thr  Met  Val  Ala  Gln  Ser  Gln  Val  Gly  Phe  Ile  Asp  Phe
         275                       280                      285

Ile  Val  Glu  Pro  Thr  Phe  Thr  Val  Leu  Thr  Asp  Met  Thr  Glu  Lys  Ile
    290                       295                      300

Val  Ser  Pro  Leu  Ile  Asp  Glu  Thr  Ser  Gln  Thr  Gly  Gly  Thr  Gly  Gln
305                      310                       315                      320

Arg  Arg  Ser  Ser  Leu  Asn  Ser  Ile  Ser  Ser  Ser  Asp  Ala  Lys  Arg  Ser
              325                       330                      335

Gly  Val  Lys  Thr  Ser  Gly  Ser  Glu  Gly  Ser  Ala  Pro  Ile  Asn  Asn  Ser
              340                       345                      350

Val  Ile  Ser  Val  Asp  Tyr  Lys  Ser  Phe  Lys  Ala  Thr  Trp  Thr  Glu  Val
         355                       360                      365

Val  His  Ile  Asn  Arg  Glu  Arg  Trp  Arg  Ala  Lys  Val  Pro  Lys  Glu  Glu
    370                       375                      380

Lys  Ala  Lys  Lys  Glu  Ala  Glu  Glu  Lys  Ala  Arg  Leu  Ala  Ala  Glu  Glu
385                      390                       395                      400

Gln  Gln  Lys  Glu  Met  Glu  Ala  Lys  Ser  Gln  Ala  Glu  Glu  Gly  Ala  Ser
              405                       410                      415

Gly  Lys  Ala  Glu  Lys  Lys  Thr  Ser  Gly  Glu  Thr  Lys  Asn  Gln  Val  Asn
              420                       425                      430
```

| | | | | | | | | | | | | | | |
|---|---|---|---|---|---|---|---|---|---|---|---|---|---|---|
| Gly | Thr | Arg<br>435 | Ala | Asn | Lys | Ser | Asp<br>440 | Asn | Pro | Arg | Gly<br>445 | Lys | Asn | Ser | Lys |
| Ala | Glu<br>450 | Lys | Ser | Ser | Gly<br>455 | Glu | Gln | Gln | Gln | Asn<br>460 | Gly | Asp | Phe | Lys | Asp |
| Gly<br>465 | Lys | Asn | Lys | Thr<br>470 | Asp | Lys | Lys | Asp | His<br>475 | Ser | Asn | Ile | Gly | Asn | Asp<br>480 |
| Ser | Lys | Lys | Thr | Asp<br>485 | Gly | Thr | Lys | Gln | Arg<br>490 | Ser | His | Gly | Ser | Pro<br>495 | Ala |
| Pro | Ser | Thr | Ser<br>500 | Ser | Thr | Cys | Arg | Leu<br>505 | Thr | Leu | Pro | Val | Ile<br>510 | Lys | Pro |
| Pro | Leu | Arg<br>515 | His | Phe | Lys | Arg | Pro<br>520 | Ala | Tyr | Ala | Ser | Ser<br>525 | Ser | Tyr | Ala |
| Pro | Ser<br>530 | Val | Ser | Lys | Lys | Thr<br>535 | Asp | Glu | His | Pro | Ala<br>540 | Arg | Tyr | Lys | Met |
| Leu<br>545 | Asp | Gln | Arg | Ile | Lys<br>550 | Met | Lys | Lys | Ile | Gln<br>555 | Asn | Ile | Ser | His | Asn<br>560 |
| Trp | Asn | Arg | Lys | | | | | | | | | | | | |

( 2 ) INFORMATION FOR SEQ ID NO:54:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:54:

TACGAAGCTT TGATGGGGTC TACTGCTAC      29

( 2 ) INFORMATION FOR SEQ ID NO:55:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:55:

TACGAAGCTT TGATGGTTGG CTTGGCATAT C      31

( 2 ) INFORMATION FOR SEQ ID NO:56:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:56:

ATTACCCCTC ATAAAG      16

( 2 ) INFORMATION FOR SEQ ID NO:57:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear (i i) MOLECULE TYPE: DNA (x i) SEQUENCE DESCRIPTION: SEQ ID NO:57:

TACGAAGCTT TGATGCGCCG ACAGCCTGC    29

(2) INFORMATION FOR SEQ ID NO:58:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:58:

GGTCTCCTGT TGCAGATATT G    21

DNA ENCODING MAMMALIAN PHOSPHODIESTERASES

This is a divisional of U.S. patent application Ser. No. 07/872,644, filed Apr. 20, 1992, U.S. Pat. No. 5,389,527, which in turn is a continuation-in-part of U.S. patent application Ser. No. 07/688,356 filed Apr. 19, 1991, now abandoned.

BACKGROUND OF THE INVENTION

The present invention relates to novel purified and isolated nucleotide sequences encoding mammalian $Ca^{2+}$/calmodulin stimulated phosphodiesterases (CaM-PDEs) and cyclic-GMP-stimulated phosphodiesterases (cGS-PDEs). Also provided are the corresponding recombinant expression products of said nucleotide sequences, immunological reagents specifically reactive therewith, and procedures for identifying compounds which modulate the enzymatic activity of such expression products.

Cyclic nucleotides are known to mediate a wide variety of cellular responses to biological stimuli. The cyclic nucleotide phosphodiesterases (PDEs) catalyze the hydrolysis of 3', 5' cyclic nucleotides, such as cyclic adenosine monophosphate (cAMP) and cyclic guanosine monophosphate (cGMP), to their corresponding 5'-nucleotide monophosphates and are consequently important in the control of cellular concentration of cyclic nucleotides. The PDEs in turn are regulated by transmembrane signals or second messenger ligands such as calcium ion ($Ca^{2+}$) or cGMP. The PDEs thus have a central role in regulating the flow of information from extracellular hormones, neurotransmitters, or other signals that use the cyclic nucleotides as messengers.

PDEs are a large and complex group of enzymes. They are widely distributed throughout the cells and tissues of most eukaryotic organisms, but are usually present only in trace amounts. At least five different families of PDEs have been described based on characteristics such as substrate specificity, kinetic properties, cellular regulatory control, size, and in some instances, modulation by selective inhibitors. [Beavo, *Adv. in Second Mess. and Prot. Phosph. Res.* 22:1–38 (1988)]. The five families include:

| |
|---|
| I $Ca^{2+}$/calmodulin-stimulated |
| II cGMP-stimulated |
| III cGMP-inhibited |
| IV cAMP-specific |
| V cGMP-specific |

Within each family there are multiple forms of closely related PDEs. See Beavo, "Multiple Phosphodiesterase Isozymes Background, Nomenclature and Implications", pp. 3–15; Wang et al., "Calmodulin-Stimulated Cyclic Nucleotide Phosphodiesterases", pp. 19–59; and Manganiello et al., "Cyclic GMP-Stimulated Cyclic Nucleotide Phosphodiesterases" pp. 62–85; all in *Cyclic Nucleotide Phosphodiesterases: Structure, Regulation and Drug Action,* Beavo, J. and Housley, M. D., Eds.; John Wiley & Sons, New York (1990).

The $Ca^{2+}$/calmodulin dependent PDEs (CaM-PDEs) are characterized by their responsiveness to intracellular calcium, which leads to a decreased intracellular concentration of cAMP and/or cGMP. A distinctive feature of cGMP'-stimulated phosphodiesterases (cGS-PDEs) is their capacity to be stimulated by cGMP in effecting cAMP hydrolysis.

In vitro studies have shown increased PDE activity in response to $Ca^{2+}$/calmodulin in nearly every mammalian tissue studied, as well as in Drosophila, Dictyostelium, and trypanosomes. The level of CaM-PDE in tissues and cellular and subcellular compartments varies widely. Most cells contain at least a small amount of CaM-PDE activity, with the highest tissue levels being found in the brain, particularly in the synaptic areas. Greenberg et al., *Neuropharmacol.*, 17:737–745 (1978) and Kincaid et al., *PNAS (USA)*, 84:1118–1122 (1987). A decrease in cAMP in astrocytoma cells in response to muscarinic stimulation may be due to calcium dependent increases in CaM-PDE activity. Tanner et al., *Mol. Pharmacol.*, 29:455–460 (1986). Also, CaM-PDE may be an important regulator of cAMP in thyroid tissue. Erneux et al., *Mol. Cell. Endocrinol.*, 43:123–134(1985).

Early studies suggested that there are distinct tissue-specific isozymes of CaM-PDEs. Several members of the CaM-PDE family have now been described, including a 59 kDa isozyme isolated from bovine heart, and 61 and 63 kDa isozymes isolated from bovine brain. LaPorte et al., *Biochemistry*, 18:2820–2825 (1979); Hansen et al., *Proc. Natl. Acad. Sci. USA*, 79:2788–2792 (1982); and Sharma et al., *J. Biol. Chem.*, 261:14160–14166 (1986). Possible counterparts to the bovine 59 and 61 kDa isozymes have also been isolated from rat tissues, Hansen et al., *J. Biol. Chem.*, 261:14636–14645 (1986), suggesting that these two isozymes may be expressed in other mammalian species.

In addition to molecular weight criteria, other evidence supports both similarities and differences among the CaM-PDE family of isozymes. For example, the 59 kDa heart isozyme and the 61 kDa brain isozyme CaM-PDEs differ in mobility on SDS-PAGE and elution position on DEAE chromatography, and the 59 kDa isozyme has at least a 10–20 fold higher affinity for calmodulin. Oncomodulin, a fetal/onco calcium binding protein present in very high concentrations in the placenta and transformed cells, also binds to the 59 kDa enzyme with a higher affinity than to the 61 kDa enzyme. However, both the 61 kDa brain and the 59 kDa heart isozymes are recognized by a single monoclonal antibody. This antibody binds to the $Ca^{2+}$/CaM-PDE complex with 100-fold higher affinity than to PDE alone. Hansen et al., 1986, supra. The 59 and 61 kDA isozymes have nearly identical substrate specificities and kinetic constants. Krinks et al., *Adv. Cyc. Nucleotide Prot. Phosphorylation Res.*, 16:31–47 (1984) have suggested, based on peptide mapping experiments, that the heart 59 kDa protein could be a proteolytic form of the brain 61 kDa isozyme.

The 63 kDa bovine brain isozyme differs substantially from the 59 and 61 kDa isozymes. The 63 kDa enzyme is not recognized by the monoclonal antibody which binds to the 59 and 61 kDa enzymes. Hansen et al., 1986, supra. The 63 kDa protein is not phosphorylated in vitro by cAMP-dependent protein kinase, whereas the 61 kDa protein is phosphorylated. Further, only the 63 kDa protein is phosphorylated in vitro by CaM-kinase II. Sharma et al., *Proc. Natl. Acad. Sci. (USA)*, 82:2603–2607 (1985); and Hashimoto et al., *J. Biol. Chem.*, 264:10884–10887 (1989). The 61 and 63 kDa CaM-PDE isozymes from bovine brain do appear, however, to have similar CaM-binding affinities. Peptide maps generated by limited proteolysis with Staphylococcal V8 protease, Sharma et al., *J. Biol. Chem.*, 259:9248 (1984), have suggested that the 61 and 63 kDa proteins have different amino acid sequences.

The cGMP-stimulated PDEs (cGS-PDEs) are proposed to have a noncatalytic, cGMP-specific site that may account for the stimulation of cAMP hydrolysis by cGMP. Stoop et al., *J. Biol. Chem.*, 264:13718 (1989). At physiological cyclic nucleotide concentrations, this enzyme responds to elevated cGMP concentrations with an enhanced hydrolysis of cAMP. Thus, cGS-PDE allows for increases in cGMP concentration to moderate or inhibit cAMP-mediated responses. The primary sequence presented recently in LeTrong et al., *Biochemistry*, 29:10280 (1990), co-authored by the inventors herein, provides the molecular framework for understanding the regulatory properties and domain substructure of this enzyme and for comparing it with other PDE isozymes that respond to different signals. This publication also notes the cloning of a 2.2 kb bovine adrenal cortex cDNA fragment encoding cGS-PDE. See also, Thompson et al., *FASEB J.*, 5(6):A1592 (Abstract No. 7092) reporting on the cloning of a "Type II PDE" from rat pheochromocytoma cells.

With the discovery of the large number of different PDEs and their critical role in intracellular signalling, efforts have focused on finding agents that selectively activate or inhibit specific PDE isozymes. Agents which affect cellular PDE activity, and thus alter cellular cAMP, can potentially be used to control a broad range of diseases and physiological conditions. Some drugs which raise cAMP levels by inhibiting PDEs are in use, but generally act as broad nonspecific inhibitors and have deleterious side effects on cAMP activity in nontargeted tissues and cell types. Accordingly, agents are needed which are specific for selected PDE isozymes. Selective inhibitors of specific PDE isozymes may be useful as cardiotonic agents, anti-depressants, anti-hypertensives, anti-thrombotics, and as other agents. Screening studies for agonists/antagonists have been complicated, however, because of difficulties in identifying the particular PDE isozyme present in a particular assay preparation. Moreover, all PDEs catalyze the same basic reaction; all have overlapping substrate specificities; and all occur only in trace amounts.

Differentiating among PDEs has been attempted by several different means. The classical enzymological approach of isolating and studying each new isozyme is hampered by current limits of purification techniques and by the inability to accurately assess whether complete resolution of an isozyme has been achieved. A second approach has been to identify isozyme-specific assay conditions which might favor the contribution of one isozyme and minimize that of others. Another approach has been the immunological identification and separation into family groups and/or individual isozymes. There are obvious problems with each of these approaches; for the unambiguous identification and study of a particular isozyme, a large number of distinguishing criteria need to be established, which is often time consuming and in some cases technically quite difficult. As a result, most studies have been done with only partially pure PDE preparations that probably contained more than one isozyme. Moreover, many of the PDEs in most tissues are very susceptible to limited proteolysis and easily form active proteolytic products that may have different kinetic, regulatory, and physiological properties from their parent form.

The development of new and specific PDE-modulatory agents would be greatly facilitated by the ability to isolate large quantities of tissue-specific PDEs by recombinant means. Relatively few PDE genes have been cloned to date and of those cloned, most belong to the cAMP-specific family of phosphodiesterases (cAMP-PDEs). See Davis, "Molecular Genetics of the Cyclic Nucleotide Phosphodiesterases", pp. 227–241 in *Cyclic Nucleotide Phosphodiesterases: Structure, Regulation, and Drug Action*, Beavo, J. and Houslay, M. D., Eds.; John Wiley & Sons, New York; 1990. See also, e.g., Faure et al., *PNAS (USA)*, 85:8076 (1988)—*D. discoideum*; Sass et al., *PNAS (USA)*, 83:9303 (1986)—*S. cerevisiae*, PDE class IV, designated PDE2; Nikawa et al., *Mol. Cell. Biol.*, 7:3629 (1987)—*S. cerevisiae*, designated PDE1; Wilson et al., *Mol. Cell. Biol.*, 8:505 (1988)—*S. cerevisiae*, designated SRA5; Chen et al., *PNAS (USA)*, 83:9313 (1986)—*D. melanogaster*, designated dnc$^+$; Ovchinnikow et al., *FEBS*, 223:169 (1987)—bovine retina, designated GMP PDE; Davis et al., *PNAS (USA)*, 86:3604 (1989)—rat liver, designated rat dnc-1; Colicelli et al., *PNAS (USA)*, 86:3599 (1989)—rat brain, designated DPD; Swinnen et al., *PNAS (USA)*, 86:5325 (1989)—rat testis, rat PDE1, PDE2, PDE3 and PDE4; and Livi et al., *Mol. Cell. Biol.*, 10:2678 (1990)—human monocyte, designated hPDE1. See also, LeTrong et al., supra and Thompson et al., supra.

Complementation screening has been used to detect and isolate mammalian cDNA clones encoding certain types of PDEs. Colicelli et al., *PNAS (USA)*, 86:3599 (1989), reported the construction of a rat brain cDNA library in an *S. cerevisiae* expression vector and the isolation therefrom of genes having the capacity to function in yeast to suppress the phenotypic effects of RAS2$^{va119}$, a mutant form of the RAS2 gene analogous to an oncogenic mutant of the human HRAS gene. A cDNA so cloned and designated DPD (rat dunce-like phosphodiesterase) has the capacity to complement or "rescue" the loss of growth control associated with an activated RAS2$^{va119}$ gene harbored in yeast strain TK161-R2V (A.T.C.C. 74050), as well as the analogous defective growth control phenotype of the yeast mutant 10DAB (A.T.C.C. 74049) which is defective at both yeast PDE gene loci (pde$^{-1}$, pde$^{-2}$). The gene encodes a high-affinity cAMP specific phosphodiesterase, the amino acid sequence of which is highly homologous to the cAMP-specific phosphodiesterase encoded by the dunce locus of *Drosophila melanogaster*.

Through the date of filing of parent application Ser. No. 07/688,356, there have been no reports of the cloning and expression of DNA sequences encoding any of the mammalian Ca$^{2+}$/calmodulin stimulated or cGMP-stimulated PDEs (PDE families I and II) and, accordingly, there continues to exist a need in the art for complete nucleotide sequence information for these PDEs.

BRIEF SUMMARY OF THE INVENTION

The present invention provides novel purified and isolated polynucleotide sequences (e.g. DNA and RNA including sense and antisense strands) which code for expression of mammalian species (e.g., human and bovine) Ca$^{2+}$/calmodulin stimulated cyclic nucleotide phosphodiesterase and cGMP stimulated cyclic nucleotide phosphodiesterase polypeptides. Genomic and cDNA sequences provided by the invention may be associated with homologous or heterologous species expression control DNA sequences such as promoters, operators, regulators, terminators and the like to allow for in vivo and in vitro transcription to messenger RNA and, in turn, translation of mRNAs to provide functional phosphodiesterases and related polypeptides in large quantities.

Specifically provided by the invention are mammalian DNA sequences encoding phosphodiesterases and fragments thereof which are present as mammalian DNA inserts in bacterial plasmids and viral vectors which are the subject of deposits made with the American Type Culture Collection, 12301 Parklawn Drive, Rockville, Md. 20852 on Apr. 11 and 15, 1991 and on Apr. 14, 1992 in accordance with U.S.

Patent and Trademark Office and Budapest Treaty requirements. DNAs deposited in connection with the present invention include:

1. Plasmid pCAM-40 in *E. coli* (A.T.C.C. accession No. 68576) containing a bovine brain cDNA insert encoding a 61 kDa CaM-PDE isozyme;

2. Plasmid p12.3A in *E. coli* (A.T.C.C. 68577) containing a bovine brain cDNA insert encoding a 63 kDa CaM-PDE isozyme;

3. Bacteriophage λ CaM H6a (A.T.C.C. accession No. 75000) containing a human hippocampus cDNA insert fractionally encoding a 61 kDa CaM-PDE isozyme;

4. Plasmid pHcam61-6N-7 in *E. coli* (A.T.C.C. accession No. 68963) containing a composite human cDNA insert encoding a 61 kDa CaM-PDE isozyme;

5. Plasmid pcamH3EF in *E. coli* (A.T.C.C. accession No. 68964) containing a human hippocampus cDNA insert encoding a novel PDE homologous to a 61 kDa CaM-PDE;

6. Plasmid pcamHella in *E. coli* (A.T.C.C. accession No. 68965) containing a human heart cDNA insert encoding a novel PDE homologous to a 61 kDa CaM-PDE;

7. Plasmid p3CGS-5 in *E. coli* (A.T.C.C. accession No. 68579) containing a bovine adrenal cDNA insert encoding a cGS-PDE isozyme;

8. Plasmid pBBCGSPDE-5 in *E. coli* (A.T.C.C. accession No. 68578) containing a bovine brain cDNA insert encoding a cGS-PDE isozyme fragment;

9. Plasmid pBBCGSPDE-7 in *E. coli* (A.T.C.C. accession No. 68580) containing a bovine brain cDNA encoding a cGS-PDE isozyme;

10. Plasmid pGSPDE6.1 in *E. coli* (A.T.C.C. accession No. 68583) containing a human heart cDNA encoding a cGS-PDE isozyme fragment;

11. Plasmid pGSPDE7.1 in *E. coli* (A.T.C.C. accession No. 68585) containing a human hippocampus cDNA insert encoding a cGS-PDE isozyme fragment; and 12. Plasmid pGSPDE9.2 (A.T.C.C. accession No. 68584) containing a human hippocampus cDNA insert encoding a cGS-PDE isozyme fragment.

13. Plasmid pHcgs6n in *E. coli* (A.T.C.C. accession No. 68962) containing a human cDNA insert encoding a cGS-PDE.

Also specifically provided by the present invention is a bovine cDNA sequence containing nucleotides encoding bovine 59 kDa CaM-PDE and characterized by the DNA and amino acid sequences of SEQ ID NO: 16 and SEQ ID NO: 17.

In related embodiments, the invention concerns DNA constructs which comprise a transcriptional promoter, a DNA sequence which encodes the PDE or a fragment thereof, and a transcriptional terminator, each operably linked for expression of the enzyme or enzyme fragment. The constructs are preferably used to transform or transfect host cells, preferably eukaryotic cells, and more preferably mammalian or yeast cells. For large scale production, the expressed PDE can be isolated from the cells by, for example, immunoaffinity purification.

Incorporation of DNA sequences into procaryotic and eucaryotic host cells by standard transformation and transfection processes, potentially involving suitable DNA and RNA viral vectors and circular DNA plasmid vectors, is also within the contemplation of the invention and is expected to provide useful proteins in quantities heretofore unavailable from natural sources. Systems provided by the invention include transformed *E. coli* cells, including those referred to above, as well as other transformed eukaryotic cells, including yeast and mammalian cells. Use of mammalian host cells is expected to provide for such post-translational modifications (e.g., truncation, lipidation, and tyrosine, serine or threonine phosphorylation) as may be needed to confer optimal biological activity on recombinant expression products of the invention.

Novel protein products of the invention include expression products of the aforementioned nucleic acid sequences and polypeptides having the primary structural conformation (i.e., amino acid sequence) of CaM-PDE and cGS-PDE proteins, as well as peptide fragments thereof and synthetic peptides assembled to be duplicative of amino acid sequences thereof. Proteins, protein fragments, and synthetic peptides of the invention are projected to have numerous uses including therapeutic, diagnostic, and prognostic uses and will provide the basis for preparation of monoclonal and polyclonal antibodies specifically immunoreactive with the proteins of the invention.

Also provided by the present invention are antibody substances (including polyclonal and monoclonal antibodies, chimeric antibodies, single chain antibodies and the like) characterized by their ability to bind with high immunospecificity to the proteins of the invention and to their fragments and peptides, recognizing unique epitopes which are not common to other proteins. The monoclonal antibodies of the invention can be used for affinity purification of CaM-PDEs and cGS-PDEs, e.g., Hansen et al., *Meth. Enzymol.*, 159:543 (1988).

Also provided by the present invention are novel procedures for the detection and/or quantification of normal, abnormal, or mutated forms of CaM-PDEs and cGS-PDEs, as well as nucleic acids (e.g., DNA and mRNA) associated therewith. Illustratively, antibodies of the invention may be employed in known immunological procedures for quantitative detection of these proteins in fluid and tissue samples., and of DNA sequences of the invention that may be suitably labelled and employed for quantitative detection of mRNA encoding these proteins.

Among the multiple aspects of the present invention, therefore, is the provision of (a) novel CaM-PDE and cGS-PDE encoding polynucleotide sequences, (b) polynucleotide sequences encoding polypeptides having the activity of a mammalian CaM-PDE or of a mammalian cGS-PDE which hybridize to the novel CaM-PDE and cGS-PDE encoding sequences under hybridization conditions of the stringency equal to or greater than the conditions described herein and employed in the initial isolation of cDNAs of the invention, and (c) polynucleotide sequences encoding the same (or allelic variant or analog polypeptides) through use of, at least in part, degenerate codons. Correspondingly provided are viral DNA and RNA vectors or circular plasmid DNA vectors incorporating polynucleotide sequences and procaryotic and eucaryotic host cells transformed or transfected with such polynucleotide sequences and vectors, as well as novel methods for the recombinant production of these proteins through cultured growth of such hosts and isolation of the expressed proteins from the hosts or their culture media.

In yet other embodiments, the invention provides compositions and methods for identifying compounds which can modulate PDE activity. Such methods comprise incubating a compound to be evaluated for PDE modulating activity with eukaryotic cells which express a recombinant PDE polypeptide and determining therefrom the effect of the compound on the phosphodiesterase activity provided by gene expression. The method is effective with either whole cells or cell lysate preparations. In a preferred embodiment, the eukaryotic cell is a yeast cell or mammalian cell which lacks endogenous phosphodiesterase activity. The effect of the compound on phosphodiesterase activity can be determined by means of biochemical assays which monitor the hydrolysis of cAMP and/or cGMP, or by following the effect of the compound on the alteration of a phenotypic trait of the eukaryotic cell associated with the presence or absence of the recombinant PDE polypeptide.

Other aspects and advantages of the present invention will be apparent upon consideration of the following detailed description thereof which includes numerous illustrative examples of the practice of the invention, reference being made to the drawing wherein:

FIG. 1A through 1C provides the results of amino acid sequence determinations for isolated 59 kDa (bovine heart) and 63 kDa (bovine brain) CaM-PDE proteins in alignment with the complete sequence of the 61 kDa (bovine brain) isozyme. Identities of the 59 and 63 kDa proteins to the 61 kDa isozyme are underlined. Tentative identifications are in lower cases and hyphens denote unidentified residues. The N-terminus of the 59 kDa isozyme, as determined by the subtraction of a methionyl peptide (mDDHVTIRRK) from the composition of an amino-terminal blocked lysyl peptide, is in parenthesis. Solid boxes are placed above residues within the CaM-binding sites identified in the 61 and 59 kDa isozymes.

DETAILED DESCRIPTION OF THE INVENTION

Figure 1A:
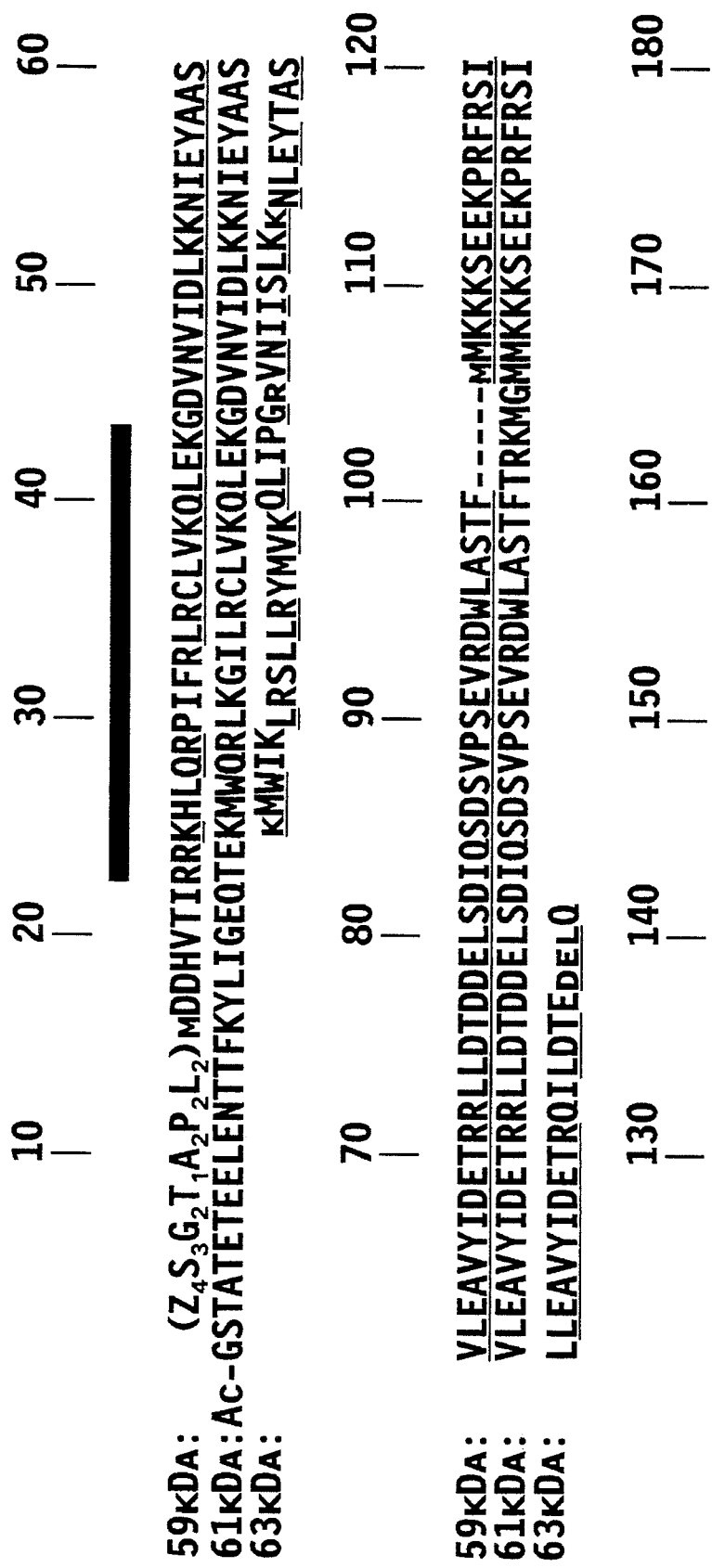

The following examples illustrate practice of the invention. Example I relates to the isolation, purification, and sequence determination of 61 kDa CaM-PDE cDNA from bovine brain and to the expression thereof in a mammalian host cell. Example II relates to the isolation, purification, and sequence determination of a 59 kDa CaM-PDE from bovine lung and to the expression thereof in a mammalian host cell. Example III relates to the isolation, purification, and sequence determination of 63 kDa CaM-PDE cDNA from bovine brain and to the expression thereof in a mammalian host cell. Example IV relates to the isolation, purification, and sequence determination of cGS-PDE cDNA from bovine adrenal cortex, as well as the expression of the DNA in mammalian host cells. Example V relates to the isolation, purification, and sequence determination of cGS-PDE cDNA from bovine brain and to the expression thereof in a mammalian host cell. Example VI relates to the use of cGS-PDE bovine adrenal cDNA to obtain human cGS-PDE cDNAs and to the development of a human cDNA encoding a cGS-PDE. Example VII relates to the use of CaM-PDE 61 kDa bovine brain cDNA to obtain a human CaM-PDE 61 kDa cDNA and a novel structurally related cDNA. Example VIII relates to the expression of bovine and human PDE cDNAs for complementation of yeast phenotypic defects and verification of phosphodiesterase activity for the expression product. Example IX relates to tissue expression studies involving Northern analysis and RNase protection studies employing polynucleotides (specifically cDNAs and antisense RNAs) of the invention.

In those portions of the text addressing the formation of redundant oligonucleotides, the following Table I single letter code recommendations for ambiguous nucleotide sequence, as reported in *J. Biol. Chem.*, 261:13–17 (1986), are employed:

TABLE I

| Symbol | Meaning | Origin of designation |
|---|---|---|
| G | G | Guanine |
| A | A | Adenine |
| T | T | Thymine |
| C | C | Cytosine |
| R | G or A | puRine |
| Y | T or C | pYrimidine |
| M | A or C | aMino |
| K | G or T | Keto |
| S | G or C | Strong interaction (3 H bonds) |
| W | A or T | Weak interaction (2 H bonds) |
| H | A, C, or T | not G, as H follows G in the alphabet |
| B | G, C, or T | not A |
| V | A, C, or G | not T, (not U) as V follows U |
| D | A, G, or T | not C |
| N | A, C, G, or T | any Nucleotide base |

EXAMPLE I

Isolation, Purification, and Sequence Determination of 61 kDa CaM-PDE cDNA From Bovine Brain In this Example, a cDNA sequence representing that portion of a gene for 61 kDa bovine brain CaM-PDE which encodes the amino terminus of the protein was isolated by PCR from a collection of first strand cDNAs developed from bovine brain mRNA. The PCR-generated fragment was then employed to isolate a full length bovine brain CaM-PDE sequence.

Total RNA was prepared from bovine heart using the method of Chomczynski et al., *Anal. Biochem.*, 162:156–159 (1987) and mRNA was selected using a Poly(A) QuikTm mRNA purification kit according to the manufacturer's protocol. First strand cDNA was synthesized by adding 80 units of AMV reverse transcriptase to a reaction mixture (40 μl, final volume) containing 50 mM Tris HCl (pH8.3 @ 42°), 10 mM MgCl$_2$, 10 mM dithiothreitol, 0.5 mM (each) deoxynucleotide triphosphates, 50 mM KCl, 2.5 mM sodium pyrophosphate, 5 μg deoxythymidylic acid oligomers (12–18 bases) and 5 μg bovine heart mRNA denatured for 15 min at 65°. Incorporation of 1 μl [$^{32}$P]-labeled dCTP (3000 Ci/mmol) was used to quantitate first strand cDNA synthesis. The reaction was incubated at 42° for 60 min. The reaction was phenol/CHCl$_3$ extracted and EtOH precipitated. The nucleic acid pellet was resuspended in 50 μl of 10 mM Tris-HCl (pH 7.5)/0.1 mM EDTA to a final concentration of 15 ng per μl.

Redundant sense and antisense oligomers corresponding to 61 kDa peptide sequences as in FIG. 1A through 1C were designed to be minimally redundant, yet long enough to specifically hybridize to the target template.

A first 23 base oligomer, designated CaM PCR-2S, was synthesized on an Applied Biosystems, Inc. DNA synthesizer. The oligomer had the following sequence,

SEQ ID NO: 1
5'-AARATGGGNATGAARAARAA-3' which specifies the following amino acid sequence,

---
SEQ ID NO: 2
KMGMMKKK.

---

A second 23 base oligomer, designated CaM PCR-3AS, was synthesized with the following sequence,

---
SEQ ID NO: 3
5'-ACRTTCATYTCYTCYTCYTGCAT-3'

--- representing the following amino acid sequence,

---
SEQ ID NO: 4
MQEEEMNV.

---

A 612 bp CaM PDE cDNA fragment was synthesized using the PCR amplification technique by adding 15 ng of first strand cDNA to a reaction mixture containing 50 mM KCl, 10 mM Tris-HCl (pH 9.0), 1.5 mM $MgCl_2$, 0.01% gelatin, 0.1% Triton X-100, 0.2 mM (each) deoxynucleotide triphosphates, 1 μM (each) CaM PCR 2S and CaM PCR-3AS oligomers, and 2.5 units of *Thermus aquaticus* DNA polymerase. The reaction was incubated for 30 cycles as follows: 94° for 1 min; 50° for 2 min; and 72° for 2 min. The reaction products were purified on a 1% agarose gel using 0.04M Tris-acetate/0.001M EDTA buffer containing 0.5 μg/ml ethidium bromide. The DNA products were visualized with UV light, cleanly excised from the gel with a razor blade, purified using Geneclean II reagent kit and ligated into Eco RV-cut pBluescript vector DNA.

To determine if the PCR amplification products were CaM PDE cDNAs, the subcloned PCR DNA products were sequenced from the ends using T3 and T7 promoter primers and either Sequenase or Taq Polymerase sequencing kits. Approximately 250 bases from each end of this piece of DNA were sequenced and the deduced amino acid sequence from the cDNA corresponded with the FIG. 1A and 1C amino acid sequences of the 59 and 61 kDa CaM-PDEs, confirming that the PCR DNA product was a partial CaM PDE cDNA.

A bovine brain cDNA library constructed with the lambda ZAP vector (kindly provided by Ronald E. Diehl, Merck, Sharp & Dohme) was screened with the radiolabeled 615 bp CaM-PDE cDNA obtained by PCR amplification. The probe was prepared using the method of Feinberg et al., *Anal. Biochem.*, 137:266–267 (1984), and the [$^{32}$P]-labeled DNA was purified using Elutip-D® columns. Plaques (700,000 plaques on 12–150 mm plates) bound to filter circles were hybridized at 42° C. overnight in a solution containing 50% formamide, 20 mM Tris-HCl (pH 7.5), 1× Denhardt's solution, 10% dextran sulfate, 0.1% SDS and $10^6$ cpm/ml [$^{32}$P]-labeled probe ($10^9$ cpm/μg). The filters were washed three times for 15 min with 2× SSC/0.1% SDS at room temperature, followed by two 15-min washes with 0.1× SSC/0.1% SDS at 45° C. The filters were exposed to x-ray film overnight.

Of the fifty-six plaques that hybridized with the [$^{32}$P]-labeled probes eight randomly selected clones were purified by several rounds of re-plating and screening [Maniatis et al., *Molecular Cloning: A Laboratory Manual* 545 pp. Cold Spring Harbor Laboratory, Cold Spring Harbor, N.Y., (1982)] and the insert cDNA's were subcloned into pBluescript SK(–) by in vivo excision [Short et al., *Nuc. Acids Res.*, 16:7583–7599 (1988)] as recommended by the manufacturer.

Plasmid DNA prepared from cultures of each clone were subjected to restriction analysis using EcoRI. Two clones of a suitable length were selected for sequence analysis using Taq Tak® and Sequenase® sequencing kits. The two clones were pCAM-40 (2.3 kb) and pCAM-34 (2.7 kb). The sequencing information from this procedure confirmed that the insert of pCAM-40 encoded the full length bovine brain 61 kDa CaM-PDE. The sequence of this clone and the amino acid sequence deduced therefrom are set forth in SEQ ID NO: 5 and SEQ ID NO: 6.

Transient expression of the 61 kDa CaM-PDE cDNA in COS-7 cells (A.T.C.C. CRL 1651) was accomplished as follows. Vector pCDM8 [Seed, *Nature*, 329:840–843 (1987)] in *E. coli* host cells MC1061-p3 was generously provided by Dr. Brian Seed, Massachusetts General Hospital, Boston, Mass. This vector is also available from Invitrogen, Inc. (San Diego, Calif.). Plasmid pCAM-40 was digested with HindIII and NotI, yielding a 2.3 kb fragment which was ligated into CDM8 vector DNA which had been digested with HindIII and NotI. The resulting plasmid was propagated in MC1061-p3 cells. Plasmid DNA was prepared using the alkaline lysis method of Ausubel et al., eds., *Current Protocols in Molecular Biology*, 1:1.7.1 (John Wiley & Sons, New York, 1989) and purified using Qiagen-Tip 500 columns (Qiagen, Inc. Chatsworth, Calif.) according to the manufacturer protocol.

COS-7 cells were transfected with the p-CAM-40/CDM8 construct (or mock transfected with the CDM8 vector alone) using the DEAE-dextran method Ausubel et al., supra at 1:9.2 et seq. Specifically, 10 μg of ethanol precipitated DNA was resuspended in 80 μl TBS buffer, and added to 160 μl of 10 mg per ml DEAE-dextran dropwise to a 100 mm plate of 50% confluent COS-7 cells in 4 ml of DMEM supplemented with 10% NuSerum, and mixed by swirling. The cells were incubated for 3–4 hours at 37° in a water-saturated 7% $CO_2$ atmosphere. The medium was removed and the cells were immediately treated with 10% DMSO in PBS for 1 minute. Following this treatment, the cells were washed with PBS, then DMEM, and finally cultured in DMEM supplemented with 10% fetal bovine serum and antibiotics (50 μg/ml streptomycin sulfate) in a 7%-$CO_2$ incubator for 36 hours.

COS cells were scraped from the plates and homogenized in a buffer containing 40 mM Tris-HCl (pH=7.5), 5 mM EDTA, 15 mM benzamidine, 15 mM beta-mercaptoethanol, 1 μg per ml pepstatin A and 1 μg per ml peupeptin using a Dounce homogenizer (1 ml per 100 mm plate). Homogenates were assayed for PDE activity according to the procedures of Hanson et al., *Proc. Nat'l. Acad. Sci., U.S.A.*, 79:2788–2792 (1982), using [$^3$H]cGMP as the substrate. Reactions were carried out at 30° for 10 minutes in a buffer containing 20 mM Tris-HCl (pH=7.5), 20 mM imidazole (pH=7.5), 3 mM $MgCl_{b\ 2}$, 15 mM Mg acetate, 0.2 mg per ml BSA and 1 μM $^3$H-cAMP with either 2 mM EGTA or 0.2 mM $CaCl_2$ and 4 μg per ml CaM. Assays were stopped by incubating the tubes in a 90° water bath for 1 minute. After cooling, 10 μl of 2.5 mg per ml snake venom was added to each assay and incubated at 37° for 5 minutes. The samples were diluted with 250 μl of 20 mM Tris-HCl (pH=7.5) and immediately applied to 0.7 ml A-25 ion exchange columns. The columns were washed three times with 0.5 ml of 20 mM Tris-HCl (pH=7.5) and the eluate was collected in scintillation vials. Samples were counted for 1 minute using a Packard Model 1600TR scintillation counter. Specific cyclic nucleotide hydrolytic activity was expressed as picomoles cAMP or cGMP hydrolyzed per minute per mg protein. Protein concentration was estimated according to the method of Bradford, *Anal. Biochem.*, 72:248–254 (1976), using BSA as a standard. When compared to mock transfected cells, extracts of cells transfected with pCAM-40 cDNA contained significantly greater CAMP and cGMP hydrolytic activities in the presence of EGTA. Assays of the pCAM-40 cDNA-transfected cells in the presence of calcium and CaM resulted in stimulation of cAMP and cGMP hydrolysis.

EXAMPLE II

Isolation, Purification, and Sequence Determination of a 59 kDa CaM-PDE From Bovine Lung A fully degenerate sense oligonucleotide corresponding to the amino acid sequence

SEQ ID NO: 7
MDDHVTI from the bovine heart 59 kDa CaM-pde was synthesized. The nucleotide sequence of this oligonucleotide is

SEQ ID NO: 8
5'-ATGAGRAGRCAYGTHACNAT-3'.

An antisense oligonucleotide was designed from the FIG. 1A through 1C sequence of bovine brain 61 kDa CaM-PDE, corresponding to the amino acid sequence

SEQ ID NO: 9
LRCLVKQ and having the sequence,

SEQ ID NO: 10
5'-CTGCTTCACTAAGCATCTTAG-3'.

This primer pair was used to prime a PCR reaction using bovine heart first strand cDNA (as prepared in Example I) as a template. This predicted a PCR product of 75 bp, 54 bp of which were unique 59 kDa sequence and 21 bp of which were shared between the 59 kDa and 61 kDa isozymes. The PCR products were analyzed by sieving agarose gel electrophoresis, and a band migrating at 75 bp was excised from the gel. The DNA was subcloned into pBluescript KS$^+$, and colonies positive by the blue/white selection scheme were screened by PCR using primers directed against vector sequences. Colonies with inserts of the appropriate size were selected, and one of these (pCaM59/75.14) was chosen for sequencing. Plasmid DNA was prepared using a Qiagen P20 push column and used as template for sequencing using the dideoxy method. The sequence of the PCR product is SEQ ID NO: 11
5'-ATGAGAAGGCACGTAACGATCAGGAGGAAACATCTCCAA
AGACCCATCTTT—AGACTAAGATGCTTAGTGAAGCAG-3'.

Analysis of the sequence revealed differences in two codons between the sequence obtained and the predicted sequence. Re-examination of the sense oligonucleotide primer sequence revealed that an inadvertent transposition of two codons had led to a mistake in the design of the oligonucleotide. A second set of oligonucleotide PCR primers was prepared which predicted a 54 bp product with minimum overlap between the 59 and 61 kDa isozymes; in addition, the second sense primer incorporated a correction of the mistake in the design of the original sense primer. The sense oligonucleotide had the sequence

SEQ ID NO: 12
5'-ATGGAYGAYCACGTAACGATC-3' and the antisense oligonucleotide had the sequence

SEQ ID NO: 13
5'-AAGTATCTCATTGGAGAACAG-3'

This primer pair was used to prime a PCR reaction using bovine heart first-strand cDNA as template and the PCR products subcloned and screened exactly as described above. Two clones (pCaM59/54.9 and pCaM59/54.10) were selected for sequencing based on insert size and sequenced as described above; both clones contained 54 bp inserts of the predicted sequence

SEQ ID NO: 14
5'-ATGGATGATCACGTAACGATCAGGAGGAAACATCTCCAAA
GACCCATCT-TTAGA-3', predicting the amino acid sequence

SEQ ID NO: 15
MDDHVTIRRKHLQRPIFR

A cDNA library was constructed from bovine lung mRNA and screened using procedures as described in Example IV, infra, with respect to screening of a bovine adrenal cortex library. Approximately $1.2 \times 10^6$ plaque-forming units were probed with a $^{32}$P-labelled, 1.6 kb EcoRI restriction endonuclease-cleavage product of the pCAM-40 cDNA. This initial screening produced 4 putative 59 kDA CaM-PDE cDNA clones. Preliminary sequence analysis indicated that one clone, designated p59KCAMPDE-2, contained the complete coding sequence of the putative 59 kDa CaM-PDE. A series of nested deletions were constructed from the p59KCAMPDE-2 plasmid [See, Sonnenburg et al., *J. Biol. Chem.*, 266 (26): 17655–17661 (1991)], and the resultant templates were sequenced by an adaptation of the method of Sanger using the Taq DyeDeoxy™ Terminator Cycle Sequencing Kit and an Applied Biosystems Model 373A DNA Sequencing System. The DNA and deduced amino acid sequences are set out in SEQ. ID NO: 16 and 17, respectively. A large open reading frame within the cDNA encodes a 515 residue polypeptide with an estimated molecular weight of≈59 kilodaltons that is nearly identical to the 61 kDa CaM-PDE amino acid sequence except for the amino-terminal 18 residues. Moreover, the predicted amino acid sequence of the p59KCAMPDE-2 open reading frame is identical to the available sequence of the 59 kDa CaM-PDE purified from bovine heart, Novack et al., *Biochemistry*, 30: 7940–7947 (1991). These results indicate that the p59KCAMPDE-2 cDNA represents an mRNA species encoding the 59 kDa CaM-PDE.

Transient expression of the 59 kDa bovine lung PDE was accomplished as in Example I. Specifically, a 2.66 kb, EcoRI/blunt-ended fragment of p59KCAMPDE-2 cDNA was subcloned into pCDM8 which had been digested with XhoI and blunt-ended. The recombinant plasmid, designated p59KCAMPDE-2/CDM8, was used to transiently transfect COS-7 cells and extracts prepared from transfected COS-7 cells were assayed for CaM-PDE activity using 2 μM cAMP. COS-7 cells transfected with the p59KCAMPDE-2 cDNA yielded a cAMP hydrolytic activity that was stimulated 4–5 fold in the presence of calcium and calmodulin. Mock transfected COS-7 cells had no detectable calmodulin-stimulated cAMP hydrolytic activity.

EXAMPLE III

Isolation, Purification, and Sequence Determination of 63 kDa CaM-PDE cDNA From Bovine Brain Multiple fully and partially redundant oligonucleotides corresponding to the amino acid sequence reported in FIG. 1A through 1C were synthesized for use in attempting to obtain a cDNA clone for the 63 kDa CaM-PDE. Annealing temperatures used for the polymerase chain reactions were varied between 2° to 20° C. below the theoretical melting temperature for the lowest melting oligonucleotide of each sense-antisense pair. Except for probes 63-12s and 63-13a, which are discussed below, the PCR products of each of the oligonucleotide pairs under a wide range of conditions gave multiple ethidium bromide bands when agarose gel-electrophoresed. Use of 63-12s and 63-13a resulted in a PCR product that coded for 63 kDa CaM-PDE when sequenced.

A fully redundant sense 23-mer oligonucleotide, designated 63-12s, was assembled having the following sequence

| SEQ ID NO: 18 |
| --- |
| 5'ATHCAYGAYTAYGARCAYACNGG-3' | based on an amino acid sequence,

| SEQ ID NO: 19 |
| --- |
| IHDYEHTG | which is conserved in the 61 kDa bovine CaM-PDEs (see FIG. 1A through 1C). A partially redundant antisense 32-mer oligonucleotide, designated 63-13a, had the sequence

| SEQ ID NO: 20 |
| --- |
| 5'-TCYTTRTCNCCYTGNCGRAARAAYTCYTCCAT-3' | and was based on the following conserved sequence in the 63 kDa CaM-PDE,

| SEQ ID NO: 21 |
| --- |
| MEEFFRQGDKE |

Messenger RNA was prepared from bovine brain cerebral cortex and poly A$^+$ selected. First strand complementary DNA was produced using AMV or MMLV reverse transcriptase. De-tritylated oligonucleotides were phosphorylated using 1 mM [γ-$^{32}$P]ATP at 1×10$^6$ cpm/nmol and T4 polynucleotide kinase. After separation of 5' $^{32}$P-labelled oligonucleotides from free ATP using NENsorb 20 columns, each was suspended as a 20 μM (5' phosphate) stock and combined finally at 400 nM each in the PCR. The reaction was run using 50 ng total cDNA and 200 μM dNTP to obtain about 1 μg of PCR product. The reaction had an initial denaturation step at 94° C. for 5 min followed by 30 cycles of a 1 min 94° C. denaturation, an annealing step at 50° C. for 1 min, and a 2 min extension step at 72° C. Under the reaction conditions, a single ethidium bromide-staining band of 450 base pairs was obtained on agarose gel electrophoresis of 100 ng of the PCR product. Five μg of 5' phosphorylated PCR product was ligated to 15 ng EcoRV-cut Bluescript KS(+) plasmid using T4 DNA ligase in 5% PEG-6000 for 12 h at 21° C. Putative positives of XL 1-blue transformations were white colonies using isopropyl thiogalactoside (IPTG) and bromo- chloro- indolyl galactoside (Xgal) for chromogenic selection. Such picks were sequenced using T3 or T7 primers, dideoxynucleotide terminators, and Sequenase.

One resultant clone (p11.5B) had the nucleotide sequence and translated amino acid sequence provided in SEQ ID NO: 22 and SEQ ID NO: 23, respectively. The codons for the amino acids YEH found in oligonucleotide 63-12s were replaced by codons for the amino acid sequence NTR in p11.5B. This was probably due to a contaminant in 63-12s. Since the translated open reading frame (ORF) was similar to that reported in FIG. 1A through 1C for the 63 kDa CaM PDE, p11.5B was used to screen a bovine brain cDNA library for a full length cDNA clone.

A bovine brain cDNA library was constructed in γ ZAP II. First strand cDNA was treated with RNase H, E. coli DNA polymerase, and E. coli DNA ligase to synthesize second strand cDNA. The cDNA was blunt-ended by T4-DNA polymerase; EcoRI sites in the cDNA were protected with EcoRI methylase and S-adenosyl methionine and EcoRI linkers were ligated on with T4 DNA ligase. After EcoRI restriction endonuclease treatment, free linkers were separated from the cDNA by gel filtration over Sepharose CL-4B. γ ZAP II arms were ligated onto the cDNA and packaged by an in vitro Gigapack Gold packaging kit obtained from Stratagene. 9.5×10$^5$ recombinants were obtained with 5.8% nonrecombinant plaques as assessed by plating with IPTG and X-gal. The library was amplified once by the plate lysate method to obtain 1.4×10$^7$ pfu/ml.

An initial screen of a total bovine brain cDNA library in γ ZAP II was performed. 700,000 pfu were screened using $^{32}$P-labelled oligonucleotide 63-1s at a hybridization and wash temperature of 40° C. Oligonucleotide 63-1s was a fully redundant 23-mer having the sequence

| SEQ ID NO: 24 |
| --- |
| 5'-AARAARAAYYTNGARTAYACNGC-3' | corresponding to the amino acid sequence

| SEQ ID NO: 25 |
| --- |
| KKNLEYTA |

A total of 21 putative positives were picked. Subsequent rescreens were impeded by the very high background found using this screening method. Therefore, aliquots of each primary pick were pooled and 50,000 pfu of the pool were replated and rescreened with p11.5B radiolabelled by random primers and [α-$^{32}$P]dCTP. One positive was obtained, plaque-purified, and rescued as a plasmid p12.3a. Its DNA sequence is provided in SEQ ID NO: 26. Subsequently, the bovine brain cerebral cortex library was screened further with p11.5B. Two further independent clones, p12.27.9 and p12.27.11, were obtained out of a primary screen of 1.4×10$^6$ pfu. They were plaque-purified and rescued for sequencing.

Clone p12.3a codes for a protein sequence with most of the aligned peptides isolated from bovine 63 kDa CaM-PDE as shown in FIG. 1A through 1C. SEQ ID NO: 26 and SEQ ID NO: 27 set forth the coding region (i.e., the 1844 nucleotides of an approximately 2.5 kilobase insert) of p12.3a. Base numbers 248–290 code for amino acid sequence

| SEQ ID NO: 28 |
| --- |
| QLENGEVNIEELKK, | while the comparable (FIG. 1A through 1C) peptide has the sequence

| SEQ ID NO: 29 |
| --- |
| QLIPGRVNIISLKK |

Base numbers 942–990 code for an amino acid sequence

| SEQ ID NO: 30 |
| --- |
| KSECAILYNDRSVLEN | while the isolated (FIG. 1A through 1C) peptide sequence is

| SEQ ID NO: 31 |
| --- |
| KDETAILYNDRTVLEN. |

None of the nonaligned 63 kDa peptide sequence is found in any reading frame of p12.3a; also, the molecular weight of the p12.3a open reading frame, as translated, is 60,951 not 63,000. Therefore, this cDNA may represent an isozyme variant of the 63 kDa protein. The other two independent clones (p12.27.9 and p12.27.11) seem to have ORF sequence identical to p12.3a. The open reading frame of one clone begins at nucleotide number 823 of p12.3a and is identical to p12.3a through its termination codon. The other clone starts at nucleotide 198 and is identical to p12.3a throughout its length. None of the three clones has the anomalous NTR peptide sequence found in p11.5B; all three have YEH as the 61 kDa CaM PDE.

Transient expression of the 63 kDa CaM-PDE cDNA in COS-7 cells was accomplished as follows. A fragment of the cDNA insert of plasmid p 12.3 including the protein coding region of SEQ. ID NO: 26 and flanked by BamHI restriction sites was prepared by PCR. More specifically, oligonucleotides corresponding to base Nos. 94–117 (with the putative initiation codon) and the antisense of base Nos. 1719–1735 (with sequence immediately 3' of the termination codon) of SEQ. ID NO. 26 were synthesized with two tandem BamHI sites on their 5' ends. The two primers had the following sequences:

| SEQ.ID NO: 32 |
| --- |
| 5'-GGATCCGGATCCCGCAGACGGAGGCTGAGCATGG-3' |
| SEQ.ID NO: 33 |
| 5'-GGATCCGGATCCAGGACCTGGCCAGGCCCGGC-3' |

The two oligonucleotides were used in a PCR cycling 30 times from a 1 min incubation at 94° C. to a 2 min 72° C. incubation with a final 10 min extension reaction at 72° C. The 100 µl reaction used 20 µM of each oligonucleotide and 100 pg p12.3a as the template in order to produce 5 µg 1665 base pair product.

The product was extracted once with an equal volume of 1:1 phenol:chloroform, made 0.3M with regard to sodium acetate, and precipitated with two volumes of ethanol overnight. The precipitate was dried, rehydrated into 50 µl, and the cDNA was digested with 5 units BamHI restriction endonuclease for one hour at 37° C. Afterwards, the solution was extracted once with an equal volume of 1:1 phenol:chloroform. The 1641 base pair cDNA with BamHI 5' and 3' ends was purified from the aqueous layer using Qiagen Q-20 columns (Qiagen, Inc., Chatsworth, Calif.) and the protocol given by the manufacturer.

The cut, purified PCR product was ligated into BamHI digested, alkaline phosphatase-treated Bluescript KS(+) plasmid. The ligation product was subcloned into XL1 cells; resulting transformants were screened by sequencing. One transformant (designated p11.6.c6) was isolated with the BamHI insert oriented such that the Bluescript KS(+) HindIII restriction site was 30 bases 5' to the sequence of the insert encoding the initiation codon. This plasmid was digested with HindIII and XbaI restriction endonucleases to release the 1689 base pair fragment. The fragment was ligated into HindIII- and XbaI-digested CDM8 vector DNA as in Example I.

COS-7 cells were transfected with the p12.3.a/CDM8 construct or mock transfected with the CDM8 vector alone using the DEAE-dextran method as described in Example 1. A ratio of 10 µg DNA/400 µg DEAE-dextran was used, with a final DEAE-dextran concentration in the media of 100 µg/ml. After 48 h, cells were suspended in 1 ml of homogenization buffer (40 mM Tris HCl, pH=7.5, 15 mM benzamidine HCl, 15 mM β-mercaptoethanol, 0.7 µg/ml pepstatin A, 0.5 µg/ml leupeptin, and 5 mM $Na_4EDTA$) and disrupted on ice using a Dounce homogenizer. The homogenates were diluted ½ to make a final 50% (v/v) glycerol for storage at −20° C. and used either to assay for phosphodiesterase activity or to determine protein concentration. CaM-dependent and independent activities were determined as in Example 1. Cells transfected with a p12.3.a DNA had a 15-fold increase in CaM-stimulated cAMP phosphodiesterase activity and a 12-fold increase in CaM-stimulated cGMP phosphodiesterase activity over basal levels. Mock transfected COS-7 cells showed no PDE activity over basal levels even with CaM stimulation.

EXAMPLE IV

Isolation, Purification, Sequence Determination, and Expression of cGS-PDE cDNA From Bovine Adrenal Cortex Total RNA was prepared from bovine adrenal outer cortex using the method of Chomczynski et al., supra. Polyadenylated RNA was purified from total RNA preparations using the Poly(A) QuickTm mRNA purification kit according to the manufacturer's protocol. First strand cDNA was synthesized by adding 80 units of AMV reverse transcriptase to a reaction mixture (40 µl, final volume) containing 50 mM Tris-HCl (pH 8.3 @ 42°), 10 mM $MgCl_2$, 10 mM dithiothreitol, 0.5 mM (each) deoxynucleotide triphosphates, 50 mM KCl, 2.5 mM sodium pyrophosphate, 5 µg deoxythymidylic acid oligomers (12–18 bases) and 5 µg bovine adrenal cortex mRNA denatured for 15 min at 65° C. The reaction was incubated at 42° C. for 60 min. The second strand was synthesized using the method of Watson et al., *DNA Cloning: A Practical Approach*, 1:79–87 (1985) and the ends of the cDNA were made blunt with T4 DNA polymerase. EcoRI restriction endonuclease sites were methylated [Maniatis et al., supra] using a EcoRI methylase (Promega), and EcoRI linkers (50-fold molar excess) were ligated to the cDNA using T4 DNA ligase. Excess linkers were removed by digesting the cDNA with EcoRI restriction endonuclease, followed by Sepharose CL-4B chromatography. Ausubel et al., supra. The cDNA (25–50 ng per µg vector) was ligated into EcoRI-digested, dephosphorylated ZAP® II (Stratagene) arms [Short et al., *Nuc. Acids Res.*, 16:7583–7599 (1988)] and packaged [Maniatis et al., supra]

with Gigapack® Gold extracts according to the manufacturer's protocol.

Initially, an unamplified bovine adrenal cortex cDNA library was made and screened with a redundant 23-mer antisense oligonucleotide probes end-labeled with γ-[$^{32}$P] ATP and T4 polynucleotide kinase. The oligomers corresponding to the amino acid sequences SEQ ID NO: 34
EMMMYHMK
and
SEQ ID NO: 35
YHNWMHAF were made using an Applied Biosystems model 380A DNA synthesizer. Their sequences are as follows:

SEQ ID NO: 36
5'-TT CAT RTG RTA CAT CAT CAT YTC-3'
SEQ ID NO: 37
5'-AA NGC RTG CAT CCA RTT RTG RTA-3'

Duplicate nitrocellulose filter circles bearing plaques from 12 confluent 150 mm plates (approximately 50,000 pfu/plate) were hybridized at 45° C. overnight in a solution containing 6× SSC, 1× Denhardt's solution, 100 µg/ml yeast tRNA, 0.05% sodium pyrophosphate and $10^6$ cpm/ml radiolabeled probe (>$10^6$ cpm per pmol). The filters were washed three times in 6× SSC at room temperature, followed by a higher-stringency 6× SSC wash at 10° C. below the minimum melting temperature of the oligomer probes, and exposed to x-ray film overnight.

A single 2.1 kb cDNA clone (designated pcGS-3:2.1) was isolated and sequenced. The amino acid sequence enclosed by the large ORF of this clone was identical to peptide sequences of the cGS-PDE purified from the supernatant fraction of a bovine heart homogenate. LeTrong et al., supra.

A second, amplified, bovine adrenal cortex cDNA library was screened using the [$^{32}$P]-labeled CGS-3:2.1 partial cDNA, yielding a 4.2 kb cDNA (designated 3CGS-5).

The library was constructed, amplified as in Maniatis et al., supra, plated and screened with the bovine cDNA insert from clone CGS-3:2.1. The probe was prepared using the method of Feinberg et al., supra, and the radiolabeled DNA was purified using Elutip-D® columns. Plaques (600,000 pfu on twelve 150 mm plates) bound to filter circles were hybridized at 42° C. overnight in a solution containing 50% formamide, 20 mM Tris-HCl (pH 7.5, 1× Denhardt's solution, 10% dextran sulfate, 0.11% SDS and $10^6$ cpm/ml [$^{32}$P]-labeled probe ($10^9$ cpm/µg). The filters were washed three times for 15 minutes with 2× SSC/0.1% SDS at room temperature, followed by two 15-minute washes with 0.1× SSC/0.1% SDS at 45° C. The filters were exposed to x-ray film overnight. Ausubel et al., supra.

From this initial screening, 52 putative clones were identified. Twenty of these clones were randomly selected, purified by several rounds of re-plating and screening [Maniatis et al., supra] and the insert cDNAs were subcloned into pBluescript SK(−) by in vivo excision [Short et al., supra] as recommended by the manufacturer. Plasmid DNA prepared from these clones were analyzed by restriction analysis and/or sequencing. From this survey, a 4.2 kb cDNA representing the largest open reading frame was identified. The cDNA inserts from the other putative clones were shorter, and appeared to be identical based on the nucleotide sequence of the insert ends.

Putative cGS-PDE cDNAs were sequenced by a modification of the Sanger method [Sanger et al., *Proc. Natl. Acad. Sci. USA*, 74:5463–5467] using Sequenase® or Taq Trak® kits as directed by the manufacturer. Templates were prepared from the cDNAs by constructing a series of nested deletions [Henikoff, *Gene*, 28:351–359 (1984)] in the vector, pBluescript SK(−) (Stratagene) using exonuclease III and mung bean nuclease according to the manufacturer's protocol. In cases where overlapping templates were not attained by this method, the cDNAs were cleaved at convenient restriction endonuclease sites and subcloned into pBluescript, or specific oligomers were manufactured to prime the template for sequencing. Single-stranded DNA templates were rescued by isolating the DNA from phagemid secreted by helper phage-infected XL1 cells harboring the pBluescript plasmid [Levinson et al., supra] as recommended by the manufacturer (Stratagene). Homology searches of GEN-BANK (Release 66.0), EMBL (Release 25.0), and NBRF nucleic acid (Release 36.0) and protein (Release 26.0) databases were conducted using Wordsearch, FASTA and TFASTA programs supplied with the Genetics Computer Group software package Devereux et al., *Nuc. Acids Res.*, 12:387–395 (1984).

The nucleotide sequence and deduced amino acid sequence encoded by the large open reading frame of p3CGS-5 cDNA clone insert is provided in SEQ ID NO: 38 and SEQ ID NO: 39. Starting with the first methionine codon, the cDNA encodes a 921 residue polypeptide with a calculated molecular weight of about 103,000. Although no stop codons precede this sequence, an initiator methionine consensus sequence [Kozak, *J. Cell Biol.*, 108:229–241 (1989)] has been identified. The presence of 36 adenosine residues at the 3' end of the cDNA preceded by a transcription termination consensus sequence [Birnstiel et al., *Cell*, 41:349–359 (1985)] suggests that all of the 3' untranslated sequence of the cGS-PDE mRNA is represented by this clone.

A putative phosphodiesterase-deficient (PPD) strain of S49 cells [Bourne et al., *J. Cell. Physiol.*, 85:611–620 (1975)] was transiently transfected with the cGS-PDE cDNA using the DEAE-dextran method. The cGS-PDE cDNA was ligated into the unique BamHI cloning site in a mammalian expression vector, designated pZEM 228, following a zinc-inducible metallothionine promoter and prior to an SV40 transcription termination sequence. The DNA was purified from large-scale plasmid preparations using Qiagen pack-500 columns as directed by the manufacturer. PPD-S49 cells were cultured in DMEM containing 10% heat-inactivated horse serum, 50 µg/ml penicillin G and 50 µg/ml streptomycin sulfate at 37° C. in a water-saturated 7% $CO_2$ atmosphere. Prior to transfections, confluent 100 mm dishes of cells were replated at one-fifth of the original density and incubated for 24–36 h. In a typical transfection experiment, PPD-S49 cells (50–80% confluent) were washed with Tris-buffered-saline and approximately 2×$10^7$ cells were transfected with 10 µg of DNA mixed with 400 µg of DEAE-dextran in one ml of TBS. The cells were incubated at 37° C. for 1 hr with gentle agitation every 20 min. Next, DMSO was added to a final concentration of 10% and rapidly mixed by pipetting up and down. After 2 min, the cells were diluted with 15 volumes of TBS, collected by centrifugation, and washed, consecutively with TBS and DMEM. The cells were resuspended in complete medium and seeded into fresh 100 mm plates (1–2×107 cells/10 ml/plate). After 24 h, the cells were treated with TBS alone, or containing zinc sulfate (final concentration=125 µM) and incubated for an additional 24 h. The cells were harvested and washed once with TBS. The final cell pellets were resuspended in two mls of homogenization buffer (40 mM Tris-HCl; pH 7.5, 15 mM benzamidine, 15 mM β-mercaptoethanol, 0.7 µg/ml pepstatin A, 0.5 µg/ml leupeptin and 5 mM EDTA) and disrupted on ice using a dounce homogenizer. The homogenates were centrifuged at 10,000×g for 5 min at 4° C. and the supernatants were assayed for phosphodiesterase activity and protein concentration.

cGS PDE activity was determined by a previously described method using [$^3$H]cAMP as the substrate as in Martins et al., *J. Biol. Chem.*, 257:1973–1979 (1982). Phosphodiesterase assays were performed in triplicate. The Bradford assay [Bradford, *Anal. Biochem.*, 72:248–254 (1976)] was used to quantitate protein using BSA as the standard.

In the absence of zinc treatment, no increase in basal activity or cGMP-stimulated phosphodiesterase activity was detected in PPD S49 cells transfected with the cGS PDE-ZEM 228 construct or the vector alone. However, zinc-treated cells transfected with cGS-PDE cDNA, but not the vector alone, expressed cGMP-enhanced cAMP phosphodiesterase activity indicating that the cDNA encodes a cGS-PDE. The total activity of the homogenates and 50,000×g supernatants was not significantly different.

Transient expression of the cGS-PDE cDNA in COS-7 cells was accomplished as in Example I. A 4.2 kb fragment of p3CGS-5 was isolated using HindIII and NotI and was inserted into plasmid pCDM8, which had been digested with the same enzymes. The character of products produced in COS-7 cells transformed with the p3CGS-5/pCDM8 construct is discussed in Example V, infra.

EXAMPLE V

Isolation, Purification, and Partial Sequence Determination of cGS-PDE cDNA from Bovine Brain A. Isolation of Bovine Brain cGSPDE cDNA Clone, pBBCGSPDE-5

A bovine brain cDNA library constructed with the γ ZAP vector (kindly provided by Ronald E. Diehl, Merck, Sharp & Dohme) was screened with a 450 bp EcoRI/ApaI restriction endonuclease cleavage fragment of the p3CGS-5 cDNA corresponding to (p3CGS-5) nucleotide position numbers 1–452. The probe was prepared using the method of Feinberg et al., supra, and the [$^{32}$P]-labeled DNA was purified using Elutip D® columns. Plaques (a total of 600,000 plaques on 12-150 mm plates) bound to filter circles were hybridized at 42° overnight in a solution containing 50% formamide, 20 mM Tris HCl (pH 7.5), 1× Denhardt's solution, 10% dextran sulfate, 0.1% SDS and 10$^6$ cpm/ml [$^{32}$P]-labeled probe (10$^9$ cpm/µg). The filters were washed three times for 15 minutes with 2× SSC/0.1% at room temperature, followed by two 15 minute washes with 0.1× SSC/0.1% SDS at 45°. The filters were exposed to x-ray film overnight.

Forty putative clones were picked from this first screen, of which six were randomly selected and purified by several rounds of re-plating and screening [Maniatis et al., supra]. The insert cDNAs were subcloned into pBluescript SK(–) by in vivo excision as recommended by the manufacturer. Plasmid DNA prepared from cultures of each clone was sequenced from the ends using Sequenase and Taq Trak sequencing kits. The sequence obtained from this experiment confirmed that the bovine brain cDNA clone, pBBCGSPDE-5 was a cGS-PDE cDNA, and that it was different than the adrenal cGS-PDE cDNA at the five-prime end.

Partial sequence analysis of the pBBCGSPDE-5 insert at its 5' end (encoding the amino terminal region of the protein) revealed the sense strand set out in SEQ ID NO: 40, while sequencing of the 3' end of the insert revealed the antisense sequence of SEQ ID NO: 41.

B. Isolation of Bovine Brain cGS-PDE cDNA Clone, pBBCGSPDE-7

Each of the forty putative clones selected from the first round of purification described above was spotted individually onto a lawn of host XL1 cells and incubated overnight at 37°. The plaques were screened with a 370 bp PstI/SmaI restriction endonuclease cleavage fragment of the p3CGS-5 cDNA (corresponding p3CGS-5 nucleotide position numbers 2661–3034). The probe was prepared using the method of Feinberg et al., supra, and the [$^{32}$P]-labeled DNA was purified using Elutip-D® columns. Plaques bound to filter circles were hybridized at 42° overnight in a solution containing 50% formamide, 20 mM Tris-HCl (pH 7.5), 1× Denhardt's solution, 10% dextran sulfate, 0.1% SDS and 10$^6$ cpm/ml [$^{32}$P]-labeled probe (10$^9$ cpm/µg). The filters were washed three times for 15 minutes with 2× SSC/0.1% SDS at room temperature, followed by two 15-minute washes with 0.1× SSC/0.1% SDS at 45°. The filters were exposed to x-ray film overnight.

After several rounds of plating and rescreening, six putative clones were purified and sequenced from the ends. The sequence of the five-prime end of the cDNA clone pBBCGSPDE-7 was identical to clone pBBCGSPDE-5, but not the adrenal gland-derived clone, p3CGS-5. The sequence of the three-prime end of the pBBCGSPDE-7 cDNA clone was identical to the p3CGS-5 insert sequence.

Sequence analysis of the pBBCGSPDE-7 insert revealed the DNA sequence set out in SEQ ID NO: 42 and the amino acid sequence of SEQ. ID NO: 43.

The large open reading frame encodes a 942-residue polypeptide that is nearly identical to the adrenal gland cGS-PDE isozyme (921 residues). The difference in the primary structure of these two isozymes lies in the amino-terminal residues 1–46 of the brain cGS-PDE, and residues 1–25 of the adrenal cGS-PDE. The remaining carboxy-terminal residues of the brain and adrenal cGS-PDE are identical.

For transient expression in COS-7 cells, a 3.8 kb fragment of pBBCGSPDE-7 was isolated using HindIII and NotI and inserted into plasmid pCDM8 which had been cut with HindIII and NotI restriction endonucleases. The recombinant pBBCGSPDE-7/CDM8 construct was used to transiently transfect COS-7 cells. The properties of the pBBCGSPDE-7/CDM8 construct and the p3CGS-5/CDM8 construct prepared in Example IV products were subsequently compared. Membrane and supernatant fractions were prepared from extracts of transfected COS-7 cells and assayed for cGS-PDE activity. Both the pBBCGSPDE-7/CDM8 and p3CGS5/CDM8 plasmid constructs produced cGS-PDE activities in COS-7 cell extracts, and most of the activity was detected in the supernatant fractions. However, a 10-fold greater percentage of total cGS-PDE activity was detected in membranes from COS-7 cell extracts transfected with the pBBCGSPDE-7/CDM8 construct than in membranes prepared from p3CGS-5/CDM8-transfected COS-7 cells. These results indicate that, relative to the adrenal cGS-PDE, the isozyme encoded by the pBBCGSPDE-7 cDNA preferentially associates with cellular membranes.

EXAMPLE VI

Use of cGS-PDE Bovine Adrenal cDNA to Obtain Human cGS-PDE cDNAs

Several human cDNA clones, homologous to a cDNA clone encoding the bovine cyclic GMP-stimulated phosphodiesterase, were isolated by hybridization using a nucleic acid probe derived from the bovine cDNA. A combination of sequence analysis and hybridization studies indicates that these human cDNA clones encompass an open reading frame corresponding to a human phosphodiesterase.

cDNA libraries were probed with DNA from plasmid p3CGS-5 which contains a 4.2-kb cDNA insert encoding the bovine cGS-PDE. This plasmid was digested with the restriction enzymes SmaI and EcoRI. The approximately 3.0 kb fragment derived from the cDNA insert was isolated and purified by agarose gel electrophoresis. This fragment contains the entire open reading-frame of the PDE. The fragment was labeled with radioactive nucleotides by random priming.

The cDNA libraries were plated on a 150 mm petri dishes at a density of approximately 50,000 plaques per plate. Duplicate nitrocellulose filter replicas were prepared. The radioactive nucleic acid probe was used for hybridization to the filters overnight at 42° C. in 50% formamide, 5× SSPE (0.9M NaCl, 0.05M $NaH_2PO_4$ $H_2O$, 0.04M NaOH, and 0.005M $Na_2EDTA_2H_2O$), 0.5% SDS, 100 μg/ml salmon testes DNA, and 5× Denhardt's solution. The filters were washed initially at room temperature and subsequently at 65° C. in 2× SSC containing 0.1% SDS. Positive plaques were purified and their inserts were subcloned into an appropriate sequencing vector for DNA sequence analysis by standard techniques.

First, a λgt10 cDNA library prepared from human hippocampus mRNA (clontech, random and dT primed) was screened. Of the approximately 500,000 plaques examined, 33 hybridized to the probe. One of these phages was digested with EcoRI to remove the cDNA insert. This insert-containing EcoRI fragment was cloned into Bluescript KS that had been digested with EcoRI and then treated with calf intestine alkaline phosphatase. One product of this reaction was the plasmid pGSPDE9.2, which showed two major differences when compared to the bovine cGS-PDE cDNA. The 5'0.4 kb of the pGSPDE9.2 insert diverged from the bovine cDNA. Approximately 0.7 kb from the 5' end of the human cDNA there is a 0.7 kb region that diverges from the bovine cDNA. This region may be an intron. Twenty-five of the remaining hippocampus plaques that had hybridized to the bovine probe were examined by PCR, hybridization and/or sequencing. None were found to extend through the regions that differed between the bovine and human cDNAs.

Phages λ GSPDE7.1 and λ GSPDE7.4, two other phages from the hippocampus library, were digested with EcoRI and HindIII. Each yielded a 1.8-kb fragment that contains most of the cDNA insert and approximately 0.2-kb of phage lambda DNA. The λ DNA is present in the fragment because in each case one of the EcoRI sites that typically bracket a cDNA insert had been destroyed, possibly when the library was constructed. The EcoRI/HindIII fragments were cloned into Bluescript KS digested with EcoRI and HindIII. This procedure gave rise to the plasmids pGSPDE7.1 and pGSPDE7.4. The cDNA inserts encode DNA homologous to the 3' portion of the bovine phosphodiesterase cDNA. Both of the cDNA inserts in these clones begin at an EcoRI site and the sequences are homologous adjacent this site.

Portions of pGSPDE7.1 and pGSPDE7.4 cDNA inserts were sequenced and are identical except for a short region of their 3' ends. The cDNA insert in pGSPDE7.1 ends with a sequence of approximately 70 adenine bases, while the cDNA insert in pGSPDE7.4 ends with three additional nucleotides not present in pGSPDE7.1 followed by a sequence of approximately 20 adenine bases.

Next, a cDNA library prepared in λ ZapII (Stratagene) from human heart mRNA yielded one hybridizing plaque from the approximately 500,000 screened. The Bluescript SK(−) plasmid pGSPDE6.1 containing the hybridizing insert was excised in vivo from the λ ZapII clone. Sequence analysis showed that the insert is homologous to the bovine phosphodiesterase cDNA. The homologous region spans the position of the EcoRI found in the sequence formed by joining the sequence of the insert from pGSPDE9.2 to the sequence of the insert in pGSPDE7.1 or pGSPDE7.4. Thus, it is thought that the two clones from the hippocampus form a complete open reading frame.

A third λ gt10 library derived from human placenta mRNA yielded five hybridizing plaques from approximately 800,000 screened. These placental cDNA clones were short and their sequences were identical to portions of the hippocampus cDNA pGSPDE9.2. Screening $5 \times 10^5$ plaques from U118 glioblastoma cDNA library, $5 \times 10^5$ from a spleen cDNA library and $5 \times 10^5$ from an adrenal library (Cushings Disease) gave no hybridization plaques.

Given the homology between the bulk of human and bovine cGS-PDE sequence, it was decided to obtain multiple independent cDNA clones containing the 5' end of the human cGS-PDE to determine if the 0.4 kb 5' sequence was an artifact. An approximately 0.95 kb EcoRI-HindII fragment from the 5' end of the bovine cGS cDNA plasmid p3cgs5 was random primed and used as a probe to screen a number of human cDNA libraries. Hippocampus library screening was carried out under the same screening conditions as described above. All remaining screenings were carried out as described with respect to human heart cDNA library screenings in Example VII, infra. No positives were obtained screening $5 \times 10^5$ plaques from a human T cell library (Hut78, dT-primed), $10^6$ plaques from the hippocampus cDNA library (random and dT-primed), $5 \times 10^5$ plaques from a human liver cDNA library (dT-primed, 5' stretch, Clontech), $5 \times 10^5$ plaques from a human SW1088 glioblastoma cDNA library (dT-primed), $5 \times 10^5$ plaques from the same heart cDNA library (random and dT-primed), and $1.5 \times 10^6$ plaques from a human lung cDNA library (random primed). Two positives were obtained from screening $5 \times 10^5$ plaques from a human fetal brain cDNA library (random and dT-primed, Stratagene). These were designated as HFB9.1 and HFB9.2.

Bluescript SK(−) plasmids pHFB9.2 and pHFB9.1 were excised in vivo from the λZapII clones. DNA sequence analysis revealed that HFB9.1 starts about 80 nucleotides further 3' than does HFB9.2 and reads into an intron approximately 1.9 kb of the way into HFB9.2. HFB9.2 covers the entire open reading frame of the cGS-PDE, but reads into what may be an intron 59 nucleotides after the stop codon. Both of them lack the 5'0.4 kb and the presumed intron found in pGSPDE9.2. The entire open reading frame of HFB9.2 was isolated and assembled into yeast expression vector pBNY6N. The resulting plasmid, designated pHcgs6n, includes the coding region of the cDNA as an EcoRI/XhoI insert. DNA and deduced amino acid sequences for the insert are provided in SEQ. ID No: 44 and 45, respectively.

EXAMPLE VII

Use of CaM-PDE 61 kDa Bovine Brain cDNA to Obtain Human CaM-PDE 61 kDa cDNA

Human cDNA clones, λ CaM H6a and λ CaM H3a, which are homologous to the cDNA encoding the bovine 61 kDa CaM-PDE, were obtained by hybridization using a nucleic acid probe derived from the cDNA encoding the bovine species enzyme. A combination of sequence analysis and hybridization studies indicate that λ Cam H6a contains most of an open reading frame encoding a human CaM-PDE.

The hybridization probe used to isolate the human DNA was derived from first strand cDNA of bovine lung tissue by PCR treatment. More specifically, the 23-mer oligonucleotide designated PCR-2S in Example I (see, SEQ ID NO: 1) was combined in a PCR reaction with bovine lung cDNA and a redundant antisense 23-mer oligonucleotide (PCR-5AS) based on the pCAM insert sequence with

SEQ ID NO: 46
5'TCRTTNGTNGTNCCYTTCATRTT-3' representing the amino acid sequence

SEQ ID NO: 47
NMKGTTND, according to the general procedures of Examples I and III, to generate a 1098 bp cDNA fragment representing a large portion of the coding region of the pCAM-40 insert. The PCR products were purified on a 1% agarose gel using 0.4M Tris-acetate/0.001M EDTA buffer containing 0.5 μg/ml ethidium bromide. The DNA products were visualized with UV light, cleanly excised from the gel with a razor blade, purified using Geneclean II reagent kit and ligated into EcoRV-cut pBluescript vector DNA.

To determine if the PCR amplification products were CAM-PDE cDNAs, the subcloned PCR DNA products were sequenced from the ends using T3 and T7 promoter primers and either Sequenase or Taq Polymerase sequencing kits. Approximately 250 bases from each end of this DNA were then compared to the amino acid sequence of bovine CAM-PDE, confirming that the PCR DNA product was a partial CAM PDE cDNA. This clone was designated pCAM-1000 and contained a 1.1-kb insert of nucleic acid that corresponds to nucleotides 409 to 1505 of the insert of pCAM-40. pCaM1000 was digested with the restriction enzymes HinDIII and BamHI. The 1.1-kb fragment was purified by agarose gel electrophoresis and then digested with the restriction enzyme AccI. The two fragments were separated and purified by agarose gel electrophoresis. These separated fragments were labeled with radioactive nucleotides by random priming.

Human cDNA libraries were plated on 150 mm petri dishes at a density of approximately 50,000 plaques per dish and duplicate nitrocellulose filter replicas were prepared. Each probe was hybridized to a separate set of the duplicate filters. The filters were hybridized overnight at 65° C. in 3x SSC, 0.1% sarkosyl, 50 μg/ml salmon testes DNA, 10x Denhardt's solution, 20 mM sodium phosphate (pH 6.8). They were washed at 65° C. in 2x SSC containing 0.1% SDS.

A λ gt10 library prepared from human hippocampus mRNA yielded three hybridizing plaques of the approximately 500,000 screened. Of these three hybridizing plaques, two hybridized to both probes and the third hybridized to the longer of the two probes. The λ Cam H6a clone contains an approximately 2 kb insert that is homologous to the cDNA encoding the bovine clone of pCAM-40.

The λ cam H6a cDNA was subcloned into the plasmid Bluescript KS for sequence analysis. Although the cDNA library had been constructed with EcoRI linkers, one of the EcoRI sites that should have flanked the cDNA insert did not cut with EcoRI. Thus, the cDNA was subcloned as two fragments: an approximately 0.7 kb EcoRI/HindIII fragment (pcamH6C) and an approximately 1.6 kb HindIII fragment that contained approximately 1.3 kb of cDNA and 0.25 kb of flanking λgt10 vector DNA (pcamH6B). DNA sequence analysis revealed that it encoded most of a human CaM-PDE homologous to the bovine 61 k CaM-PDE, except that the human cDNA appeared to be missing two base pairs in the middle of the coding region. These missing nucleotides correspond to positions 626 and 627 of the human cDNA sequence if it is aligned with the pCAM-40 bovine 61 kDa CaM-PDE (SEQ. ID NO: 5 for maximum homology.

Another of the cDNA clones from the hippocampus cDNA library that had been screened with the bovine 61 kDa CaM-PDE probes was λcamH2a. It contained an approximately 1.0 kb insert. As was the case for λcamH6a cDNA, only one of the two EcoRI sites that should be present at the ends of the insert would cut. The original subcloning and DNA sequence analysis for this cDNA utilized PCR fragments generated with oligos in the flanking λgt10 vector arms. This cDNA overlaps much of the 5' end of the insert in λcamH6a and contained the additional two nucleotides predicted by the bovine sequence and required to maintain the PDE open reading frame. The λcamH2a insert also appeared to contain two introns; one 5' of the initiator methionine and one downstream of the HindIII site. The EcoRI/HindIII fragment from λcamH2a (corresponding to the region covered by pcamH6C) was subcloned into the plasmid Bluescript SK⁻ and designated pcamH2A-16. This was then used as the source of the two additional bp in the construction of yeast expression plasmids described below.

Two different plasmids were constructed for human CaM-PDE expression in yeast. One plasmid, pHcam61-6N-7, contains the entire open reading frame. The second plasmid, pHcam61met140, starts at an internal methionine (beginning at nucleotide position 505) and extends to the end of the open reading frame. These expression plasmids were constructed by modifying the 3' portion of the open reading frame and then adding the two differently modified 5' ends to the 3' end. The sequence of the cDNA insert of pHcam61-6N-7 is set out in SEQ. ID NO: 48 and the deduced amino acid sequence of the CaM-PDE encoded thereby is set out in SEQ. ID NO: 49. During construction of the cDNA insert, the nucleotide at position 826 was altered from T to C, but the encoded amino acid was conserved. Plasmid pHcam61met140, as noted above, has a cDNA insert lacking the first 140 codons of the coding region of the pHcam61-6N-7 but is otherwise identical thereto.

A third cDNA, λcamH3a, contained an approximately 2.7 kb insert. This cDNA insert was subcloned for sequence analysis. Although the cDNA library had been constructed with EcoRI, the inserted cDNA in λcamH3a could not be excised with EcoRI. Presumably one of the EcoRI sites was destroyed during the construction of the library. The cDNA insert was excised from the λ clone by digestion with HindIII and EcoRI. This digestion yields two relevant fragments, a 0.6 kb HindIII fragment which contains a portion of DNA from the left arm of λgt10 attached to the cDNA insert and an approximately 2.4 kb HindIII/EcoRI fragment containing the remainder of the cDNA insert. These two fragments were assembled in the plasmid Bluescript KS to yield an approximately 3 kb fragment. The orientation of the small HindIII fragment was the same as the original λ clone. This subclone is known as pcamH3EF. Although this cDNA hybridizes to the bovine probe from the bovine CaM-PDE 61 kDa cDNA, sequence analysis revealed that it appeared to be the product of a different CaM-PDE gene. Plasmid pcamH3EF contains what may be the entire open reading frame and would encode a protein approximately 75% homologous to the protein encoded by the insert of pHcam61-6N-7 over much of its lengths. DNA and deduced amino acid sequences are set out in SEQ. ID NOS: 50 and 51, respectively. The DNA sequence of the region between nucleotide 80 and 100 of pcamH3EF is uncertain. This area is 5' to the initiator methionine codon and thus does not effect the open reading frame.

An approximately 2.4 kb fragment of pcamH3EF was gel purified following digestion with the restriction enzymes HindIII and EcoRI. This fragment was used to screen additional human cDNA libraries in a similar manner to the screen described above. Screening approximately $5 \times 10^5$ plaques from a human heart cDNA library (Stratagene) yielded two plaques that hybridized to the pcamH3EF probe. The Bluescript SK⁻ plasmid pcamHella was excised in vivo from one of these positive λZapII clones. DNA and deduced amino acid sequences for the cDNA insert are set out in SEQ. ID NO: 52 and 53, respectively. Sequence analysis of pcamHella showed that the insert began at nucleotide position 610 of pcamH3EF and was nearly identical through nucleotide position 2066, at which point the DNA sequence diverged from that of pcamH3EF. The cDNA insert of pcamHella continued for approximately 0.6 kb. The consequence of this divergence is to alter the carboxy terminus of the protein that would be encoded by the open reading frame within the cDNA. The pcamH3EF cDNA could encode a protein of 634 amino acids (MW72,207). Assuming the 5' end of the pcamHella cDNA is the same as that of the 5' end of pcamH3EF (5' to nucleotide position 610), pcamHella could encode a 709 amino acid protein (MW80,759). These divergent 3' ends may be the consequence of alternative splicing, lack of splicing, or unrelated DNA sequences being juxtaposed during the cloning process.

EXAMPLE VIII

Expression of Bovine and Human PDE cDNAs for Complementation of Yeast Phenotypic Defects The present example relates to the expression of bovine and PDE clones in yeast demonstrating the capacity of functional PDE expression products to suppress the heat shock phenotype associated with mutation of yeast phosphodiesterase genes and also relates to the biochemical assay of expression products. The host cells used in these procedures were S. cerevisiae yeast strains 10DAB (ATCC accession No. 74049) and YKS45, both of which were pde$^{1-}$ pde$^{2-}$ resulting in a phenotype characterized by heat shock sensitivity, i.e., the inability of cells to survive exposure to elevated temperatures on the order of 55°–56° C. In these complementation procedures, the inserted gene product was noted to conspicuously modify the heat shock phenotype. This capacity, in turn, demonstrates the feasibility of systems designed to assay chemical compounds for their ability to modify (and especially the ability to inhibit) the in vivo enzymatic activity of mammalian Ca$^{2+}$/calmodulin stimulated and cGMP stimulated cyclic nucleotide phosphodiesterases.

A. Yeast Phenotype Complementation by Expression of a cDNA Encoding CaM-PDE

A 2.2 kb cDNA fragment, adapted for insertion into yeast expression plasmids pADNS (ATCC accession No. 68588) and pADANS (ATCC accession No. 68587) was derived from plasmid pCAM-40 (Example I) by polymerase chain reaction. Briefly, the following PCR amplification was employed to alter the pCAM-40 DNA insert to align it appropriately with the ADH1 promoter in the vectors.

One oligonucleotide primer (Oligo A) used in the PCR reaction

SEQ ID NO: 54
  5'-TACGAAGCTTTGATGGGGTCTACTGCTAC-3' anneals to the pCAM-40 cDNA clone at base pair positions 100–116 and includes a HindIII site before the initial methionine codon. A second oligonucleotide primer (Oligo B)

SEQ ID NO: 55
  5'-TACGAAGCTTTGATGGTTGGCTTGGCATATC-3' was designed to anneal at positions 520–538 and also includes a HindIII site two bases before a methionine codon. The third oligonucleotide

SEQ ID NO: 56
  5'-ATTACCCCTCATAAAG-3' annealed to a position in the plasmid that was 3' of the insert. For one reaction, Oligo A and Oligo C were used as primers with pCAM-40 as the template. The nucleic acid product of this reaction included the entire open reading frame. A second reaction used Oligo B and Oligo C as primers on the template pCAM-40 and yielded a nucleic acid product that lacked the portion of the cDNA sequence encoding the calmodulin binding domain. These amplified products were digested with HindIII and NotI and ligated to HindIII/NotI-digested yeast expression vectors pADNS and pADANS. Plasmid clones containing inserts were selected and transformed into S. cerevisiae strain 10DAB by lithium acetate transformation.

Transformed yeast were streaked in patches on agar plates containing synthetic medium lacking the amino acid leucine (SC-leucine agar) and grown for 3 days at 30° C. Replicas of this agar plate were made with three types of agar plates: one replica on SC-leucine agar, one replica on room temperature YPD agar, and three replicas on YPD agar plates that had been warmed to 56° C. The three warmed plates were maintained at 56° C. for 10, 20, or 30 minutes. These replicas were than allowed to cool to room temperature and then all of the plates were placed at 30° C. Yeast transformed with plasmids constructed to express the CaM-PDE were resistant to the thermal pulse. More specifically, both the construct designed to express the complete open reading frame and that designed to express the truncated protein (including the catalytic region but not the calmodulin binding domain), in either pADNS or pADANS, complemented the heat shock sensitivity phenotype of the 10DAB host cells, i.e., rendered them resistant to the 56° C. temperature pulse.

In a like manner, plasmids pHcam61-6N-7 and pHcam61met140 (Example VII) were transformed into yeast host 10DAB. Heat shock phenotypes were suppressed in both transformants.

B. Biochemical Assay of Expression Products

The bovine CaM-PDE expression product was also evaluated by preparing cell-free extracts from the 10DAB yeast cells and measuring the extracts' biochemical phosphodiesterase activity. For this purpose, 200 ml cultures of transformed yeast were grown in liquid SC-leucine to a density of about 6 million cells per ml. The cells were collected by centrifugation and the cell pellets were frozen. Extracts were prepared by thawing the frozen cells on ice, mixing the cells with 1 ml of PBS and an equal volume of glass beads, vortexing them to disrupt the yeast cells, and centrifuging the disrupted cells at approximately 12,000×g for 5 min to remove insoluble debris. The supernatant was assayed for phosphodiesterase activity.

Extracts of yeast cells, up to 50 μl, were assayed for phosphodiesterase activity in 50 mM Tris (pH 8.0), 1.0 mM EGTA, 0.01 mg/mL BSA (bovine serum albumin), [$^3$H]-cyclic nucleotide (4–10,000 cpm/pmol), and 5 mM $MgCl_2$ in a final volume of 250 μl at 30° C. in 10×75 mm glass test tubes. The incubations were terminated by adding 250 μl of 0.5M sodium carbonate pH 9.3, 1M NaCl, and 0.1% SDS. The products of the phosphodiesterase reaction were separated from the cyclic nucleotide by chromatography on 8×33 mm columns of BioRad Affi-Gel 601 boronic acid gel. The columns were equilibrated with 0.25M sodium bicarbonate (pH 9.3) and 0.5M NaCl. The reactions were applied to the columns. The assay tubes were rinsed with 0.25M sodium bicarbonate (pH 9.3) and 0.5M NaCl and this rinse was applied to the columns. The boronate columns were washed twice with 3.75 ml of 0.25M sodium bicarbonate (pH 9.3) and 0.5M NaCl followed by 0.5 ml of 50 mM sodium acetate (pH 4.5). The product was eluted with 2.5 ml of 50 mM sodium acetate (pH 4.5) containing 0.1M sorbitol and collected in scintillation vials. The eluate was mixed with 4.5 ml Ecolite Scintillation Cocktail and the radioactivity measured by liquid scintillation spectrometry.

Both the construct designed to express the complete bovine open reading frame and that designed to express a truncated protein, in either pADNS or pADANS, expressed active protein as determined by biochemical phosphodiesterase assay of cell extracts. Extracts of 10DAB harboring pcam61met140 yielded measurable phorphodiesterase activity (see, infra, second method of part D) while the extract of 10DAB cells harboring pcamH61-6N-7 lacked detectable activity.

C. Yeast Phenotype Complementation by Expression of a cDNA Encoding a cGS-PDE

The plasmid p3CGS-5, which contains a 4.2-kb DNA fragment encoding the bovine cGS-PDE, was adapted for cloning into pADNS and pADANS by replacing the first 147 bases of the cDNA with a restriction site suitable for use in insertion into plasmids. The oligonucleotide BS1, having the sequence

SEQ ID NO: 57
5'TACGAAGCTTTGATGCGCCGACAGCCTGC, encodes a HindIII site and anneals to positions 148–165 of the cDNA insert. An oligonucleotide designated BS3

SEQ ID NO: 58
GGTCTCCTGTTGCAGATATTG, anneals to positions 835–855 just 3' of a unique NsiI site. The resulting PCR-generated fragment following digestion with HindIII and NsiI was then ligated to HindIII- and NsiI-digested p3CGS-5 thereby replacing the original 5' end of the bovine cDNA. A plasmid derived from this ligation was digested with HindIII and NotI to release the modified cDNA insert. The insert was cloned into pADNS and pADANS at their HindIII and NotI sites. These plasmids were then transformed into the yeast strain 10DAB by the lithium acetate method and the transformed cells were grown and subjected to elevated temperatures as in Section A, above. Yeast transformed with plasmids constructed to express the bovine cGS-PDE were resistant to the thermal pulse.

In a like manner, plasmid pHcgs6n (Example VI) was transformed into yeast host strain YKS45 by lithium acetate transformation. Heat shock analysis was performed as above except that the plates were initially grown two days at 30° C. and the warmed plates were maintained at 56° C. for 10, 20, 30 and 45 minutes. Yeast transformed with the plasmid designed to express the full length human cGS-PDE was resistant to thermal pulse.

D. Biochemical Assay of Expression Product

The expression of the bovine cGS-PDE was also evaluated by preparing cell-free extracts from the yeast and measuring the extracts' biochemical phosphodiesterase activity. For this purpose, 50 ml cultures of transformed 10DAB yeast cells were grown in liquid SC-leucine to a density of about 10 million cells per ml. Sherman et al., *Methods in Yeast Genetics,* Cold Spring Harbor Laboratory, Cold Spring Harbor, N.Y. (1986). The cells were collected by centrifugation, the cell pellets were washed once with water, and the final cell pellets were frozen. To prepare an extract, the frozen cells were thawed on ice, mixed with 1 ml of PBS and an equal volume of glass beads, vortexed to disrupt the yeast cells, and centrifuged to remove debris. The supernatant was then assayed for phosphodiesterase activity as in Section B, above. Constructs in either pADNS or pADANS expressed active protein as determined by biochemical phosphodiesterase assay of cell extracts.

YKS45 transformed with plasmid pHcgs6n were grown in SC-leu medium to $1-2\times10^7$ cells/ml. The cells were harvested by centrifugation and the cell pellets were frozen. A frozen cell pellet, typically containing $10^{10}$ cells, was mixed with lysis buffer (25 mM Tris HCl pH 8, 5 mM EDTA, 5 mM EGTA, 1 mM o-phenathroline, 0.5 mM AEBSF, 0.01 mg/mL pepstatin, 0.01 mg/mL leupeptin, 0.01 mg/mL aprotinin, 0.1% 2-mercaptoethanol) to bring the total volume to 2.5 ml. The mixture was thawed on ice and then added to an equal volume of glass beads. The cells were disrupted by cycles of vortexing and chilling on ice, then additional lysis buffer was mixed with the disrupted cells to bring the total lysis buffer added to 5 ml. The suspension was centrifuged for 5 min. at 12,000×g. The supernatant was removed and either assayed immediately or frozen rapidly in a dry ice ethanol bath and stored at −70° C.

Phosphodiesterase activity was assayed by mixing an aliquot of cell extract in (40 mM Tris-Cl pH 8.0, 1. mM EGTA, 0.1 mg/mL BSA) containing 5 mM $MgCl_2$ and radioactive substrate, incubating at 30° C. for up to 30 min.

and terminating the reaction with stop buffer (0.1M ethanolamine pH 9.0, 0.5M ammonium sulfate, 10 mM EDTA, 0.05% SDS final concentration). The product was separated from the cyclic nucleotide substrate by chromatography on BioRad Affi-Gel 601. The sample was applied to a column containing approximately 0.25 ml of Affi-Gel 601 equilibrated in column buffer (0.1M ethanolamine pH 9.0 containing 0.5M ammonium sulfate). The column was washed five times with 0.5 ml of column buffer. The product was eluted with four 0.5 ml aliquots of 0.25M acetic acid and mixed with 5 ml Ecolume (ICN Biochemicals). The radioactive product was measured by scintillation counting. Extracts from yeast expressing the human cGS-PDE hydrolyzed both cyclic AMP and cyclic GMP, as expected for this isozyme.

EXAMPLE IX

Tissue Expression Studies Involving CaM-PDE and cGS-PDE Polynucleotides

A. Northern Blot Analysis

DNAs isolated in Examples I, III, and IV above were employed to develop probes for screening total or poly A-selected RNAs isolated from a variety of tissues and the results are summarized below.

1. Northern analysis was performed on mRNA prepared from a variety of bovine adrenal cortex, adrenal medulla, heart, aorta, cerebral cortex, basal ganglia, hippocampus, cerebellum, medulla/spinal cord, liver, kidney cortex, kidney medulla, kidney papillae, trachea, lung, spleen and T-lymphocyte tissues using an approximately 3 kb radiolabeled cDNA fragment isolated from plasmid p3CGS-5 upon digestion with EcoRI and SmaI. A single 4.5 kb mRNA species was detected in most tissues. The size of the cGS-PDE mRNA appeared to be slightly larger (approximately 4.6 kb) in RNA isolated from cerebral cortex, basal ganglia and hippocampus. The cGS PDE mRNA was most abundant in adrenal cortex. It was also abundant in adrenal medulla and heart. It appeared to be differentially expressed in anatomically distinct regions of the brain and kidney. Among RNAs isolated from five different brain regions, cGS PDE mRNA was most abundant in hippocampus, cerebral cortex, and basal ganglia. Very little cGS PDE transcript was detected in cerebellum or medulla and spinal cord RNAs. Although the cGS PDE mRNA was detected in all regions of the kidney, it appeared to be most abundant in the outer red medulla and papillae. The cGS PDE mRNA was also detected in liver, trachea, lung, spleen, and T-lymphocyte RNA. Very little cGS PDE mRNA was detected in RNA isolated from aorta.

2. Radiolabeled DNA probes were prepared from random hexamer primed fragments extended on heat denatured 1.6 kb EcoRI restriction endonuclease fragments of the cDNA insert of plasmid pCAM-40. In Northern analysis, the DNA probes hybridized with 3.8 and 4.4 kb mRNAs in brain and most of the other tissues analyzed including cerebral cortex, basal ganglia, hippocampus, cerebellum, medulla and spinal cord, heart, aorta, kidney medulla, kidney papillae, and lung. Hybridization of probe with the 3.8 kb mRNA from liver, kidney cortex and trachea were only detected after longer autoradiographic exposure.

3. Northern blot analysis of mRNA from several tissues of the central nervous system was carried out using a subcloned, labeled p12.3a DNA fragment (containing most of the conserved PDE catalytic domain) as a probe. The most intense hybridization signal was seen in mRNA from the basal ganglia and strong signals were also seen in mRNA from other tissues including kidney papilla and adrenal medulla.

B. RNAse Protection

1. Three antisense riboprobes were constructed. Probe III corresponds to the catalytic domain-encoding region of p3cGS-5 (273 bp corresponding to bases 2393 through 2666 of SEQ. ID NO: 38); probe II to the cGMP-binding domain encoding (468 bp corresponding to bases 959 through 1426; and probe I to the 5' end and portions of amino terminal-encoding region (457 bases corresponding to bases 1 through 457).

Total RNAs extracted from all of the examined tissues completely protected probes II and III. Nearly complete protection (457 bases) of riboprobe I with RNAs isolated from adrenal cortex, adrenal medulla, and liver was also observed. However, RNA isolated from cerebral cortex, basal ganglia, and hippocampus only protected an approximately 268-base fragment of riboprobe I. A relatively small amount of partially protected probe I identical in size with the major fragments observed in the brain RNA samples was also detected in RNAs isolated from all of the examined tissues except liver. Interestingly, heart RNA yielded both completely protected (457 base) riboprobe and, like brain RNA, a 268-base fragment. Unlike the protection pattern observed using RNAs isolated from any of the other tissues, however, the partially protected riboprobe I fragment appeared to be more abundant. The results suggest that two different cGS-PDE RNA species are expressed.

2. Radiolabeled antisense riboprobes corresponding to a portion of either the CaM-binding domain on the catalytic domain of CaM-PDE were constructed from restriction endonuclease cleavage fragments (AccI/SstI and Tth111I/HincII) of pCAM-40cDNA. Total RNAs isolated from five different brain regions (cerebral cortex, basal ganglia, hippocampus, cerebellum, and medulla/spinal cord) completely protected the antisense riboprobes encoding both the CaM-binding and catalytic domains. Total RNAs from heart, aorta, lung, trachea and kidney completely protected the riboprobe corresponding to the catalytic domain but only protected about 150 bases of the CaM-binding domain riboprobe, suggesting that an isoform structurally related to the 61 kD CaM-PDE is expressed in these tissues.

3. Antisense riboprobes were generated based on plasmid p12.3a and corresponding to bases −1 through 363 and 883–1278 of SEQ. ID NO: 26. The former probe included 113 bases of the 5' noncoding sequence as well as the start methionine codon through the putative CaM-binding domain, while the latter encoded the catalytic domain. Among all tissues assayed, RNA from basal ganglia most strongly protected each probe. Strong signals of a size corresponding to the probe representing the amino terminus were observed in protection by cerebral cortex, cerebellum, basal ganglia, hippocampus and adrenal medulla RNA. No protection was afforded to this probe by kidney papilla or testis RNA even though the tissue showed signals on the Northern analysis and RNAse protection of the conserved domain probe, suggesting that a structurally related isozyme is expressed in this tissue.

While the present invention has been described in terms of specific methods and compositions, it is understood that variations and modifications will occur to those skilled in the art upon consideration of the invention. Consequently only such limitations as appear in the appended claims should be placed thereon. Accordingly, it is intended in the appended claims to cover all such equivalent variations which come within the scope of the invention as claimed.

What is claimed is:

1. A purified and isolated polynucleotide comprising the DNA sequence encoding a mammalian $Ca^{2+}$/calmodulin stimulated cyclic nucleotide phosphodiesterase enzyme set out in SEQ ID NO: 5.

2. A purified and isolated polynucleotide comprising the DNA sequence encoding a mammalian $Ca^{2+}$/calmodulin stimulated cyclic nucleotide phosphodiesterase enzyme set out in SEQ ID NO: 16.

3. A purified and isolated polynucleotide comprising the DNA sequence encoding a mammalian $Ca^{2+}$/calmodulin stimulated cyclic nucleotide phosphodiesterase enzyme set out in SEQ ID NO: 26.

4. A purified and isolated polynucleotide comprising the DNA sequence encoding a mammalian $Ca^{2+}$/calmodulin stimulated cyclic nucleotide phosphodiesterase enzyme set out in SEQ ID NO: 48.

5. A purified and isolated polynucleotide comprising the DNA sequence encoding a mammalian $Ca^{2+}$/calmodulin stimulated cyclic nucleotide phosphodiesterase enzyme set out in SEQ ID NO: 50.

6. A purified and isolated polynucleotide comprising the DNA sequence encoding a mammalian $Ca^{2+}$/calmodulin stimulated cyclic nucleotide phosphodiesterase enzyme set out in SEQ ID NO: 52.

7. A DNA vector having inserted therein a polynucleotide sequence according to claims 1, 2, 3, 4, 5, or 6.

8. The DNA vector of claim 7 designated pCaM-40 (A.T.C.C. 68576).

9. The DNA vector of claim 7 designated p12.3A (A.T.C.C. 68577).

10. The DNA vector of claim 7 designated pcamHella (A.T.C.C. 68965).

11. The DNA vector of claim 7 designated pcamH3EF (A.T.C.C. 68964).

12. The DNA vector of claim 7 designated λ CaM H6a. (A.T.C.C. 75000).

13. The DNA vector of claim 7 designated pHcam61-6N-7 (A.T.C.C. 68963).

14. A cDNA sequence according to claim 1, 2, 3, 4, 5, or 6.

15. A genomic DNA sequence according to claim 1, 2, 3, 4, 5, or 6.

16. A procaryotic or eucaryotic host cell stably transformed with a polynucleotide sequence according to claim 1, 2, 3, 4, 5, or 6.

17. A yeast host cell according to claim 16.

18. A method for producing a polypeptide having the enzymatic activity of a mammalian $Ca^{2+}$/calmodulin stimulated cyclic nucleotide phosphodiesterase enzyme, said method comprising:

(a) stably transforming or transfecting a procaryotic or eucaryotic host cell with a polynucleotide sequence according to claim 1, 2, 3, 4, 5, or 6; and (b) growing the host cell formed in step (a) in a nutrient medium under conditions allowing expression of said polynucleotide in said host cell.

19. A method according to claim 18 further including the step of isolating the polypeptide product of expression of said polynucleotide sequence in said host cell.

20. A method according to claim 17 wherein said host cell is a yeast host cell.

21. A purified and isolated polynucleotide encoding a polypeptide having the enzymatic activity of mammalian $Ca^{2+}$/calmodulin stimulated cyclic nucleotide phosphodiesterase enzyme wherein said polynucleotide hybridizes under stringent conditions to the complementary strand of the DNA set forth in SEQ ID NO: 16.

22. A purified and isolated polynucleotide encoding a polypeptide having the enzymatic activity of mammalian $Ca^{2+}$/calmodulin stimulated cyclic nucleotide phosphodiesterase enzyme wherein said polynucleotide hybridizes under stringent conditions to the complementary strand of the DNA set forth in SEQ ID NO: 26.

23. A purified and isolated polynucleotide encoding a polypeptide having the enzymatic activity of mammalian $Ca^{2+}$/calmodulin stimulated cyclic nucleotide phosphodiesterase enzyme wherein said polynucleotide hybridizes under stringent conditions to the complementary strand of the DNA set forth in SEQ ID NO: 48.

24. A purified and isolated polynucleotide encoding a polypeptide having the enzymatic activity of mammalian $Ca^{2+}$/calmodulin stimulated cyclic nucleotide phosphodiesterase enzyme wherein said polynucleotide hybridizes under stringent conditions to the complementary strand of the DNA set forth in SEQ ID NO: 50.

25. A purified and isolated polynucleotide encoding a polypeptide having the enzymatic activity of mammalian $Ca^{2+}$/calmodulin stimulated cyclic nucleotide phosphodiesterase enzyme wherein said polynucleotide hybridizes under stringent conditions to the complementary strand of the DNA set forth in SEQ ID NO: 52.

* * * * *

UNITED STATES PATENT AND TRADEMARK OFFICE
CERTIFICATE OF CORRECTION

PATENT NO. : 5,602,019

DATED : February 11, 1997

INVENTOR(S) : Beavo *et al.*

Page 1 of 6

It is certified that error appears in the above-identified patent and that said Letters Patent is hereby corrected as shown below:

Title page, (under Inventors) "Kelley J. Bentley" should be --J. Kelley Bentley--.

Col. 4, ln. 34 "...dunce locus..." should be --*dunce* locus--.

Col. 4, ln. 57 "...in vivo and in vitro..." should be --*in vivo* and *in vitro*--.

Col. 9, ln. 65 "...in vivo..." should be --*in vivo*--.

Col. 10, ln. 18 "...HindIII and NotI" should be --*Hind*III and *Not*I--.

Col. 10, ln. 20 "...HindIII and NotI" should be --*Hind*III and *Not*I--.

Col. 10, ln. 53 "...MgCl$_{b2}$..." should be --MgCl$_2$--.

Col. 12, ln. 36 "...EcoRI..." should be --*Eco*RI--.

Col. 12, ln. 63 "...EcoRI/blunt-ended..." should be *Eco*RI/blunt-ended--.

Col. 12, ln. 65 "...XhoI..." should be --*Xho*I--.

Col. 14, ln. 19 "...γZAP II" should be --λ ZAP II--.

Col. 14, ln. 23 "...EcoRI sites..." should be --*Eco*RI sites--.

Col. 14, ln. 24 "...EcoRI methylase and S-adenosyl methionine and EcoRI..." should be --*Eco*RI methylase and S-adenosyl methionine and *Eco*RI--.

UNITED STATES PATENT AND TRADEMARK OFFICE
CERTIFICATE OF CORRECTION

PATENT NO. : 5,602,019
DATED : February 11, 1997
INVENTOR(S) : Beavo et al.

It is certified that error appears in the above-identified patent and that said Letters Patent is hereby corrected as shown below:

Col. 14, ln. 25 "...EcoRI..." should be --EcoRI--.

Col. 14, ln. 28 "...γZAP II..." should be --λ ZAP II--.

Col. 14, ln. 35 "...γZAP II..." should be --λ ZAP II--.

Col. 15, ln. 39 "...by BamHI..." should be --by BamHI--.

Col. 15, ln. 44 "...tandem BamHI..." should be --tandem BamHI--.

Col. 15, ln. 63 "...units BamHI..." should be --units BamHI--.

Col. 15, ln. 66 "...with BamHI.." should be --with BamHI--.

Col. 16, ln. 3 "...into BamHI..." should be --into BamHI--.

Col. 16, ln. 8 "...BamHI insert..." should be --BamHI insert--.

Col. 16, lns. 8-9 "...HindIII..." should be --HindIII--.

Col. 16, ln. 11 "...HindIII and XbaI..." should be --HindIII and XbaI--.

Col. 16, ln. 13 "...HindIII- and XbaI-digested..." should be --HindIII- and XbaI-digested--.

Col. 16, ln. 58 "EcoRI..." should be --EcoRI--.

Col. 16, ln. 59 "...EcoRI..." should be --EcoRI--.

Col. 16, ln. 60 "...EcoRI..." should be --EcoRI--.

Col. 16, ln. 62 "...EcoRI..." should be --EcoRI--.

Col. 16, ln. 65 "...EcoRI-digested..." should be --EcoRI-digested--.

UNITED STATES PATENT AND TRADEMARK OFFICE
CERTIFICATE OF CORRECTION

PATENT NO. : 5,602,019

DATED : February 11, 1997

INVENTOR(S) : Beavo et al.

It is certified that error appears in the above-identified patent and that said Letters Patent is hereby corrected as shown below:

Col. 17, ln. 58 "...in vivo..." should be --*in vivo*--.

Col. 18, ln. 40 "...BamHI..." should be --*Bam*HI--.

Col. 19, ln. 24 "...HindIII and NotI..." should be --*Hind*III and *Not*I--.

Col. 19, ln. 40 "...γZAP..." should be --λ ZAP--.

Col. 19, ln. 42 "...EcoRI/ApaI..." should be --*Eco*RI/ApaI--.

Col. 19, ln. 61 "...in vivo..." should be --*in vivo*--.

Col. 20, ln. 12 "...PstI/SmaI..." should be --*Pst*I/*Sma*I--.

Col. 20, ln. 47 "...HindIII and NotI..." should be --*Hind*III and *Not*I--.

Col. 20, ln. 49 "..HindIII and NotI..." should be --*Hind*III and *Not*I--.

Col. 21, ln. 16 "...SmaI and EcoRI..." should be --*Sma*I and *Eco*RI--.

Col. 21, ln. 40 "...EcoRI..." should be --*Eco*RI--.

Col. 21, ln. 41"...EcoRI..." should be --*Eco*RI--.

Col. 21, ln. 55 "...EcoRI..." should be --*Eco*RI--.

Col. 21, ln. 56 "...HindIII..." should be --*Hind*III--.

Col. 21, ln. 59 "...EcoRI..." should be --*Eco*RI--.

Col. 21, ln. 61"...EcoRI/HindIII..." should be --*Eco*RI/*Hind*III--.

Col. 21, ln. 62 "...EcoRI and HindIII..." should be --*Eco*RI and *Hind*III--.

Col. 21, ln. 66 "...EcoRI..." should be --*Eco*RI--.

Col. 22, ln. 12 "...in vivo..." should be --*in vivo*--.

Col. 22, ln. 15 "...EcoRI..." should be --*Eco*RI--.

Col. 22, ln. 33 "...EcoRI-HindII..." should be --*Eco*RI-*Hind*II--.

Col. 22, ln. 65 "...EcoRI/XhoI..." should be --*Eco*RI/*Xho*I--.

Col. 23, ln. 52 "...AccI..." should be --*Acc*I--.

UNITED STATES PATENT AND TRADEMARK OFFICE
CERTIFICATE OF CORRECTION

PATENT NO. : 5,602,019

DATED : February 11, 1997

INVENTOR(S) : Beavo et al.

It is certified that error appears in the above-identified patent and that said Letters Patent is hereby corrected as shown below:

Col. 24, ln. 7 "...EcoRI..." should be --*EcoRI*--.

Col. 24, ln 8 "...EcoRI..." should be --*EcoRI*--.

Col. 24, ln . 9 "...EcoRI" should be --*EcoRI*--.

Col. 24, ln . 10 "...EcoRI/HindIII..." should be --*EcoRI*/*Hind*III--.

Col. 24, ln. 11 "...HindIII.." should be --*Hind*III--.

Col. 24, ln. 25 "...EcoRI..." should be --*EcoRI*--.

Col. 24, ln . 34 "...HindIII..." should be --*Hind*III--.

Col. 24, ln . 35 "...EcoRI/HindIII..." should be --*EcoRI*/*Hind*III--.

Col. 24, ln. 60 "...EcoRI..." should be --*EcoRI*--.

Col. 24, ln . 61 "...with EcoRI. Presumably one of the EcoRI..." should be --with *EcoRI*. Presumably one of the *EcoRI*--.

Col. 24, ln. 64 "...HindIII and EcoRI" should be --*Hind*III and *EcoRI*--.

Col. 24, ln . 65 "...HindIII..." should be --*Hind*III--.

Col. 24, ln . 67 "...HindIII/EcoRI..." should be --*Hind*III/*EcoRI*--.

Col. 25, ln. 4 "...HindIII..." should be --*Hind*III--.

Col. 25, ln. 20 "HindIII and EcoRI" should be --*Hind*III and *EcoRI*--.

Col. 25, ln . 25 "...in vivo..." should be --*in vivo*--.

Col. 25, ln. 58 "...pde$^{1-}$..." should be --*pde*$^{1-}$--.

Col. 25, ln. 59 "...pde$^{2-}$..." should be --*pde*$^{2-}$--.

Col. 25, ln. 66 "...in vivo..." should be --*in vivo*--.

Col. 26, ln. 19 "...HindIII..." should be --*Hind*III--.

Col. 26, ln. 28 "...HindIII..." should be --*Hind*III--.

UNITED STATES PATENT AND TRADEMARK OFFICE
CERTIFICATE OF CORRECTION

PATENT NO. : 5,602,019
DATED : February 11, 1997
INVENTOR(S) : Beavo et al.

It is certified that error appears in the above-identified patent and that said Letters Patent is hereby corrected as shown below:

Col. 26, lns. 42-43 "...HindIII and NotI and ligated to HindIII/NotI-digested..." should be --HindIII and NotI and ligated to HindIII/NotI-digested--.

Col. 27, ln. 66 "...HindIII..." should be --HindIII--.

Col. 28, ln. 6 "...NsiI..." should be --NsiI--.

Col. 28, lns. 8-9 "...with HindIII and NsiI was then ligated to HindIII- and NsiI-digested..." should be --with HindIII and NsiI was then ligated to HindIII- and NsiI-digested --.

Col. 28, ln. 11 "...HindIII and NotI..." should be --HindIII and NotI--.

Col. 28, ln. 13 "...HindIII and NotI..." should be --HindIII and NotI--.

Col. 29, ln. 32 "...EcoRI and SmaI..." should be --EcoRI and SmaI--.

Col. 29, ln. 52 "...EcoRI..." should be --EcoRI--.

UNITED STATES PATENT AND TRADEMARK OFFICE
CERTIFICATE OF CORRECTION

PATENT NO. : 5,602,019
DATED : February 11, 1997
INVENTOR(S) : Beavo et al.

It is certified that error appears in the above-identified patent and that said Letters Patent is hereby corrected as shown below:

Col. 30, ln . 32-33 "...(AccI/SstI and Tth111I/HincII)..." should be --(AccI/SstI and Tth111I/HincII)--.

Signed and Sealed this

Seventeenth Day of February, 1998

BRUCE LEHMAN

Attest:

Attesting Officer

Commissioner of Patents and Trademarks

UNITED STATES PATENT AND TRADEMARK OFFICE
CERTIFICATE OF CORRECTION

PATENT NO. : 5,602,019
DATED : February 11, 1997
INVENTOR(S) : Beavo et al.

It is certified that error appears in the above-identified patent and that said Letters Patent is hereby corrected as shown below:

Col. 128, ln. 34, delete "17" and substitute --18--.

Signed and Sealed this

First Day of December, 1998

BRUCE LEHMAN

Attest:

Attesting Officer

Commissioner of Patents and Trademarks